(12) United States Patent   (10) Patent No.: US 7,577,469 B1
Aronowitz et al.   (45) Date of Patent: Aug. 18, 2009

(54) NONINVASIVE TRANSDERMAL SYSTEMS FOR DETECTING AN ANALYTE IN A BIOLOGICAL FLUID AND METHODS

(75) Inventors: Jack L. Aronowitz, 6591 Skyline Dr., Delray Beach, FL (US) 33446; Joel R. Mitchen, Pompano Beach, FL (US); John Weiss, Holtsville, NY (US); Irwin Weitman, East Northport, NY (US)

(73) Assignee: Jack L. Aronowitz, Pompano Beach, FL (US)

( * ) Notice: Subject to any disclaimer, the term of this patent is extended or adjusted under 35 U.S.C. 154(b) by 0 days.

(21) Appl. No.: 09/266,346

(22) Filed: Mar. 11, 1999

(51) Int. Cl.
*A61B 5/1455* (2006.01)
(52) U.S. Cl. ........................ 600/310; 600/316
(58) Field of Classification Search ................. 600/309, 600/310, 316, 365
See application file for complete search history.

(56) References Cited

U.S. PATENT DOCUMENTS

| | | |
|---|---|---|
| 3,910,701 A | 10/1975 | Henderson et al. |
| 4,163,950 A | 8/1979 | Damm et al. |
| 4,169,676 A | 10/1979 | Kaiser |
| 4,427,889 A | 1/1984 | Müller |
| 4,446,232 A | 5/1984 | Liotta |
| 4,627,445 A | 12/1986 | Garcia et al. |
| 4,706,676 A | 11/1987 | Peck |
| 4,723,554 A | 2/1988 | Oman et al. |
| 4,774,192 A | 9/1988 | Terminiello et al. |
| 4,781,195 A | 11/1988 | Martin |
| 4,819,645 A | 4/1989 | Peck |
| 4,821,733 A | 4/1989 | Peck |
| 4,909,256 A | 3/1990 | Peck |
| 4,913,150 A * | 4/1990 | Cheung et al. ............... 600/323 |
| 4,960,467 A | 10/1990 | Peck |

(Continued)

FOREIGN PATENT DOCUMENTS

EP   0 160 768 A1   11/1985

(Continued)

OTHER PUBLICATIONS

Bauer, et al., "Monitoring of Glucose in Biological Fluids by Fourier-Transform Infrared Spectrometry with a Cylindrical Internal Reflectance Cell", *Analytica Chim. Acta* (1987), 197:295-301; Elsevier Science B.V.

(Continued)

*Primary Examiner*—Eric F Winakur
(74) *Attorney, Agent, or Firm*—Saliwanchik, Lloyd & Saliwanchik

(57) ABSTRACT

The present invention relates to noninvasive transdermal systems comprised of a noninvasive transdermal patch and a reflectometer. The noninvasive transdermal patches are comprised of a wet chemistry component and a dry chemistry component. The wet chemistry component is a liquid transfer medium in the form of a gel layer for the extraction and liquid bridge transfer of the analyte of interest from the biological fluid within or beneath the skin to the dry chemistry component. The dry chemistry component is a reagent system for interacting with the analyte of interest (glucose) to generate a color change. The reflectometers include a modulated light source for emitting light to illuminate a target surface which possesses a certain color and shade of color for detection by an optical detector. The output signal is processed for determining a corresponding quantity or quality measurement.

72 Claims, 45 Drawing Sheets

U.S. PATENT DOCUMENTS

| | | | |
|---|---|---|---|
| 5,174,963 | A | 12/1992 | Fuller et al. |
| 5,179,288 | A | 1/1993 | Miffitt et al. |
| 5,203,327 | A | 4/1993 | Schoendorfer et al. |
| 5,443,080 | A | 8/1995 | D'Angelo et al. |
| 5,462,064 | A | 10/1995 | D'Angelo et al. |
| 5,477,853 | A * | 12/1995 | Farkas et al. ............ 600/310 |

FOREIGN PATENT DOCUMENTS

| | | | |
|---|---|---|---|
| EP | 0 182 647 | A2 | 5/1986 |
| EP | 0 426 967 | A2 | 5/1991 |
| EP | 0 472 983 | A2 | 3/1992 |
| EP | 0 477 417 | A1 | 4/1992 |
| WO | WO 83/00926 | A1 | 3/1983 |
| WO | WO 97/02811 | | 1/1997 |
| WO | WO 99/23479 | A1 | 5/1999 |

OTHER PUBLICATIONS

Dappen, G.N., et al, "Dry film for the enzymic determination of total chilesterol in serum", *Clin. Chem.* (1982), 28(5):1159-62.

Spayd, R.W., et al., "Multilayer film elements for clinical analysis: applications to representative chemical determinations", *Clin Chem.* (1978) 24(8):1343-50.

Toffaietti, J., et al., "An Automated Dry-Slide Enzymatic Method Evaluated for Measurement of Creatinine in Serum", *Clin. Chem.* (1983), 29(4):684.

* cited by examiner

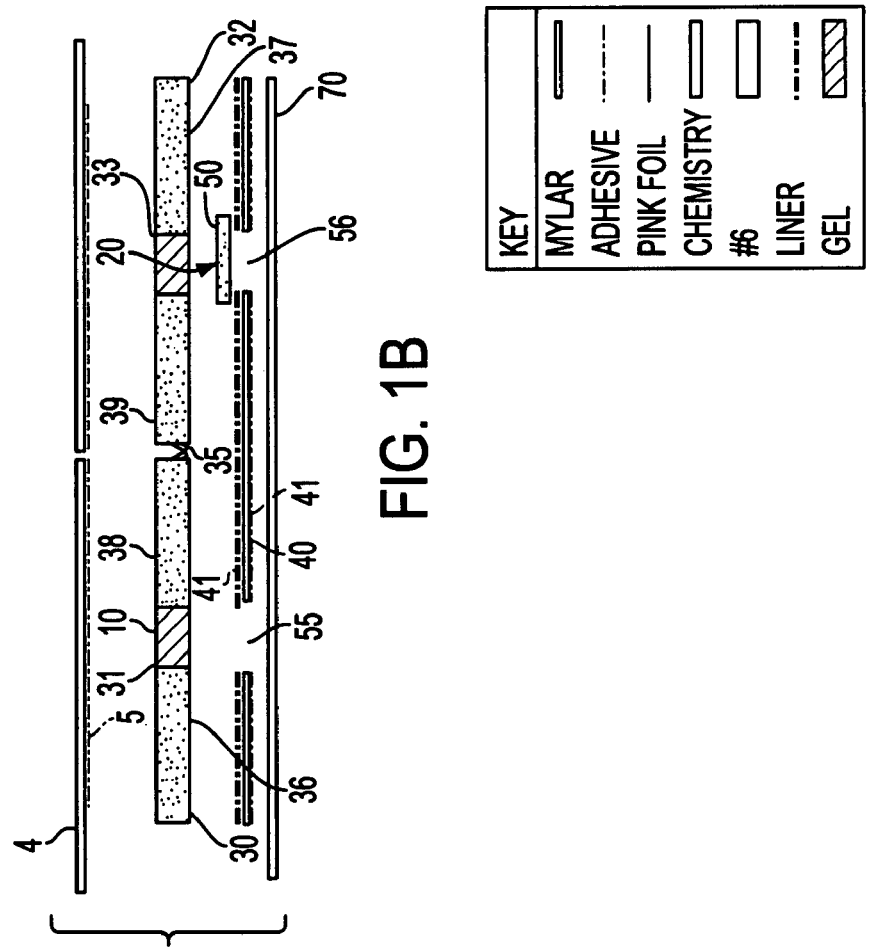
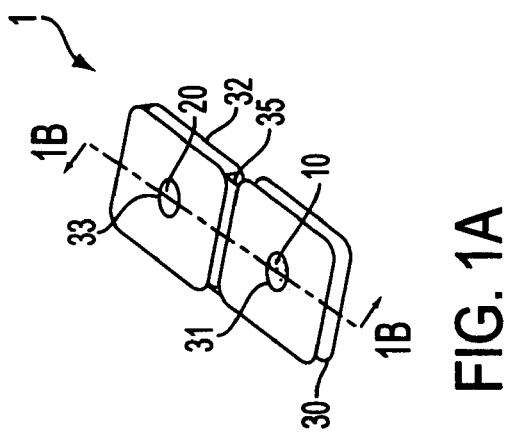
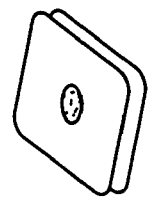

| [GLUCOSE] mg/dl | REFLECTANCE # |
|---|---|
| 0.0 | 2,025 |
| 12.5 | 1,932 |
| 25.0 | 2,387 |
| 50.0 | 2,508 |
| 100.0 | 2,770 |
| 200.0 | 2,928 |
| 300.0 | 3,137 |

AVG. OF NINE DETERMINATIONS FOR EACH SAMPLE
4%c.v
r=0.99

FIG. 15A

| TIME (MIN.) POSTPRANDIAL | BLOOD GLUCOSE STANDARD METHOD | NONINVASIVE GLUCOSE TEST KIT CALCULATED* | REFLECTANCE# NONINVASIVE TEST |
|---|---|---|---|
| 0 | 78 | 80 | 2,559 |
| 15 | 94 | 78 | 2,544 |
| 25 | 120 | 130 | 2,680 |
| 32 | 117 | 110 | 2,599 |
| 68 | 92 | 95 | 2,547 |
| 11 | 92 | 95 | 2,546 |
| 150 | 76 | 75 | 2,434 |
| 180 | 73 | 85 | 2,520 |

AVG. OF TWO DETERMINATIONS PER TIME POINT
MALE AGE 53 FASTED 12 HOURS
THEN DRANK 100 GRAMS D-GLUCOSE
*r=0.94

FIG. 15B

FIVE MINUTES SKIN CONTACT TIME

FIVE MINUTES SKIN CONTACT TIME

FIVE MINUTES SKIN CONTACT TIME

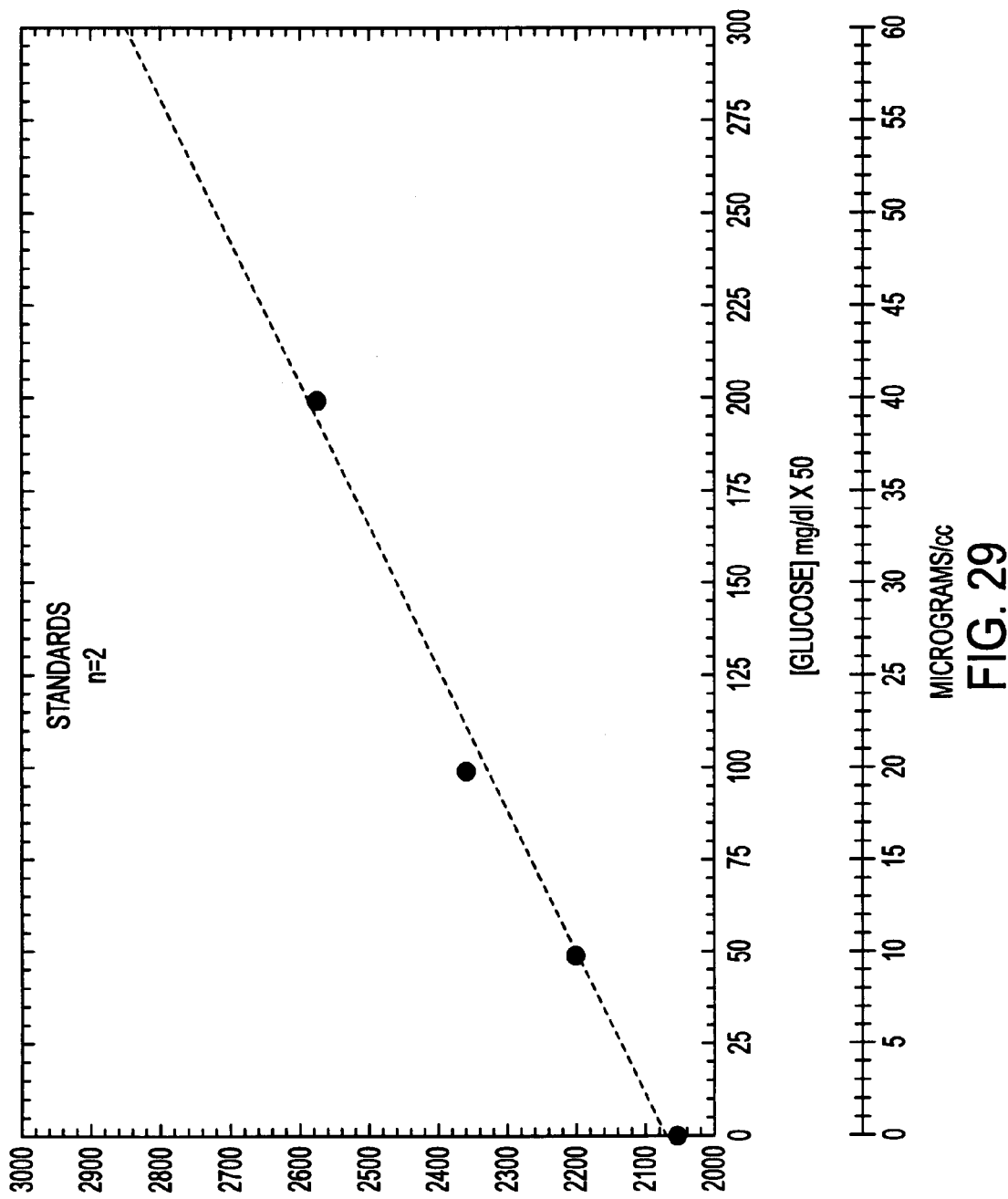

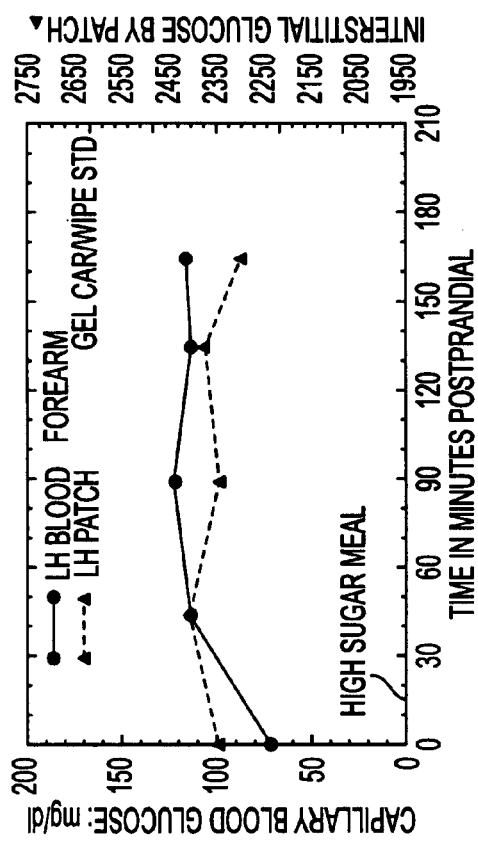
FIG. 31
FIG. 30
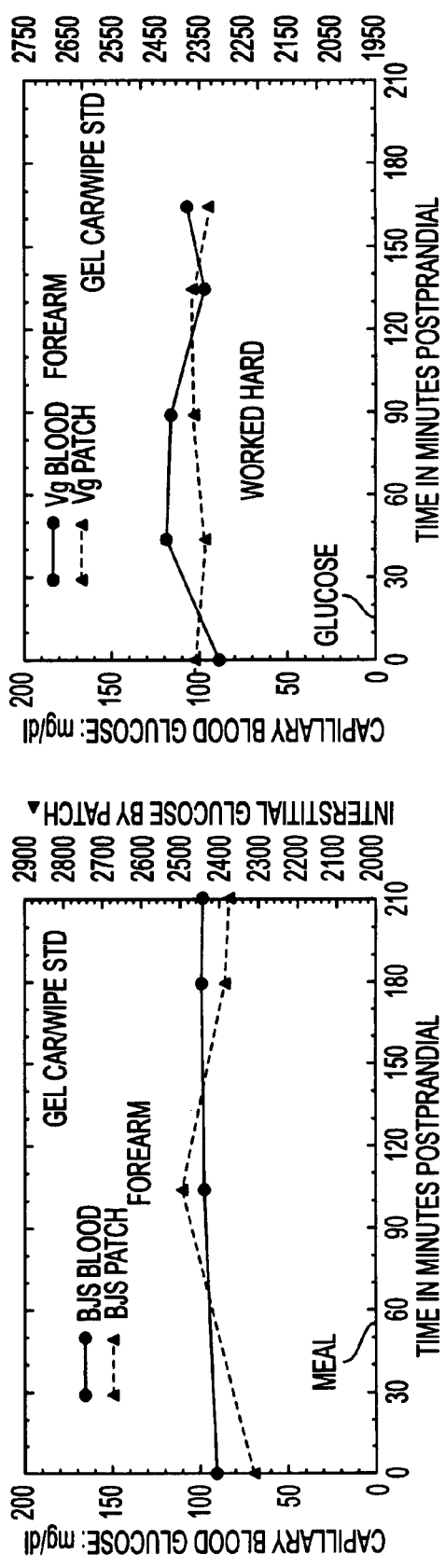
FIG. 33
FIG. 32

| MV | mg/dL |
|---|---|
| 400 | 625 |
| 450 | 575 |
| 500 | 475 |
| 550 | 300 |
| 600 | 230 |
| 650 | 180 |
| 700 | 140 |
| 750 | 105 |
| 800 | 75 |
| 850 | 55 |

NONINVASIVE TRANSDERMAL SYSTEMS FOR DETECTING AN ANALYTE IN A BIOLOGICAL FLUID AND METHODS

FIELD OF THE INVENTION

The present invention concerns noninvasive transdermal systems and methods for analyte extraction from a biological fluid within or beneath the skin, such as interstitial fluid, and detection of the analyte. More particularly, the present invention relates to noninvasive transdermal systems comprised of a noninvasive patch and a reflectometer for detecting an analyte of interest and methods. The noninvasive patches include a wet chemistry component for extraction of the analyte of interest from a biological fluid within or beneath the skin and presentation to a dry chemistry component which interacts with the analyte for indicator molecule formation to confirm detection of the analyte, and methods of use thereof.

The present invention also relates to reflectometer technology and, in particular, to a method and apparatus for detecting and measuring color shades with a relatively high degree of accuracy. Where the color shades are indicative of a certain measurable quantity or quality, the present invention further relates to method and apparatus for converting the detected color shade into a corresponding quantity or quality measurement.

BACKGROUND

The determination of an individual's physiological status is frequently assisted by chemical analysis for the existence and/or concentration level of an analyte in a body fluid. This practice is common in the diagnosis of diabetes and in the management of this disease. Blood sugar levels can generally fluctuate with the time of day and with the period since the individual's last consumption of food. Management of diabetes often, thus, requires the frequent sampling and analysis of the diabetic's blood for determination of its relative glucose level. The management of this disease by the diabetic will typically involve the sampling of his/her own blood, the self-analysis of the sample for its relative glucose content and the administration of insulin, or the ingestion of sugar, depending upon the indicated glucose level.

Presently, the only approved method for home monitoring of blood chemistry requires drawing blood by using a lance, usually by sticking a finger, and placing a drop of blood on a chemical strip. The resulting chemical reaction causes a change in the color of the strip with that change being read by a desk-top reflectance meter to provide an indication of blood sugar level. Another method also requires drawing blood, placing a drop of blood on a disposable printed circuit (PC) board, and measuring the electrical response of the blood to detect blood sugar level. Some attempts to use infrared techniques to look through the skin to make blood sugar determinations have proven to be less reliable and too expensive for commercial application.

Diabetics who need to control their insulin level via diet or insulin injection may test themselves several times per day, i.e., five or six times per day, the frequency recommended by the American Diabetes Association. Some may choose to test less often than recommended to avoid the unpleasantness associated with drawing blood. Unfortunately, the current methods of monitoring blood glucose levels has many drawbacks. The current methods generally rely upon finger lancing to monitor blood glucose levels, which is not easy for anyone, especially young children and the elderly. Moreover, because blood is involved, there is always the risk of infection and of transmission of blood borne diseases, such as AIDS. Still further, special procedures and systems for handling and disposing of the blood are required. If the blood glucose concentrations in such individuals are not properly maintained, the individuals become susceptible to numerous physiological problems, such as blindness, circulatory disorders, coronary artery disease, and renal failure. For these reasons, there is a great unmet need for a noninvasive method for monitoring blood glucose levels. A substantial improvement in the quality of life of persons suffering from various maladies, such as diabetes mellitus, could be attained if the concentrations of species in body fluids are noninvasively determined. There is accordingly a considerable amount of interest in the development of procedures for making blood sugar level determinations that avoid any need for inflicting injury to the patient.

There are a number of devices on the market to assist the diabetic in the self-testing of the blood sugar level. One such device, developed by Audiobionics (now Garid, Inc.) and described in U.S. Pat. No. 4,627,445, issued Dec. 9, 1986, involves the use of a fixture containing a multi-layered element for the collection of the whole blood sample, the transport of the sample from the point of application on the element to a porous membrane, and the analysis of the blood sample for its glucose contents by a dry chemistry reagent system which is present within the porous membrane.

Other such devices described in U.S. Pat. Nos. 5,462,064 and 5,443,080 and issued to J. P. D'Angelo et al. involve the use of a multi-part system to collect and analyze constituents of body fluid. In D'Angelo et al., the systems rely upon, among other things, a multilayered gel matrix which includes a separate activation gel layer and a separate collection gel layer disposed below the activation gel layer, an osmotic flow enhancer, such as ethyl ether, to facilitate the collection of an analyte fluid, and a chemistry detection methodology to aid in the visual or electronic determination of an analyte under investigation. Ethyl ether, however, is a known skin irritant which is flammable and explosive.

Another such device described in U.S. Pat. No. 5,203,327 and issued to D. W. Schoendorfer et al., involves a method and apparatus for the non-invasive determination of one or more preselected analytes in perspiration. In D. W. Schoendorfer, et al., the fluid is collected in a dermal concentration patch and concentrated by driving off a portion of the substantial water fraction under the influence of body heat, and the analyte is optimally complexed with an immobilized specific binding partner and an indicium of the presence of the analyte is usually experienced.

Other such devices are described in U.S. Pat. Nos. 4,960,467; 4,909,256; 4,821,733; 4,819,645; and 4,706,676 and issued to Peck. According to these patents, the Peck devices involve a dermal substance collection device (DSCD) which provides for the non-invasive, instantaneous and continuous monitoring of chemical substances which are present in detectable amounts in either or both interstitial fluid or sweat or which are on or in the skin. More particularly, the Peck transdermal substance collection devices are comprised of three essential components: (1) a substance binding reservoir, wettable by (2) a liquid transfer medium which allows for liquid bridge transfer of a soluble substance from the skin surface to the biding reservoir by virtue of its wettability by the liquid, and (3) an occlusive cover.

Exemplary of other systems have been previously proposed to monitor glucose in blood, as is necessary, for example, to control diabetic patients. This is represented, for example, by Kaiser, U.S. Pat. No. 4,169,676, Muller, U.S. Pat. No. 4,427,889, and Dahne et al. al., European Patent Publication No. 0 160 768, and Bauer et al., *Analytica Chimica Acta* 197 (1987) pp. 295-301.

In Kaiser, glucose in blood is determined by irradiating a sample of the blood with a carbon dioxide laser source emitting a coherent beam, at a single frequency, in the mid-infrared region. An infrared beam derived from the laser source is coupled to the sample by way of an attenuated total reflectance crystal for the purpose of contacting the blood sample. The apparatus uses double beam instrumentation to examine the difference in absorption at the single frequency in the presence and absence of a sample.

Muller discloses a system for quantifying glucose in blood by irradiating a sample of the blood with energy in a single beam from a laser operating at two frequencies in the mid-infrared region. The infrared radiation is either transmitted directly to the sample or by way of an attenuated total reflectance crystal for in vitro sampling. One frequency that irradiates the sample is in the 10.53-10.6 micrometer range, while the other irradiating frequency is in the 9.13-9.17 micrometer range. The radiation at the first frequency establishes a baseline absorption by the sample, while glucose absorption by the sample is determined from the intensity reduction caused by the sample at the second wavelength. The absorption ratio by the sample at the first and second frequencies quantifies the glucose of the sample.

Dahne et al. employ near-infrared spectroscopy for noninvasively transmitting optical energy in the near infrared spectrum through a finger or earlobe of a subject. Also discussed is the use of near-infrared energy diffusely reflected from deep within the tissue. Responses are derived at two different wavelengths to quantify glucose in the subject. One of the wavelengths is used to determine background absorption, while the other wavelength is used to determine glucose absorption. The ratio of the derived intensity at the two different wavelengths determines the quantity of glucose in the analyte biological fluid sample.

Bauer et al. disclose monitoring glucose through the use of Fourier-transform infrared spectrometry wherein several absorbance versus wavelength curves are illustrated. A glucose concentration versus absorbance calibration curve, is constructed from several samples having known concentrations, in response to the intensity of the infrared energy absorbed by the samples at one wavelength, indicated as preferably 1035 $cm^{-1}$.

Notwithstanding the above, the most frequently employed systems for determining the concentration of molecular substances in biological fluids have used enzymatic, chemical and/or immunological methods. However, these techniques generally require invasive methods to draw a blood sample from a subject; typically, blood must be drawn several times a day by a finger prick, such as presently employed by a diabetic and externally determining the glucose level, generally by chemical reaction followed by calorimetric comparative testing. For example, in the determination of glucose by diabetics, such invasive techniques must be performed using present technology.

Because the prior art invasive techniques are painful, individuals frequently avoid having blood glucose measured. For diabetics, the failure to measure blood glucose on a prescribed basis can be very dangerous. Also, the invasive techniques, which rely upon lancing blood vessels, create an enhanced risk for disease transmission and infection.

Thus, there remains a need in many diverse applications for a system for the noninvasive, painless determination of a preselected analyte in a body fluid, such as interstitial fluid, which can be utilized to detect the presence of the preselected analyte. Clearly, in the case of diabetics, it would be highly desirable to provide a less invasive system for analyzing glucose concentrations in the control of diabetes mellitus. However, with respect to transdermal detection mechanism, the extracted analytes which are indicative of widely varying blood sugar levels may produce only very slight changes in developed color shade. In many instances, the difference between developed color shade for an acceptable and an unacceptable blood sugar level cannot be accurately and repeatably detected by the naked eye. To obtain the noninvasive benefits of transdermal glucose measurement technology while ensuring measurement accuracy in what may comprise a life critical testing procedure, it is therefore imperative that the fallible human activity of color shade evaluation and comparison be eliminated from the testing and measurement process.

There is accordingly a need for an ultra-sensitive meter capable of accurately resolving the full range of developed subtle color shade changes produced as a result of transdermal patch extraction and processing of certain analytes of interest. Preferably, the meter should be small, lightweight and portable (hand held). Beyond the obvious requirements for improved sensitivity to subtle differences in color shade, this meter should account for the effects of portability which are adverse to reading accuracy such as background light changes, temperature changes, and unsteady hand-held operation (for example, due to device pressure variation, rotation, and movement), and which are not normally associated with the desk-top meters that are widely employed for measuring blood sugar levels on test strips. Moreover, the entire system for noninvasive detection should be low-cost and suitable for convenient use by non-medical personnel.

SUMMARY OF THE INVENTION

In brief, the present invention overcomes certain of the above-mentioned drawbacks and shortcomings through the discovery of a novel transdermal system for detecting an analyte of interest in a biological fluid and methods concerning same, without resort to prior standard invasive, painful techniques. In accordance with the present invention, the novel noninvasive transdermal systems provide for sample collection and detection in the form of a simple, easy-to-use, integrated system which is low-cost and suitable for convenient use by non-medical personnel. Moreover, because the novel transdermal systems of the present invention are noninvasive and painless, as compared to the invasive techniques generally utilized heretofore, e.g, a finger prick or finger lance, individual compliance should be enhanced, and the risk of disease transmission and infection should be reduced.

With the foregoing in mind and other objects in view, there is provided, in accordance with the present invention, a noninvasive transdermal system for collecting and detecting an analyte of interest in a biological fluid within or underneath the skin. Generally speaking, the noninvasive transdermal systems of this invention are comprised of two essential components: (1) a dry chemistry component; and (2) a wet chemistry component. The dry chemistry component comprises a super sensitive or conditioned membrane containing a compliment of chemical reagents which are specific for reacting with one or more analytes of interest. The interaction of the analyte(s) and such chemical reagents is manifest by the release or formation of indicator molecules, e.g., color change, which is indicative of the presence of the analyte(s) in the biological fluid. The surface of the super sensitive or conditioned membrane, which is receptive of and exposed to the analyte of interest, is relatively dense, thereby being generally free of cells, particles and/or other micromolecules which can potentially interfere with reaction of the analyte and the chemical reagents and/or the detection of a reporter molecule. In contrast, the opposing surface of the super sensitive or conditioned membrane is substantially less dense (more porous), thereby allowing for infusion of the reagent system during manufacture, and the formation, diffusion and visualization of reporter or indicator molecules, which are indicative of the presence of the analyte of interest and its level of concentration in the body fluid. The super sensitive or conditioned membranes of the present invention have the unique ability to detect analytes in very small sample volumes, e.g., about 25 mcl, in very small concentrations which are at least as low as about 5 mg/dl or about 5 mcg/ml.

The wet chemistry component of the present invention comprises a generally liquid transfer medium which allows for liquid bridge transfer or extraction of an analyte of interest from the biological fluid within or underneath the skin to the super sensitive or conditioned membrane for reaction with the reagents to release or form the reporter or indicator molecule, which is indicative of the presence of the analyte in the biological fluid.

More specifically, and in accordance with the present invention, the compliment of reagents, with which the membrane is conditioned, includes a chemical reactant and a color developer specifically provided for an analyte of interest. Also in accordance with the present invention, the liquid transfer medium is in the form of a gel layer or gel matrix which permits for liquid transfer or extraction of the soluble analyte under investigation from the biological fluid within or underneath the skin to the site of reaction at the super sensitive or conditioned membrane. Preferably, the gel layer is a hydrophobic gel which is inert, nonflammable and nonirritating to the skin. An especially preferred hydrophobic gel in accordance with the present invention is a gel formulated with carboxy polymethylene, marketed or sold under the brand name Carbopol®, and deionized water (18 meg ohm) in a concentration of from about 0.5% to about 2.0%, and preferably in a concentration of about 1%.

In accordance with a further feature of the present invention, the gel includes a permeation skin enhancer selected for the analyte to be detected for enhancing the liquid bridge transfer or extraction of the analyte from the biological fluid within or underneath the skin to the super sensitive or conditioned membrane for reaction and detection. Preferred skin permeation enhancers contemplated by the present invention are those which are nonflammable, nonexplosive and nonirritating to the skin, and which do not interfere with the analyte under investigation, its transfer to the super sensitive or conditioned membrane and its interaction with the chemical reagents. In accordance with the present invention, a preferred skin permeation enhancer is propylene glycol elegantly admixed in the gel in a concentration of from about 5% to about 20%, and especially admixed in the gel in a concentration of about 10%. Thus, an especially preferred gel in accordance with the present invention comprises about 1% carboxy polymethylene, e.g., Carbopol®, and about 10% propylene glycol in deionized water (18 meg ohm).

Alternatively, and also in accordance with the present invention, a skin permeation enhancer may be first directly applied to the targeted skin area to which the transfer medium or gel is applied. While the present invention contemplates the use of a permeation enhancer separate from or in addition to the transfer medium gel, it has been surprisingly discovered that, when a skin permeation enhancer is incorporated into the transfer medium or gel, it is not necessary to apply a skin permeation enhancer directly to the skin before applying the novel noninvasive transdermal systems of the present invention.

Also in accordance with the present invention, the novel noninvasive transdermal systems can be configured as a component of a noninvasive transdermal patch for collection and detection of an analyte in a biological fluid within or underneath the skin. When configured into a noninvasive transdermal patch, it is contemplated that the dry chemistry component and the wet chemistry component are maintained separately prior to use and that, upon use, the super conditioned membrane and the transfer medium shall be the exclusive means of access of the analyte under investigation to the chemical reagents infused onto and/or within the membrane.

In a preferred embodiment in accordance with the present invention, the body fluid from which an analyte may be transdermally extracted is interstitial fluid.

In yet a further feature of the present invention, an electronic interpretation component may be utilized for detecting the reporter or indicator molecules, e.g., color change, generated from the presence of the analyte in the biological fluid and its reaction with the chemical reagents. The electronic interpretation components should include a light source for illuminating the indicator molecule, a photosensor sensing a reflecting intensity from the indicator molecules and a system for interpreting the measured reflectance intensity and providing information regarding a result of the interpretations. Thus, the present invention comprises a reflectometer for detecting and measuring subtle changes in color and shade of color. In general, a pulsating light source illuminates a target surface which possesses a certain color and shade of color. An optical detection circuit synchronously detects light that is reflected from the target surface and generates an output signal whose voltage is indicative of the color and shade of the target surface. This voltage is then processed to make an evaluation and identification of any measurable quantity or quality that is represented by the detected color or shade of color.

More specifically, a modulated light source emits light to illuminate the colored target surface, where the specific color or shade of color is indicative of a certain measurable quantity or quality (such as an analyte concentration). The modulated light that is reflected from the target surface is detected by an optical detector. The output signal from the optical detector is differentially amplified to produce an AC output signal indicative of the color and shade of the target surface. The output signal from the optical detector is further processed and fed back to the optical detector to compensate for any shift in the DC level of the AC output signal caused by the detection of ambient light or the influence of other external factors. The output signal from the differential amplifier is then demodulated by a synchronous detector to produce a substantially steady DC voltage that is indicative of the color or shade of color at the target surface. This DC voltage is converted to a corresponding digital value, and that digital value is converted using a look-up table or other mathematical formula into a corresponding quantity or quality measurement.

It should nevertheless be understood that, while any commercial reflectometer capable of reading a color change in a wavelength range of, for example, about 500 nm to about 930 nm at an angle of reflection in the range of about 30° to about 90° with a voltage of from about 200 mV to about 1 mV with a sensitivity of about ±0.1 mV, may be used in accordance with the novel noninvasive transdermal systems of the present invention, the reading head of such reflectometers should preferably be configured so as to interface precisely with the recess or through aperture leading to the dry chemistry component of the novel noninvasive transdermal systems. Preferably, the reading head of a reflectometer should have a matching sensor and LED which can read reflectance from color in a wavelength range of from about 650 nm to about 670 nm at an angle of reflectance in the range of about 35° to about 45° with such sensitivity. FIG. 9 depicts an exemplary reflectometer in accordance with the present invention having a reading head which is configured for precise interface with a recess or through aperture that leads to the dry chemistry component or membrane. The reflectometer depicted in FIG. 9 further includes a visual display for communicating the results detected by the reflectometer. FIG. 10 illustrates a cross section of a reflectometer depicted in FIG. 9 for interfacing with a transdermal patch of the present invention at about a 40°-45° angle of reflectance for reading color intensity for analyte detection.

With the above-listed objects in view, there is provided, in accordance with the present invention, a collection and indication apparatus for biological fluid constituent analysis, which comprises a collector component for noninvasively and transdermally collecting a body fluid analyte from an individual or subject in the form of a dry chemistry component including a compliment of chemical reagents for reacting with the analyte for indicating its presence and a wet chemistry component for extracting and transferring the analyte from the body fluid within or underneath the skin to the chemical reagents; and a configuration specifically designed for keeping the dry chemistry component and the wet chemistry component intact and separate from one another during non-use, but which allows them to intimately engage one another during testing, so that the dry chemistry component is continuously and uniformly wetted during testing by the wet chemistry component and the analyte under investigation can be extracted and transferred from the biological fluid within or underneath the skin to the super sensitive or concentrated membrane for interaction with the chemical reagents to generate the reporter or indicator molecules, e.g., color change, to confirm analyte presence. Preferably, the body fluid is interstitial fluid from which the analyte is transdermally and noninvasively extracted and collected.

In other words, the novel noninvasive, transdermal systems of the present invention include three major operational components. The first is the wet chemistry component which functions as the liquid bridge for transferring the analyte of interest from the biological fluid within or underneath the skin to the dry chemistry component, the second component is the dry chemistry component infused with a chemical reaction system specifically for interacting with the analyte of interest to detect its presence, and the third component is a support or housing for the systems which are configured to ensure that the wet and dry chemistry components remain separate during nonuse, but are in direct and continuous contact when the systems are in use and which enables the individual users to physically hold the systems and review the generated data in a rapid and meaningful way. In addition, the novel noninvasive transdermal systems of the present invention contemplate the use of a permeation skin enhancer admixed into the wet chemistry component and/or at the targeted skin areas prior to application of the novel noninvasive transdermal systems to such skin areas. Still further, the novel noninvasive transdermal systems of the present invention contemplate an electronic interpretation component especially configured for precise interfacing with the dry chemistry component, so that the reading head can read changes in color intensity in a preferred wavelength range of about 650 nm±10 nm at an angle of reflectance of about 40° with a sensitivity precision of about ±0.1 mV. In other words, the electronic interpretation component of the system is configured so as to read the patch component in the event of a visual impairment, or if a more precise numerical value is required, it will give a report in that format.

A novel method of combining test chemistries known to those in the healing arts with the interstitial fluid collection medium in such a manner as to cause to be noninvasively and transdermally extracted from or through the skin, a quantity of analyte of interest sufficient for the chemical test to proceed and then to have the ability to read and record the results in a very short period of time, e.g., a few minutes, is described. This is one of the major objects of this invention.

In a preferred embodiment, the present invention contemplates small disposable transdermal patches for use with a reflectometer to detect an analyte such as glucose. In accordance with the present invention, the small disposable transdermal patches measure blood glucose levels noninvasively. In actuality, the small disposable transdermal patches of the present invention have the unique ability to detect the levels of glucose in interstitial fluid which directly correlate to those levels in the blood. Briefly, and not to be limited, the process is believed to occur as follows. A small disposable transdermal patch of the present invention, which is strategically placed on the targeted skin area, painlessly draws glucose from the interstitial fluid through the skin. The glucose is transported by the skin permeation enhancer combined with a gel capable of transporting glucose through the stratum corneum (upper level of the epidermis). The glucose in the interstitial fluid then undergoes a glucose-specific biochemical reaction at the site of the dry chemistry membrane, the biochemical reaction of which are contained within the dry chemistry membrane in the patch. This biochemical reaction results in a color formation which is then measured by a reflectometer and directly correlated to the blood glucose levels. It is believed that the membrane based technology of the present invention is at least 100, if not 400-500, times more sensitive for detection of very small concentrations of an analyte, e.g., about 5 mg/dl or 5 mcg/ml, in a very small volume of fluid, e.g., about 25 mcl, than what is being currently used with finger stick or finger lancing technology. Thus, and in accordance with the present invention, the extraction and detection process only requires a small patch and a small hand held reflectometer. And, because blood is not at all involved, pain and the risk of infection and disease transmission generally associated with glucose monitoring have been eliminated. Moreover, special handling procedures or disposal systems are no longer required.

The noninvasive transdermal systems of the present invention analyze analytes in interstitial fluid rather than blood. Interstitial fluid is the nutrient fluid between the cells within the body tissues. The volume of interstitial fluid in the body is more than three time the blood volumes, and the concentrations of various constituents of the interstitial fluid are generally in equilibrium with the concentrations of those same constituents in blood. In accordance with the present invention, it is believed that small quantities of analyte in the interstitial fluid diffuse into the novel noninvasive transdermal systems with the aid of the gel in combination with a skin permeation enhancer. Once inside the systems of the present invention, the analyte of interest, e.g., glucos, from the interstitial fluid undergoes an enzymatic reaction which leads to the formation of colored indicator material. The color produced is believed to be proportional to the concentration of the analyte in the interstitial fluid, which in turn is proportional to the analyte concentration in the blood. This color is measured by, for example, surface reflectance via a fixed-wavelength optical meter, and is then compared to onboard calibration values. The result for the detected analyte is typically displayed in units of mg/dl.

An integral component of the invention is the transdermal patch which allows the system to work as a non-invasive skin test for clinical analytes. Additionally, what is shown and described are various configurations, all of which work together as a new and novel system to evaluate chemical analytes from noninvasively and transdermally extracted biological fluids.

Other features which are considered as characteristic for the invention are set forth in the appended claims.

Although the present invention is illustrated and described herein as embodied in an integrated noninvasive and transdermal system for biological fluid constituent analysis, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of specific embodiments when read in connection with the accompanying Figs. and examples.

The above features and advantages of the present invention will be better understood with reference to the following detailed description and examples. It should also be understood that the particular methods and formulations illustrating the present invention are exemplary only and not to be regarded as limitations of the present invention.

BRIEF DESCRIPTION OF THE FIGS.

Reference is now made to the accompanying Figs. in which a more complete understanding of the systems, including the methods and apparatus, of the present invention may be acquired by reference to the following Detailed Description when taken in conjunction with the accompanying Figs., wherein:

FIG. 15A is a table depicting the data of the calibration curve of FIG. 14;

FIG. 15B is a table of data corresponding to FIG. 11;

Figure 26:
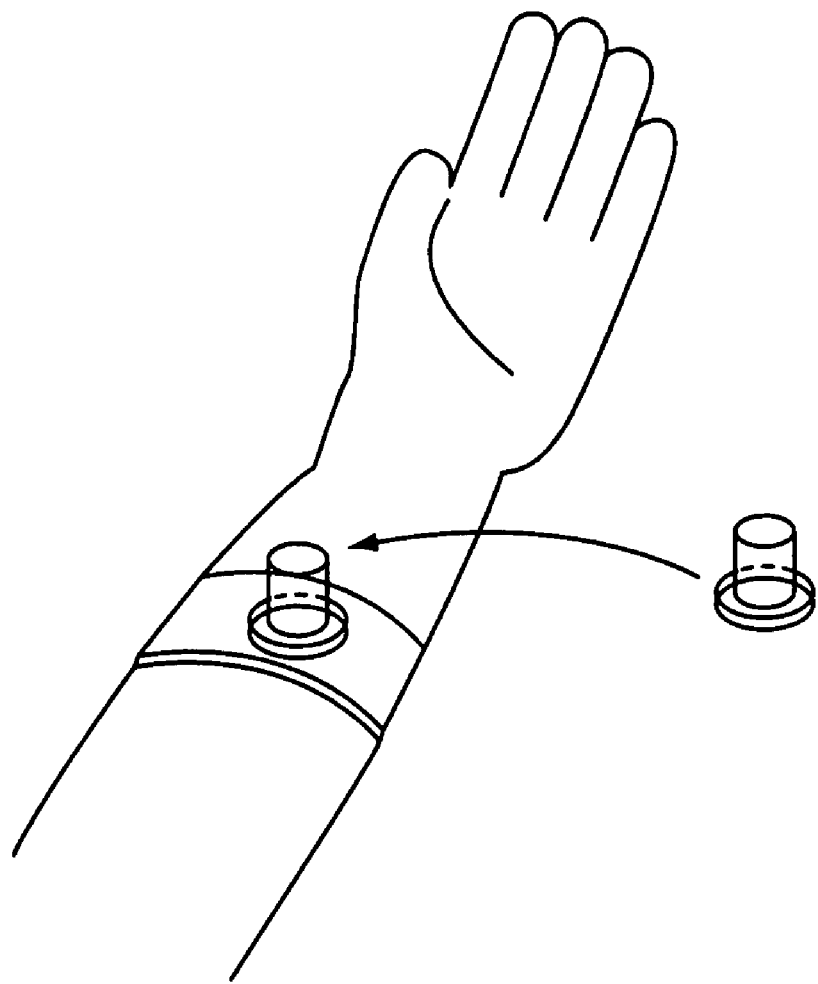
Figure 27A:
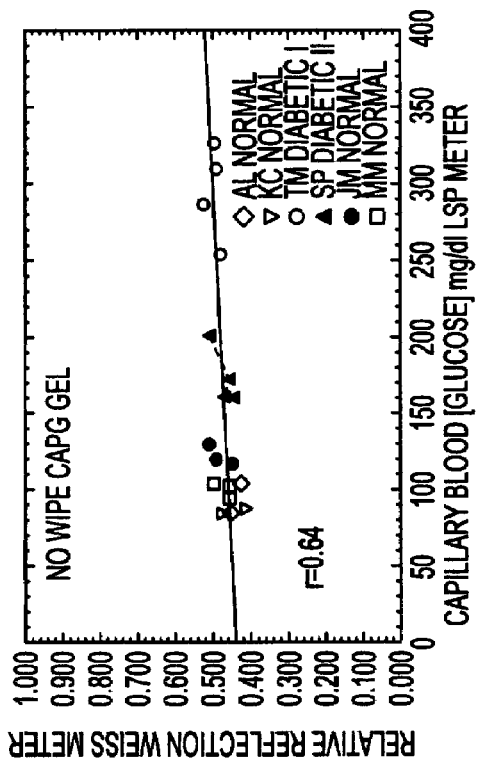
Figure 27B:
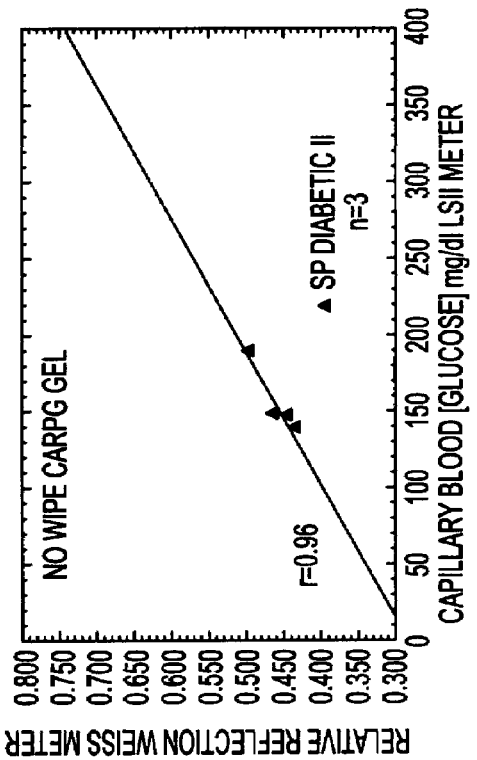
Figure 27C:
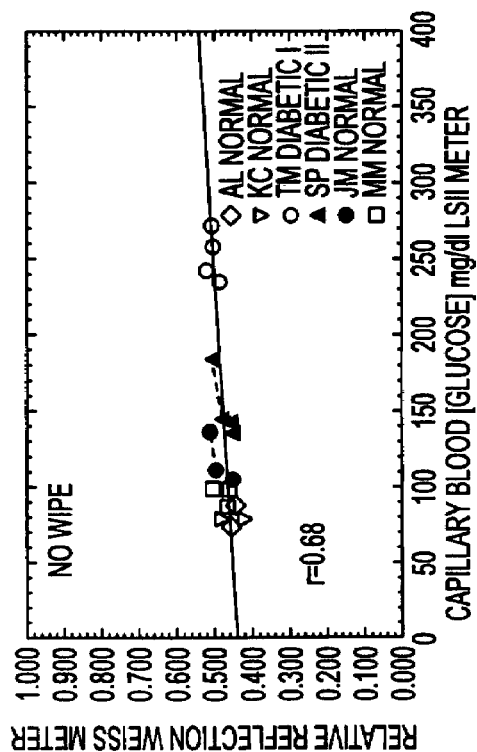
Figure 27D:
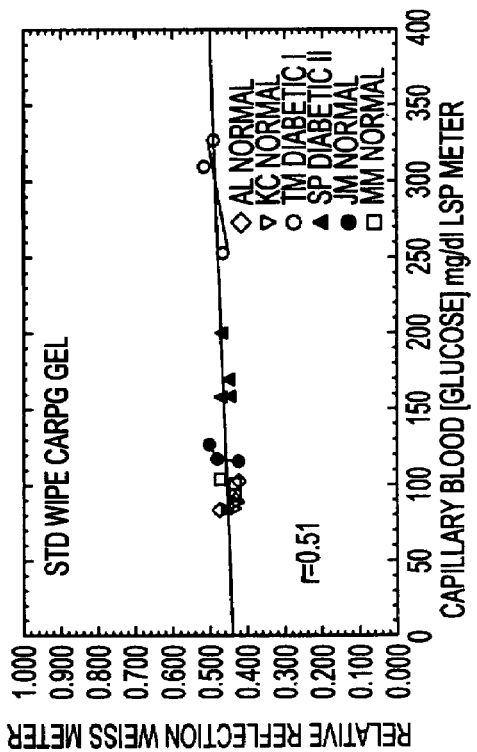
Figure 28A:
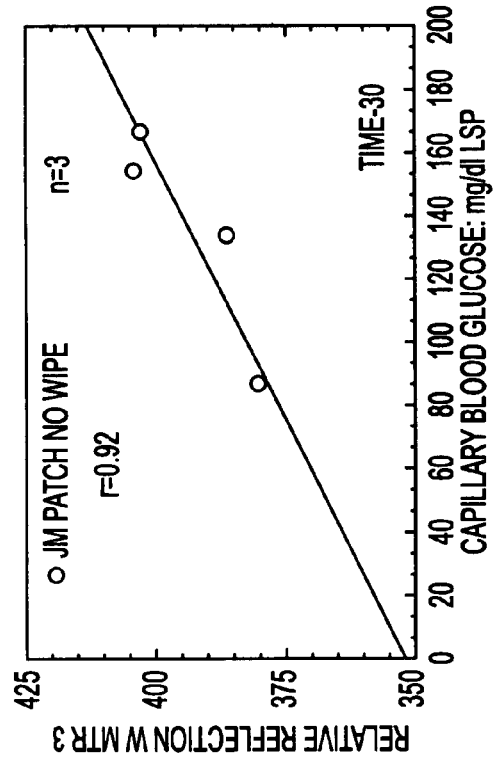
Figure 28B:
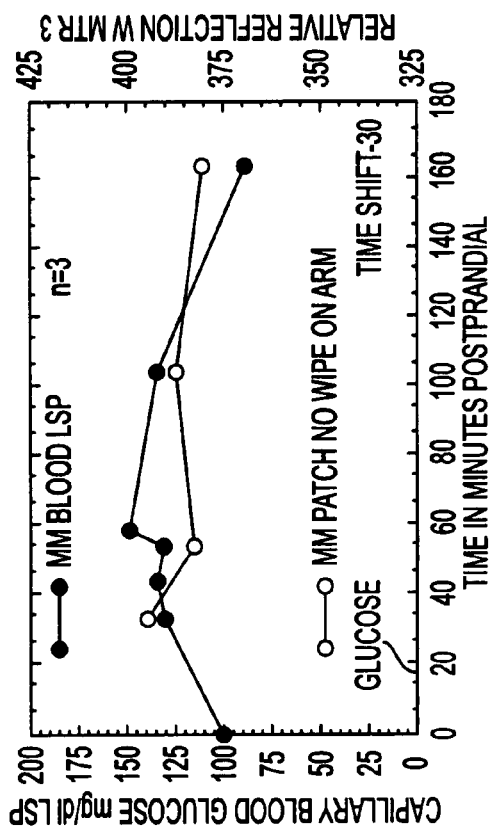
Figure 28C:
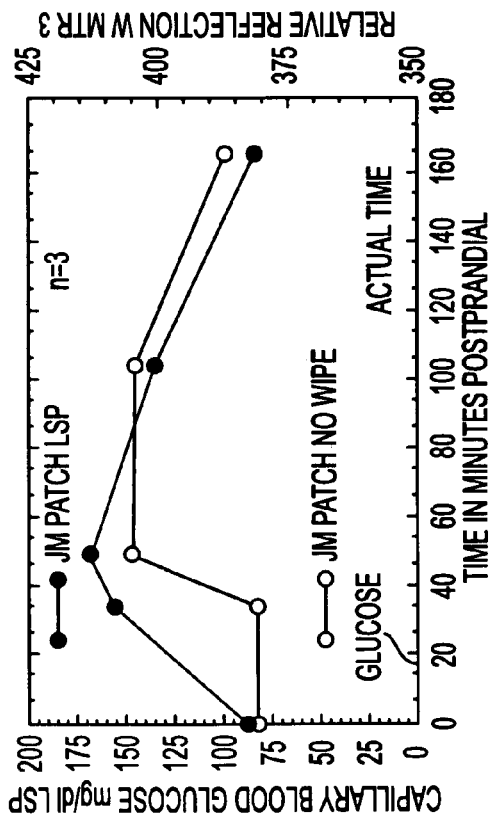
Figure 28D:
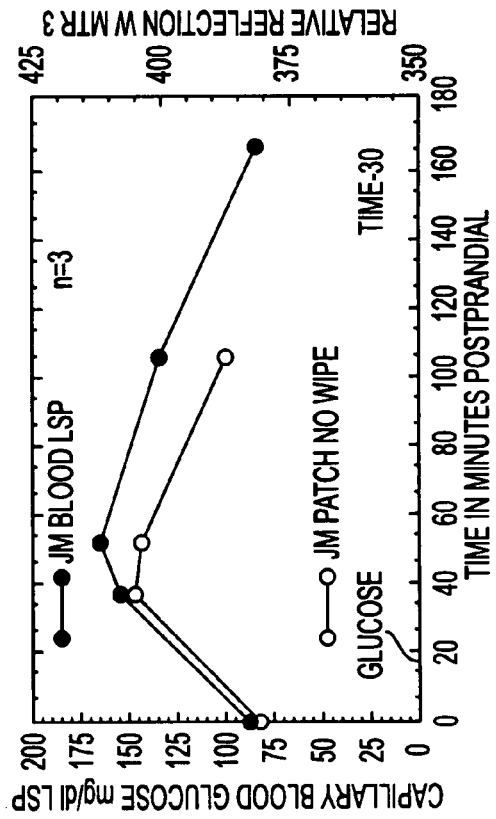
Figure 35:
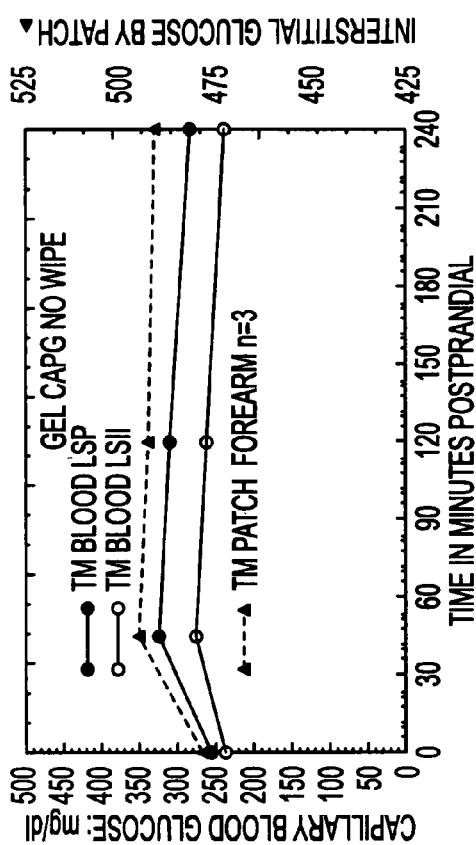
Figure 34:
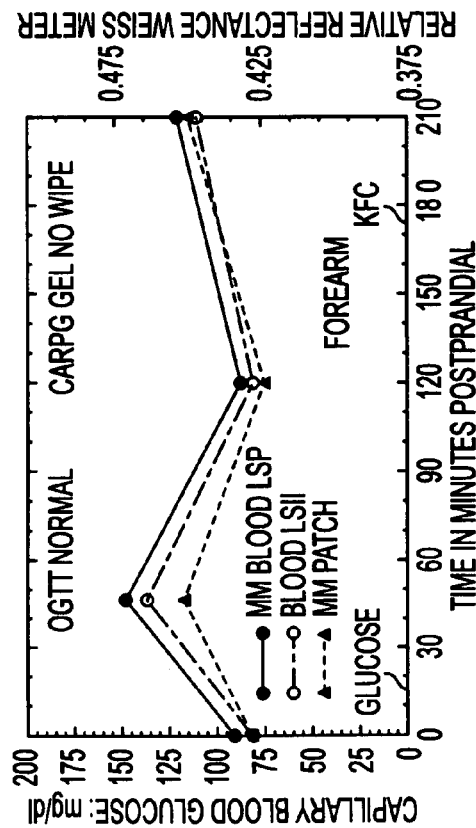
Figure 37:
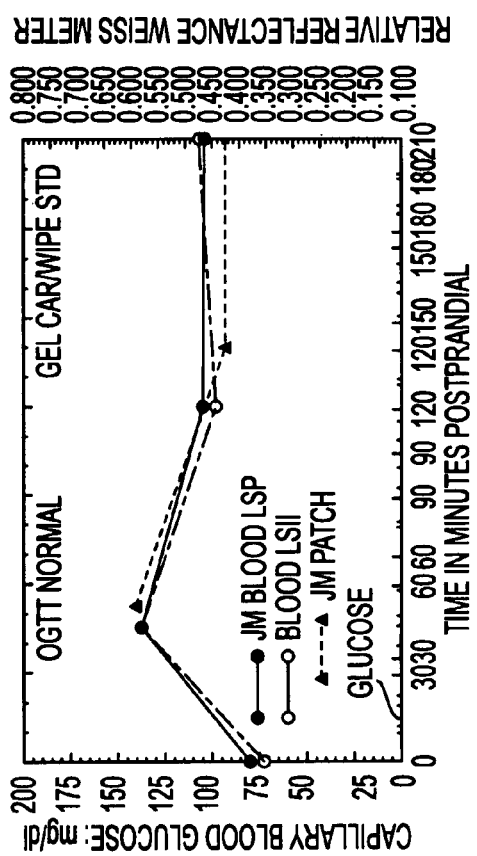
Figure 36:
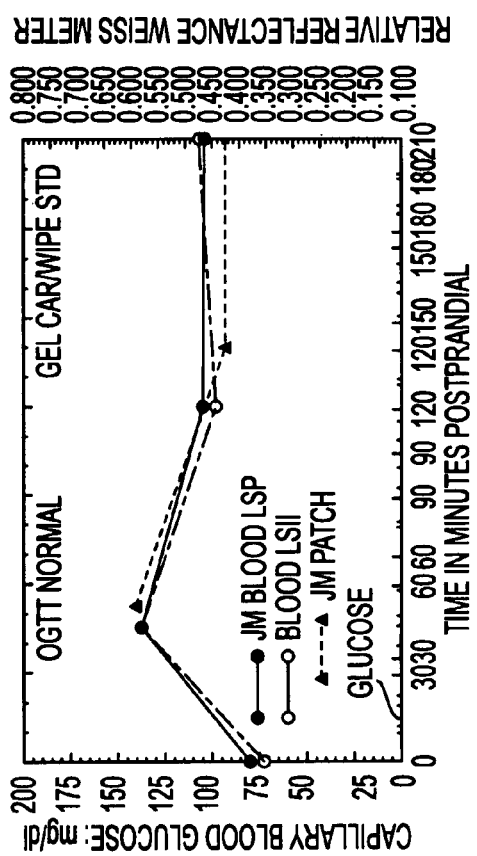
Figure 38:
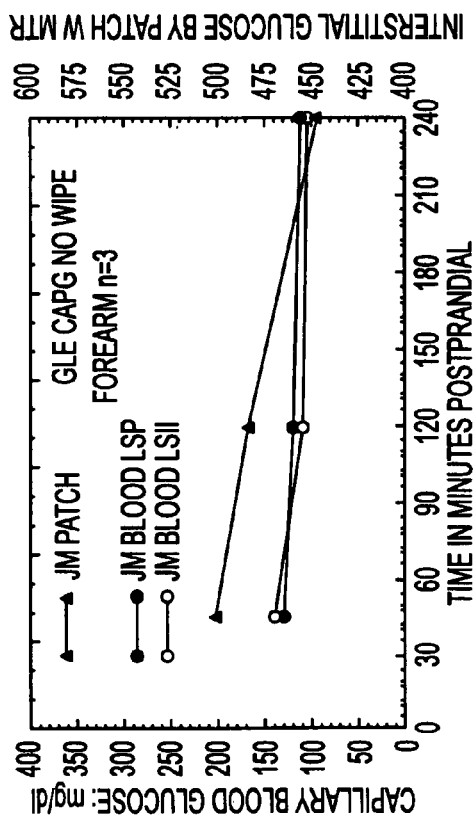
Figure 39:
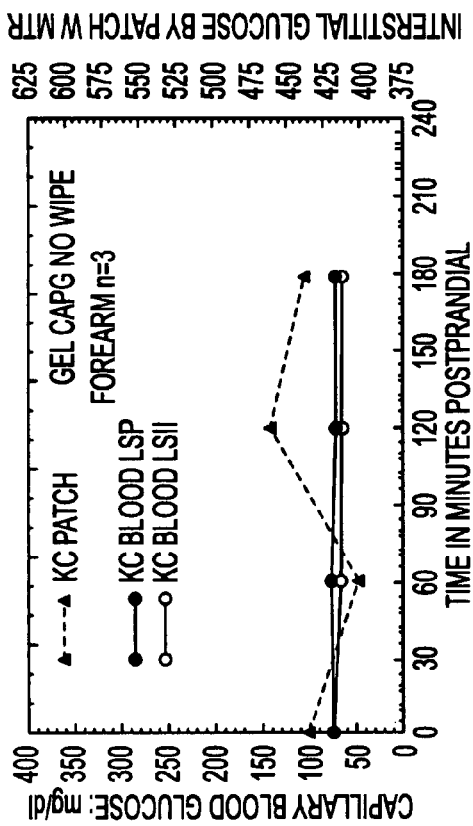
Figure 40:
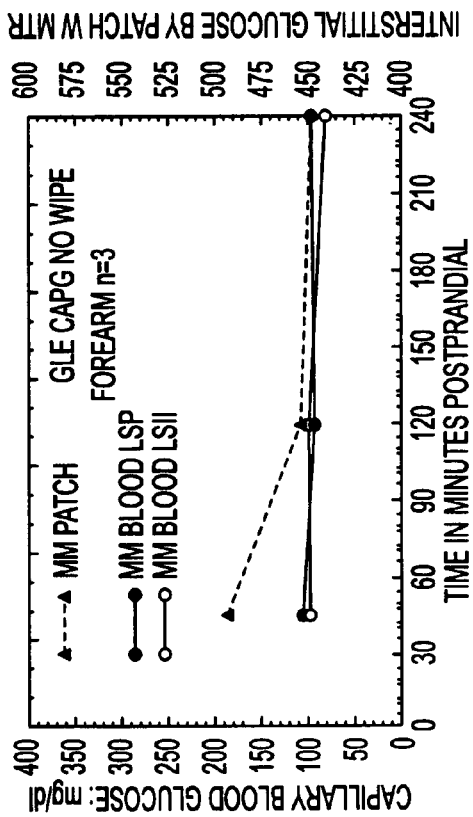
Figure 41:
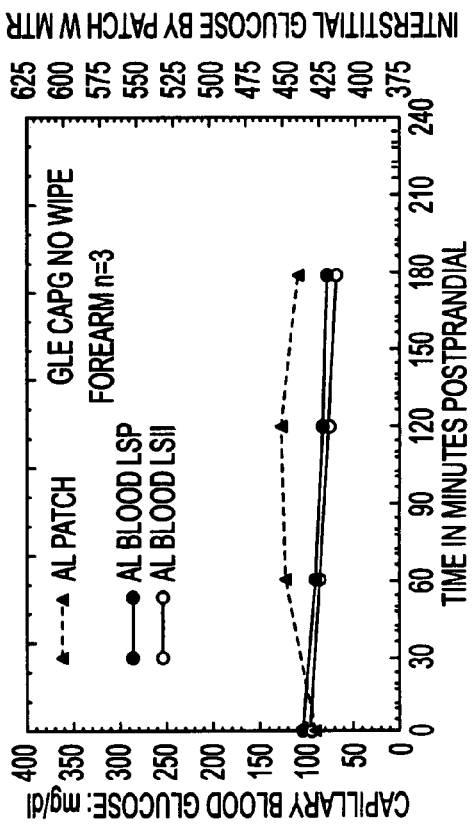
Figure 42:
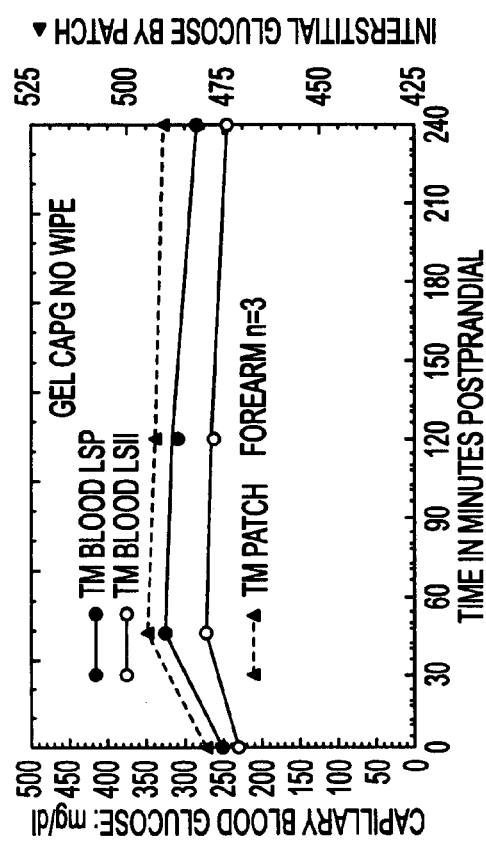
Figure 43:
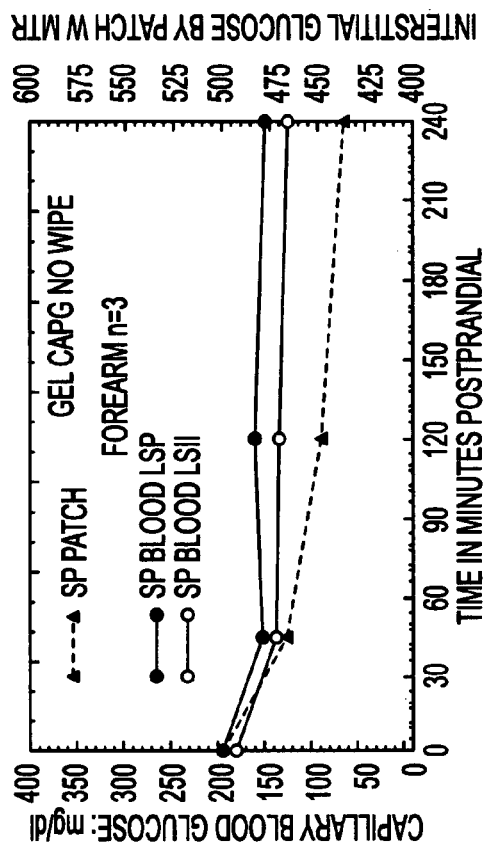
Figure 44:
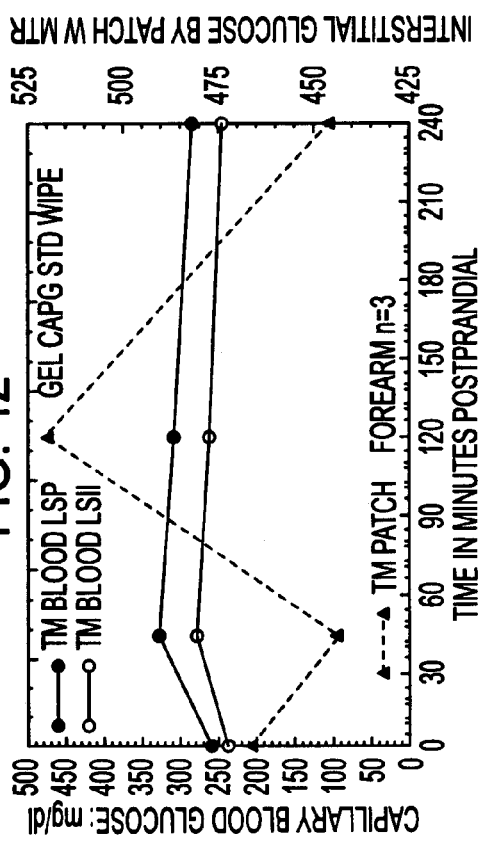
Figure 45:
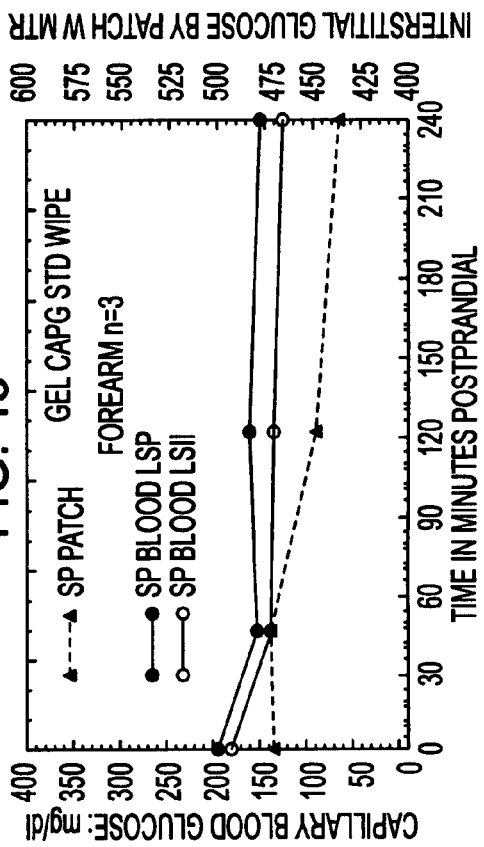
Figure 46:
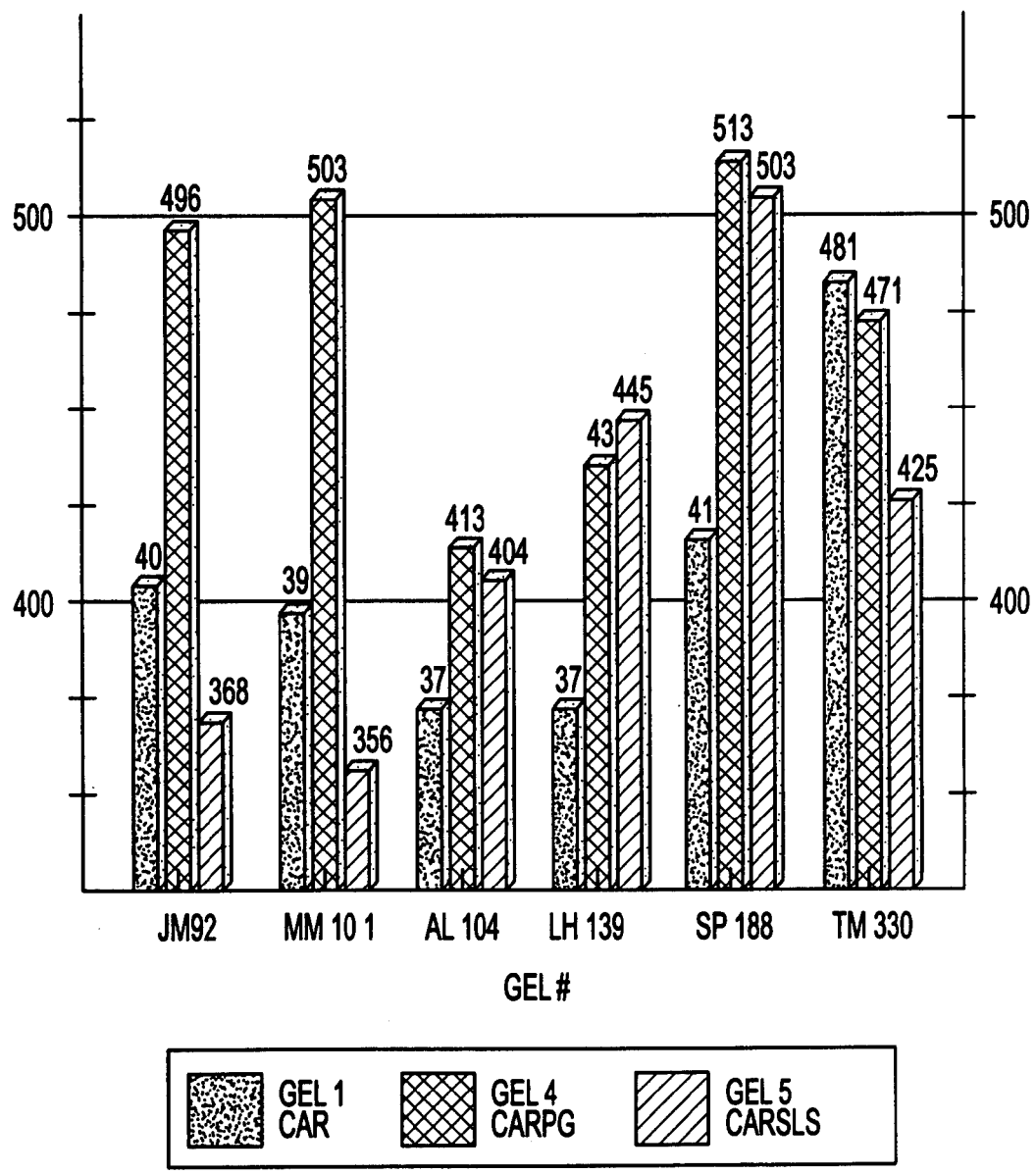
Figure 47:
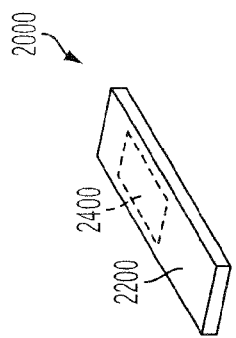
Figure 48A:
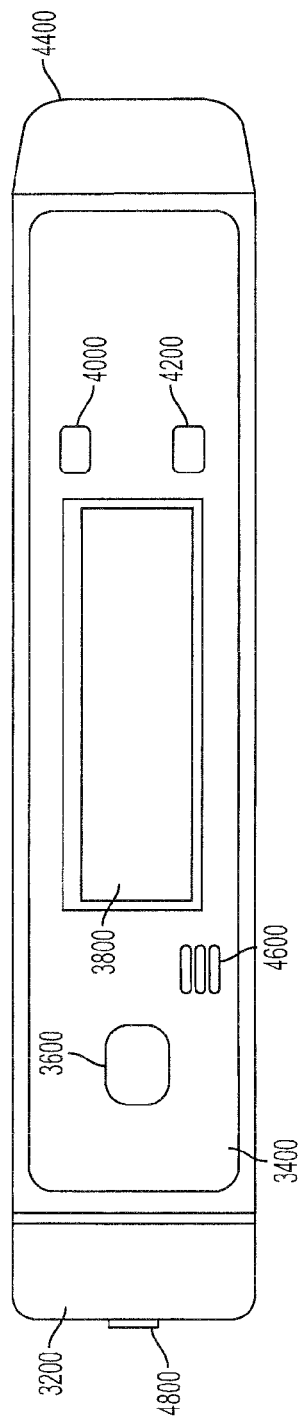
Figure 48B:
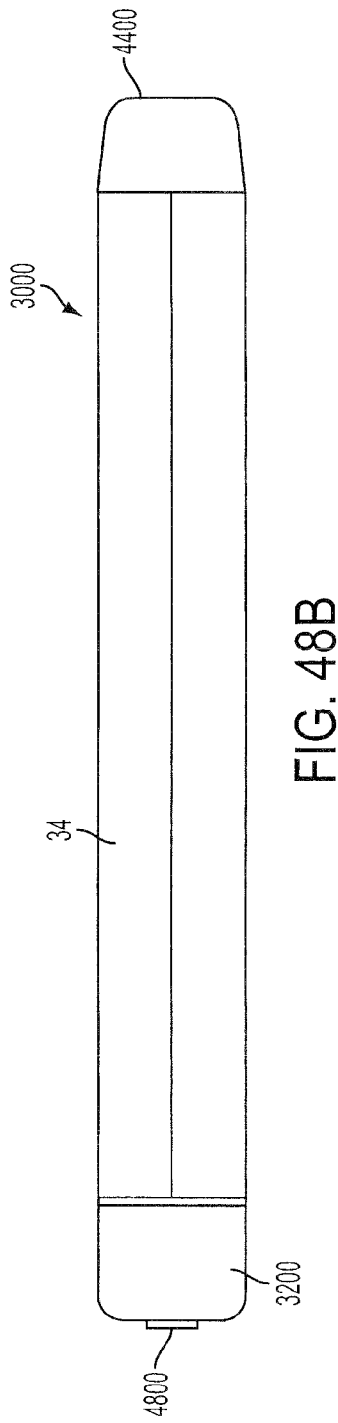
Figure 49:
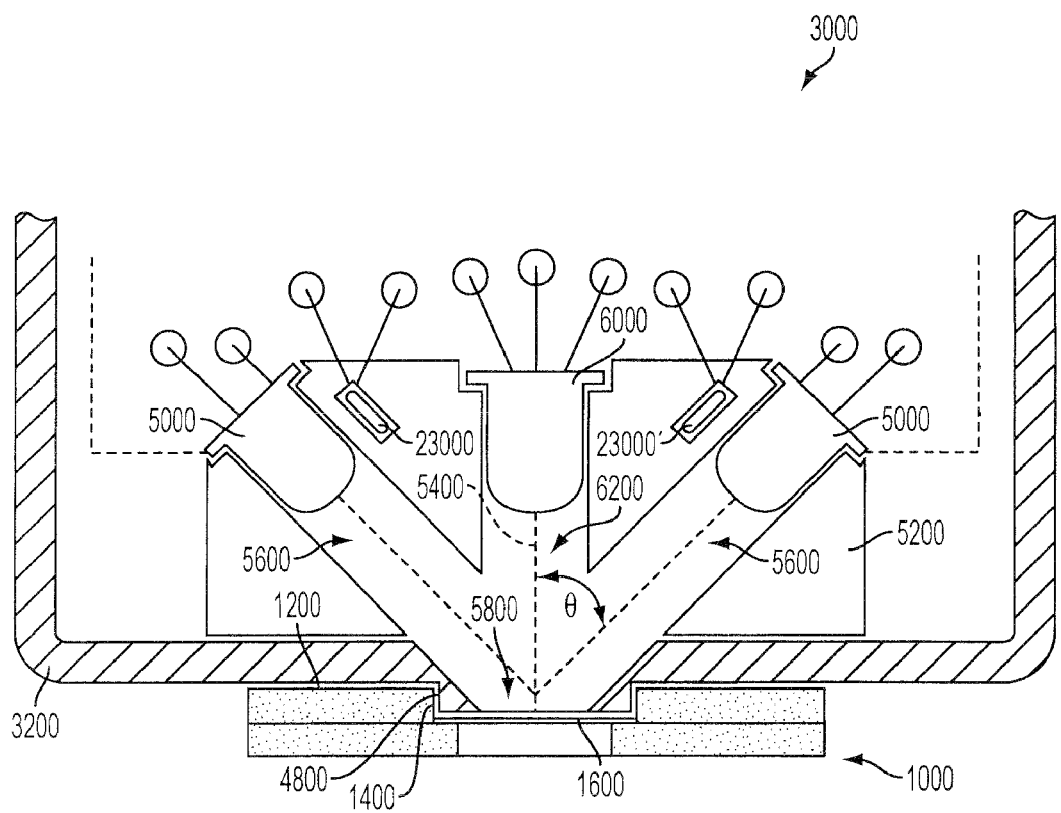
Figure 50:
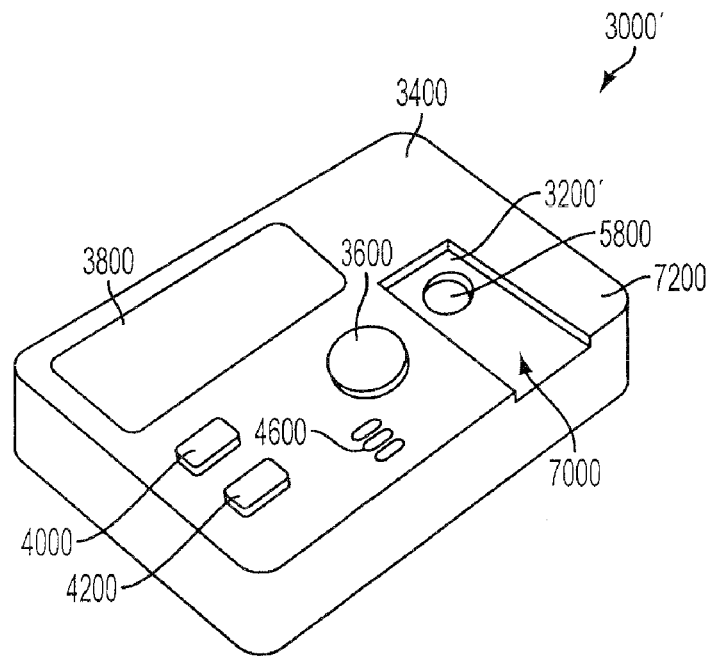
Figure 51:
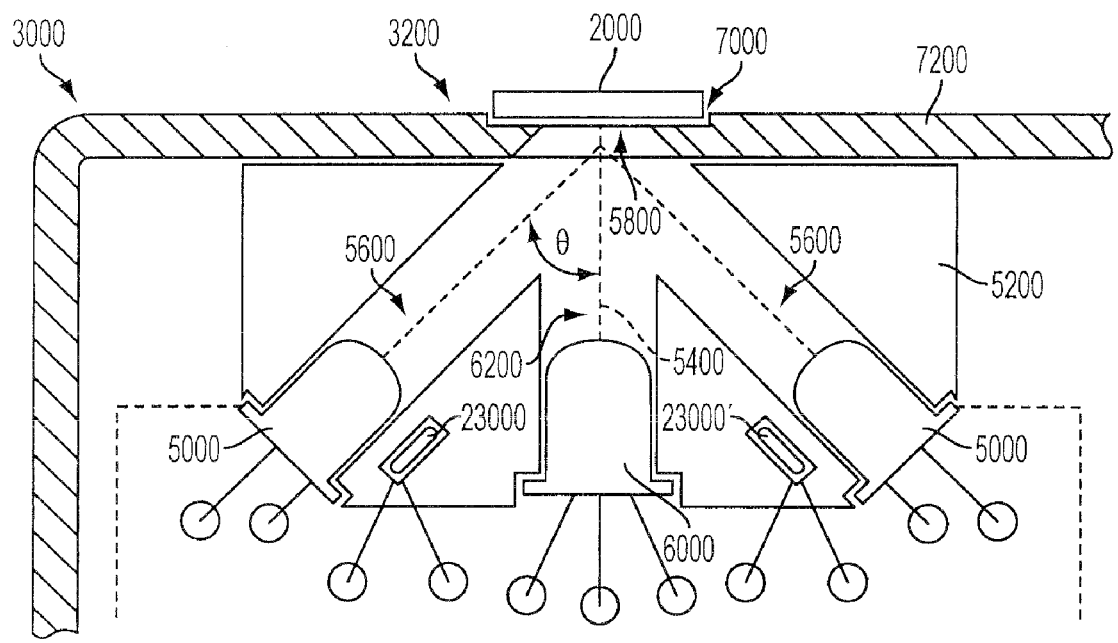
Figure 52A:
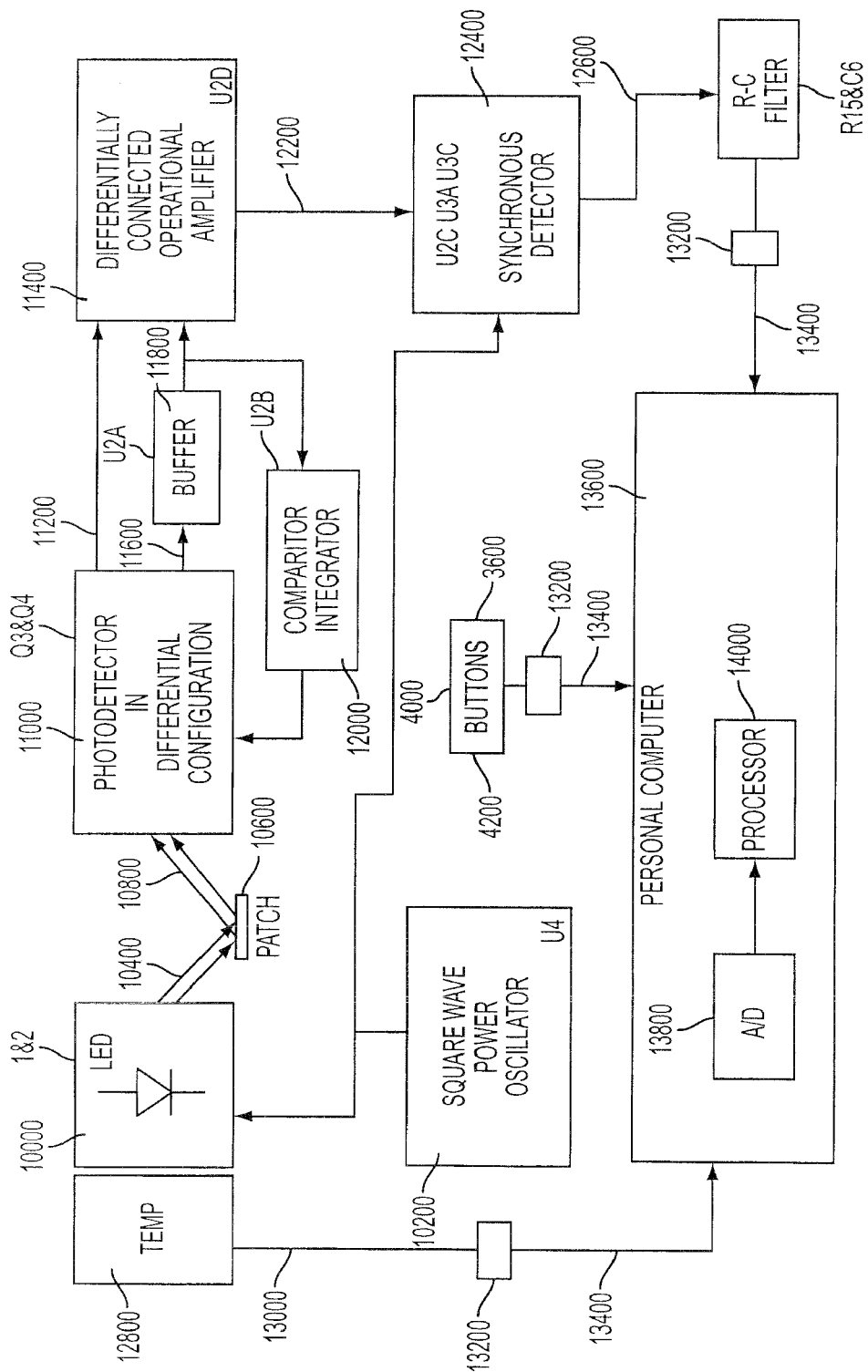
Figure 52B:
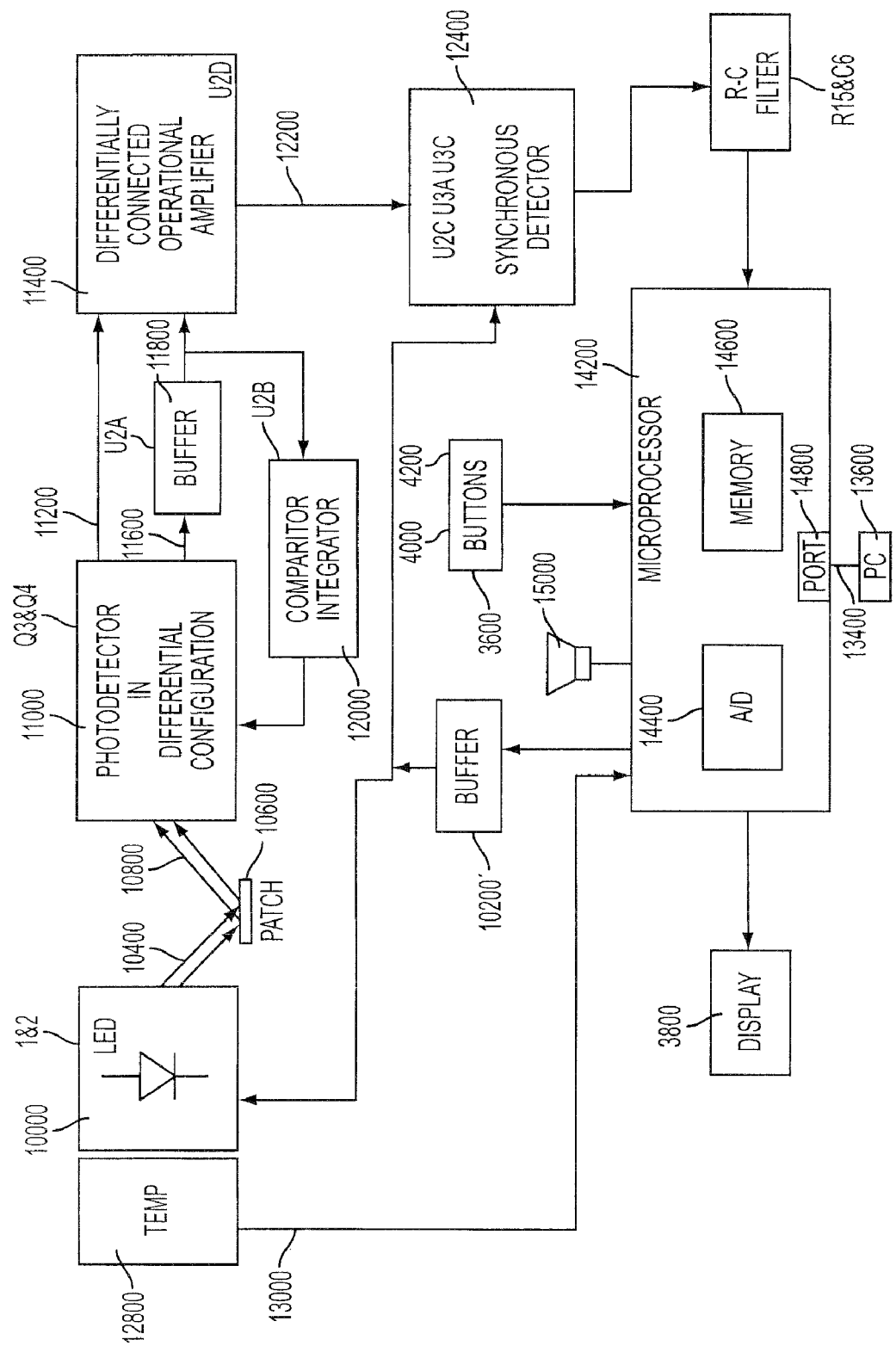
Figures 1, 53A:
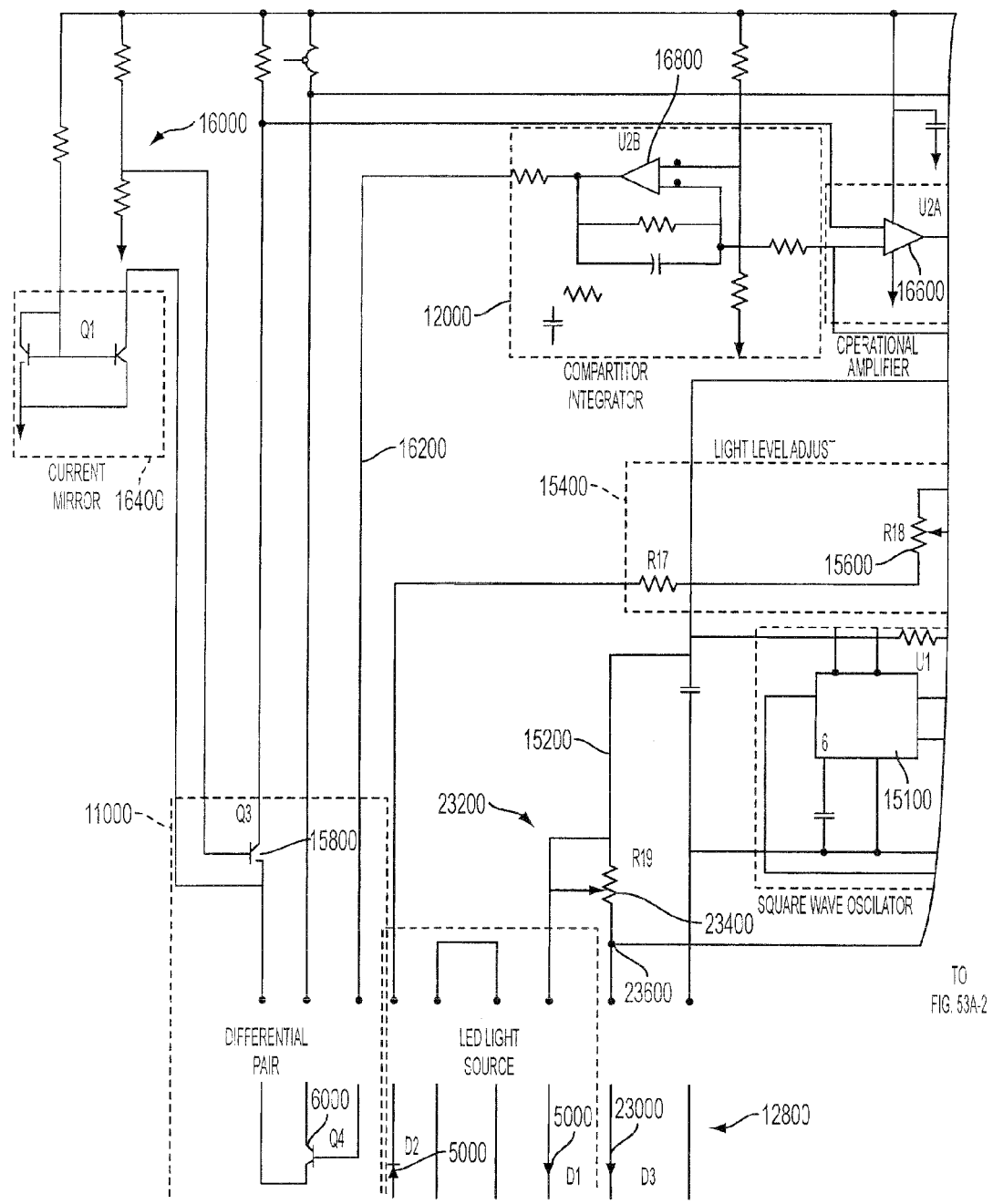
FIG. 1A is a perspective view of a noninvasive transdermal patch according to one embodiment of the present invention.
FIG. 1B is a cross-sectional view along the line 1A-1A of the noninvasive transdermal patch of FIG. 1A.
FIG. 1C is a perspective of a noninvasive transdermal patch illustrated in FIG. 1A but in a closed position.
Figures 2, 53A:
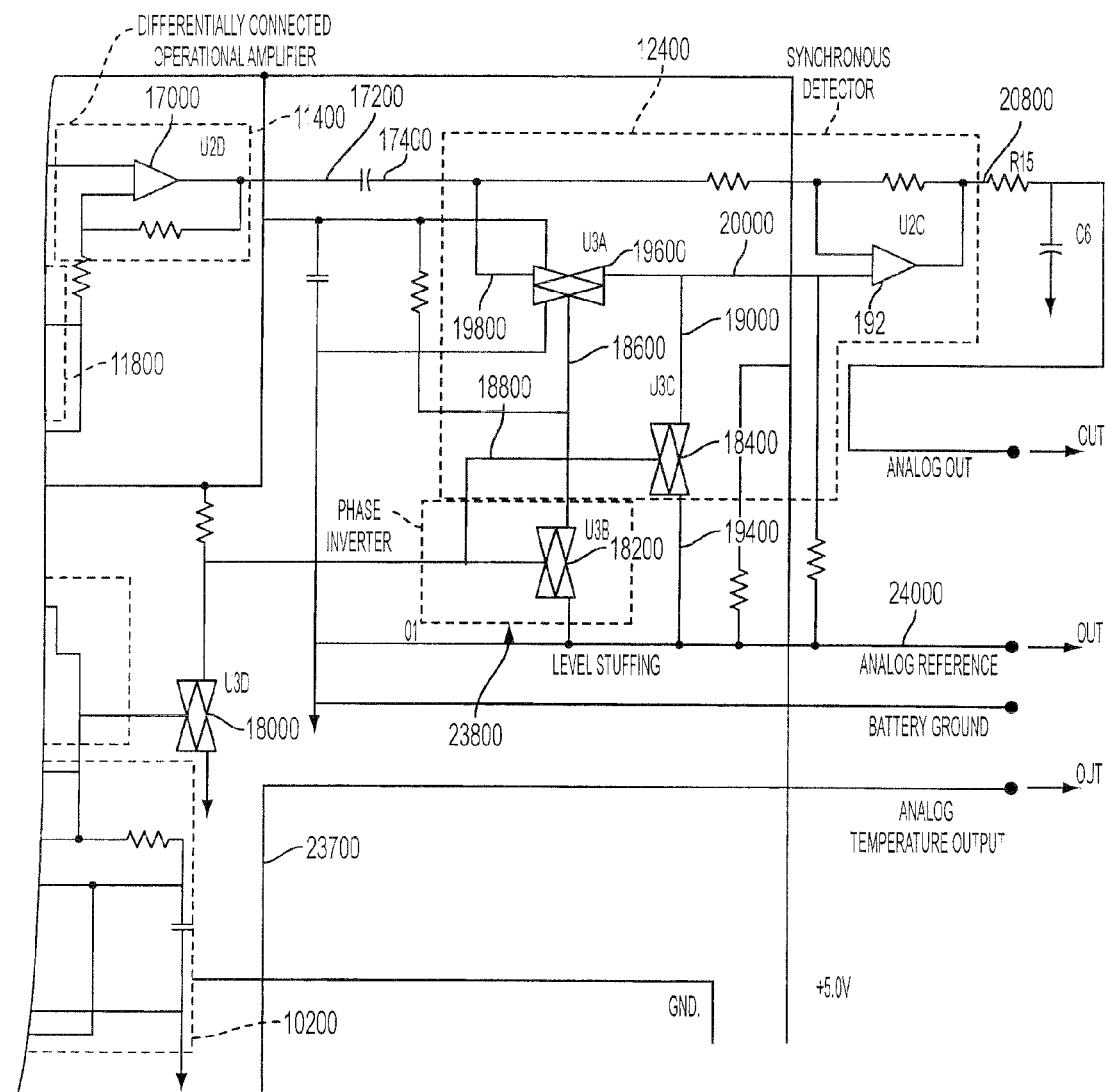
Figures 1, 53B:
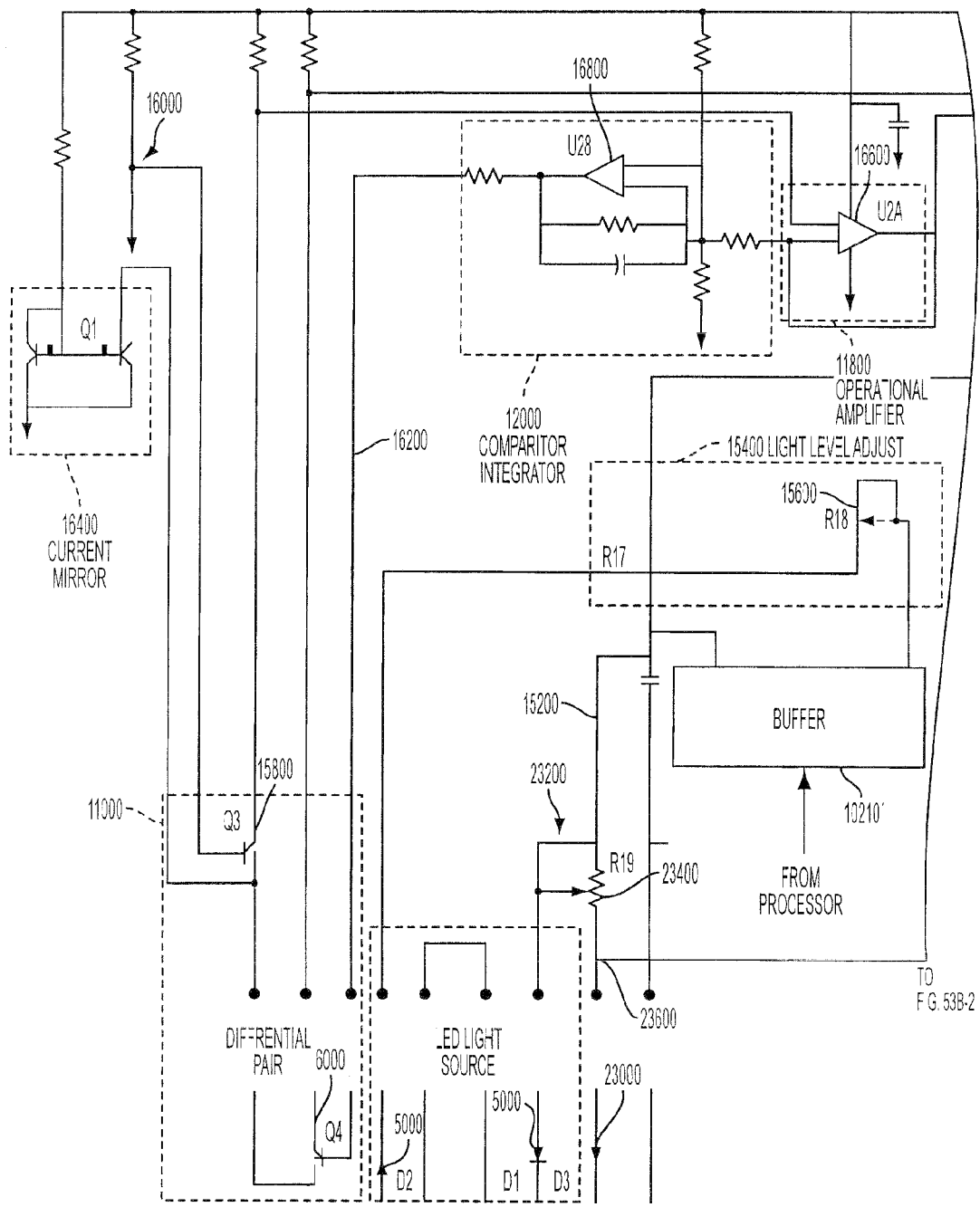
Figures 2, 53B:
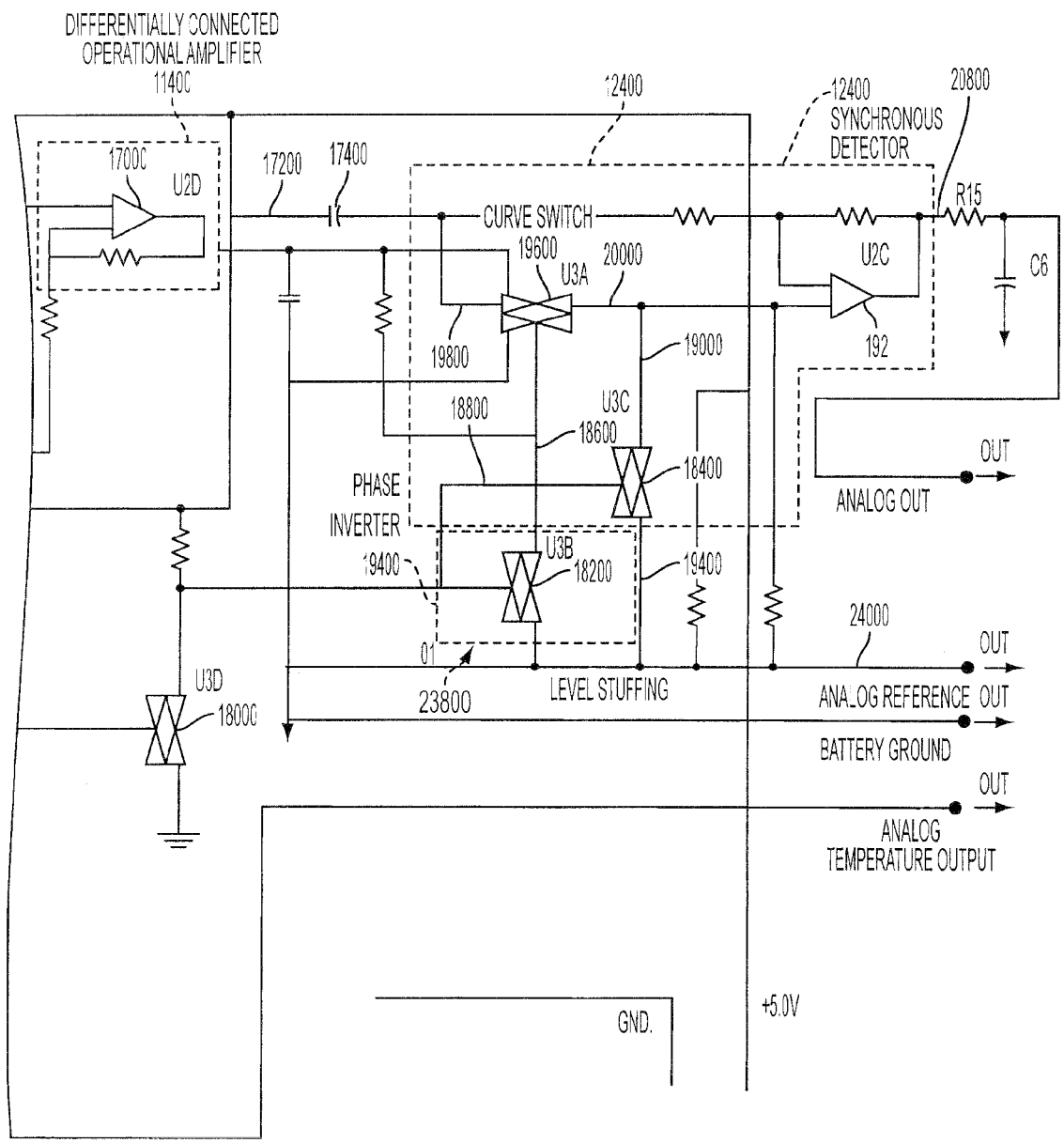
Figure 54A:
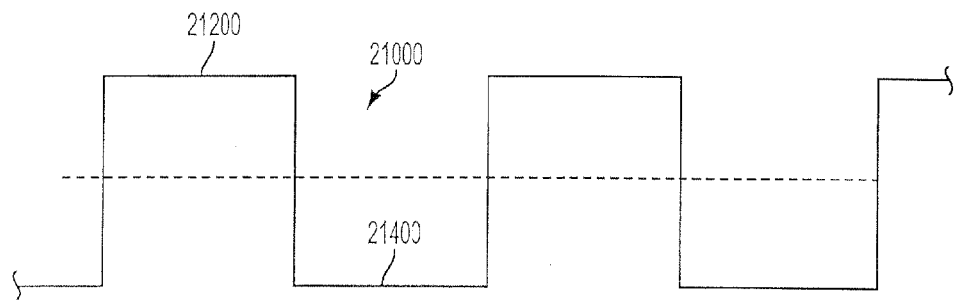
Figure 54B:
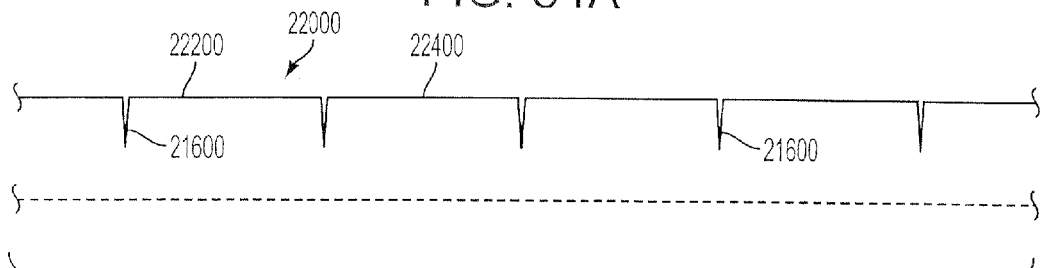
Figure 55A:
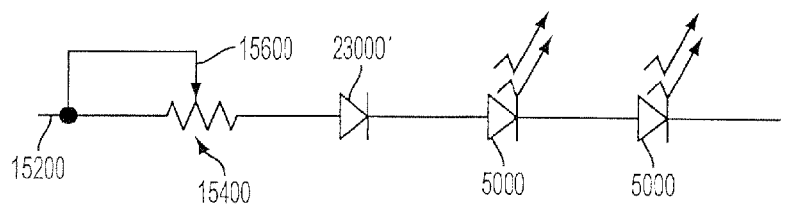
Figure 55B:
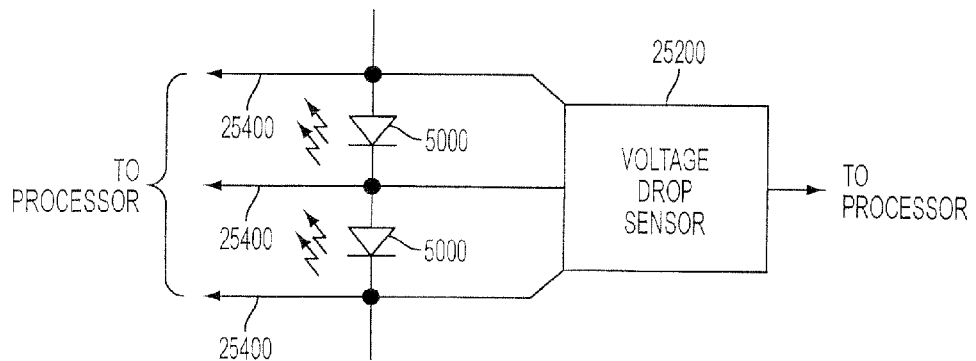
Figures 56, 57:
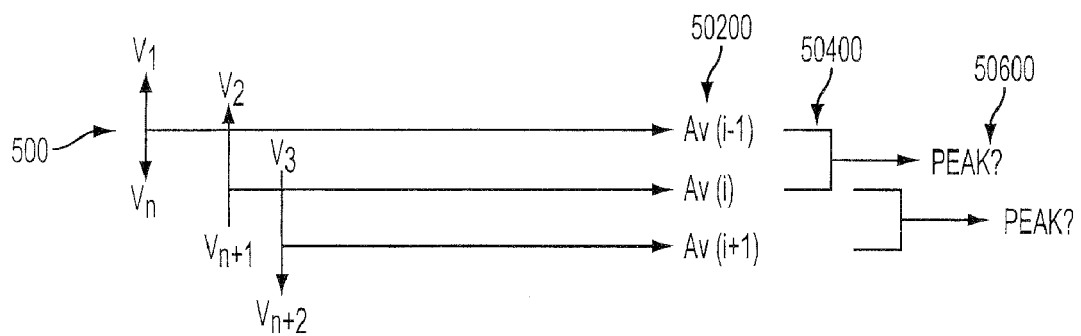
Figure 58A:
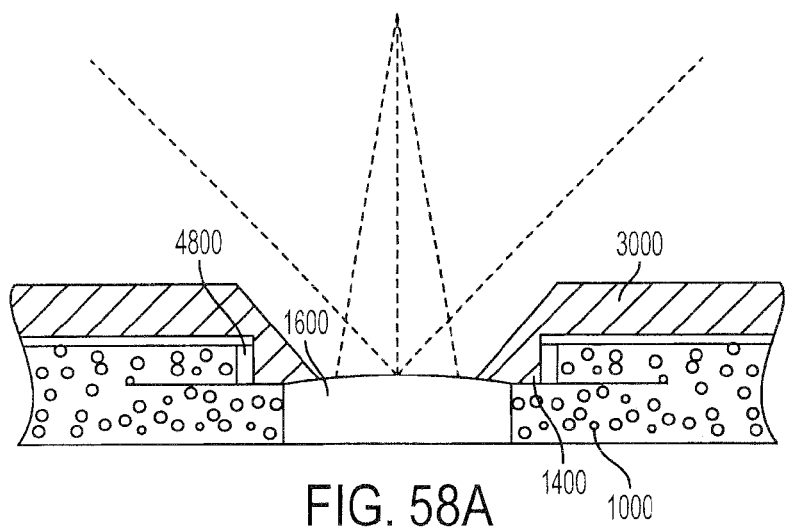
Figure 58B:
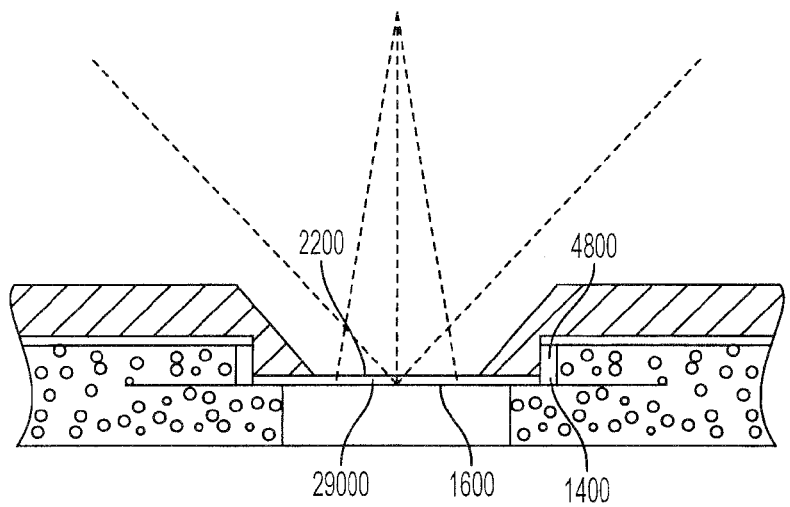
Figure 58C:
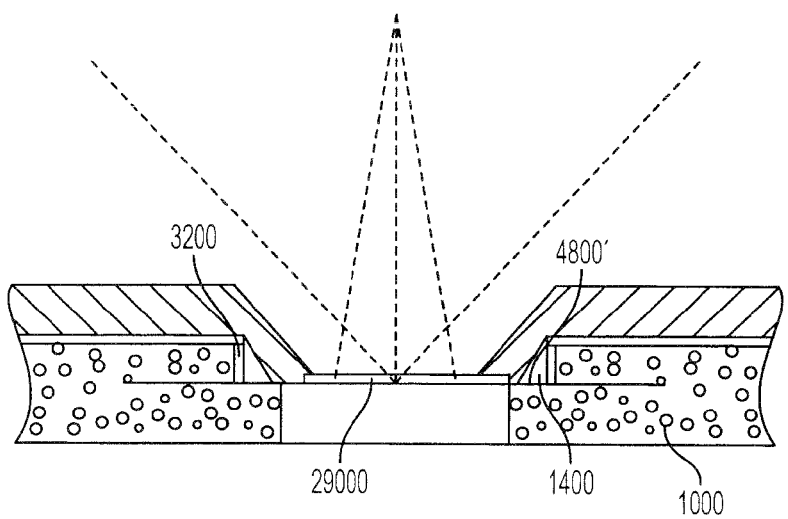
Figure 59:
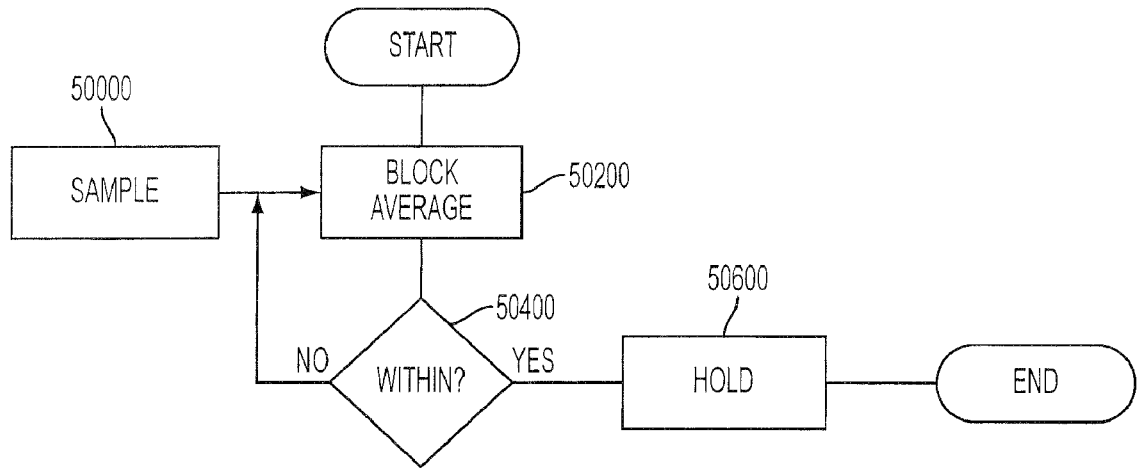
Figure 60:
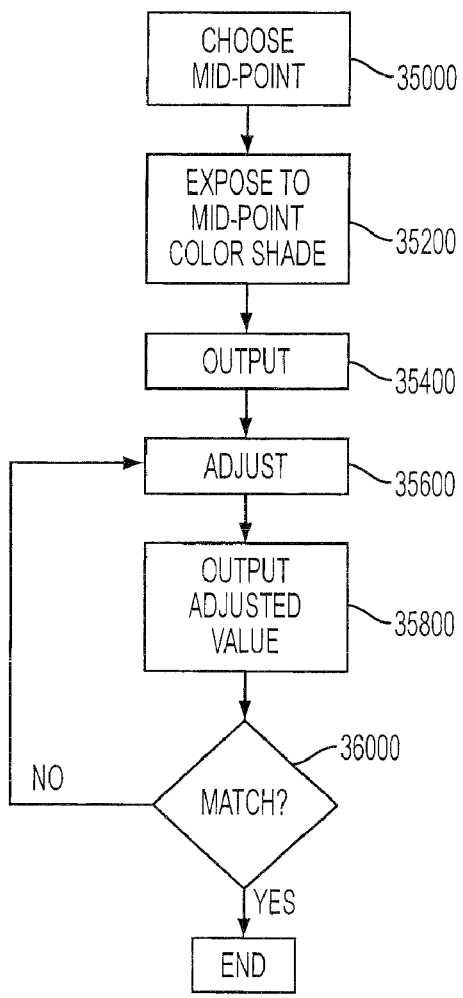
Figure 61:
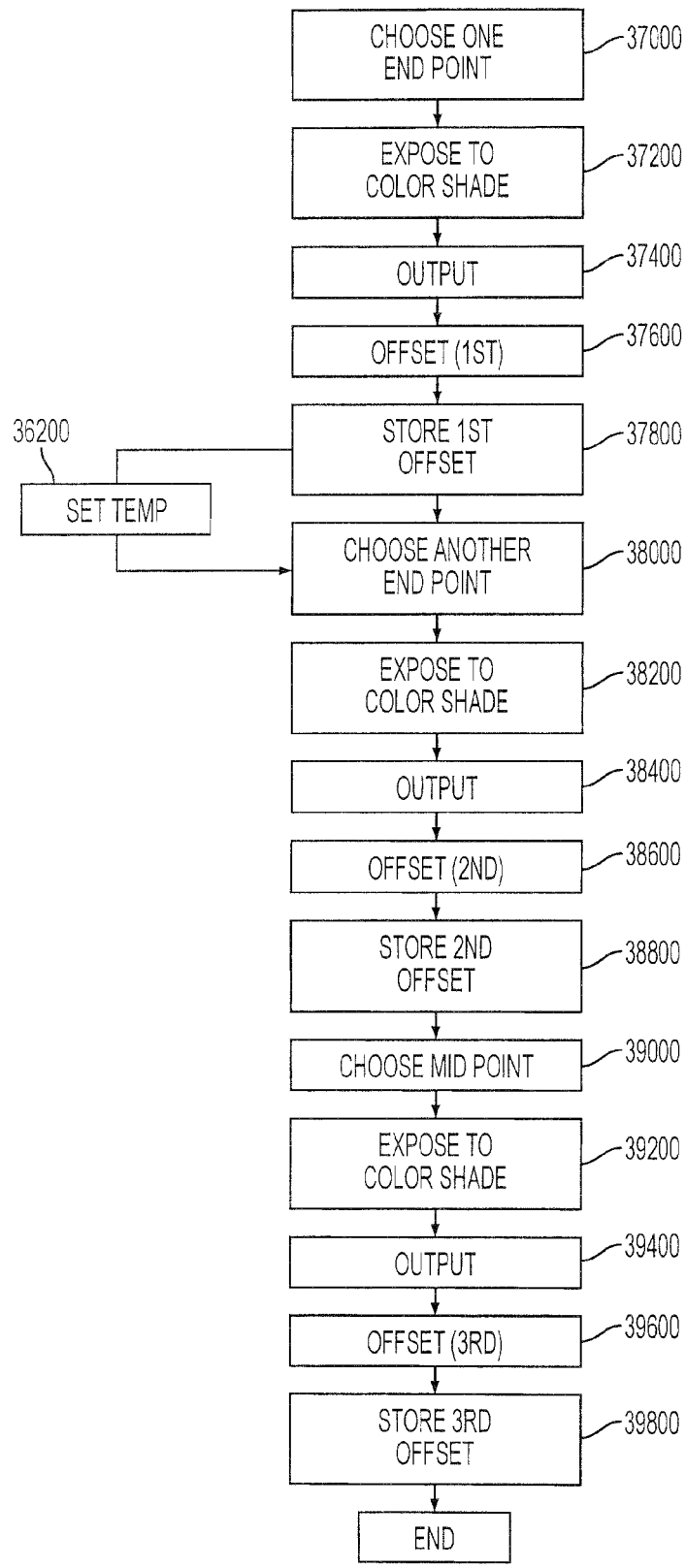
Figure 62:
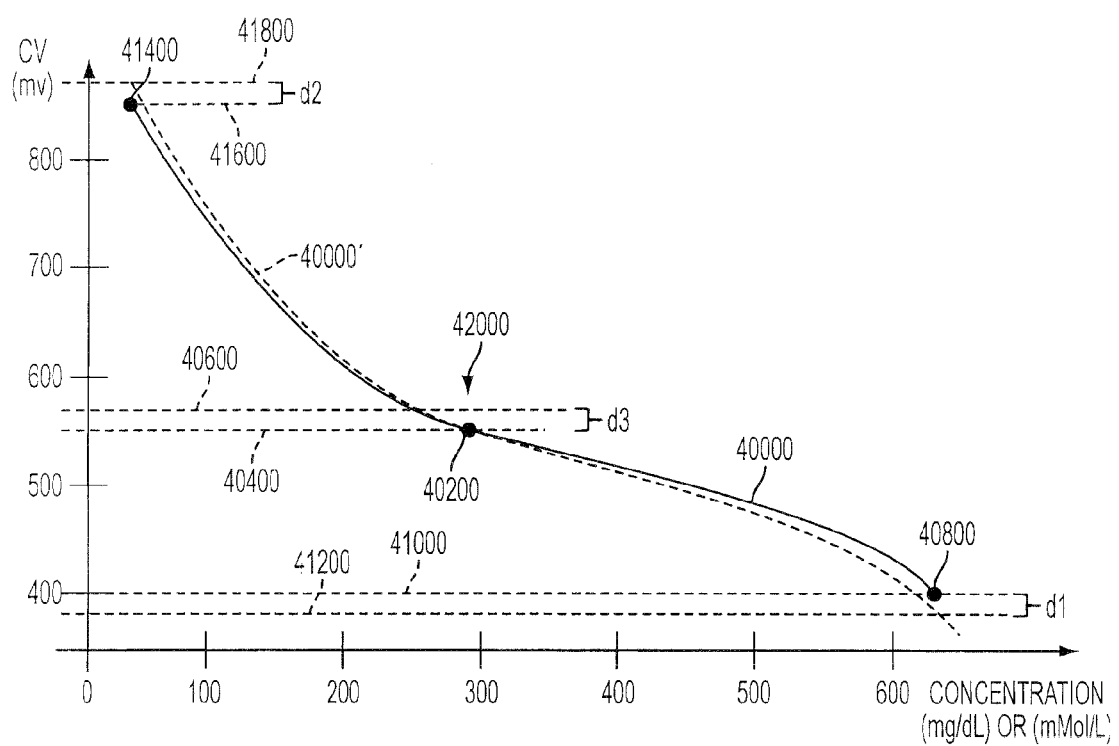
Figure 63:
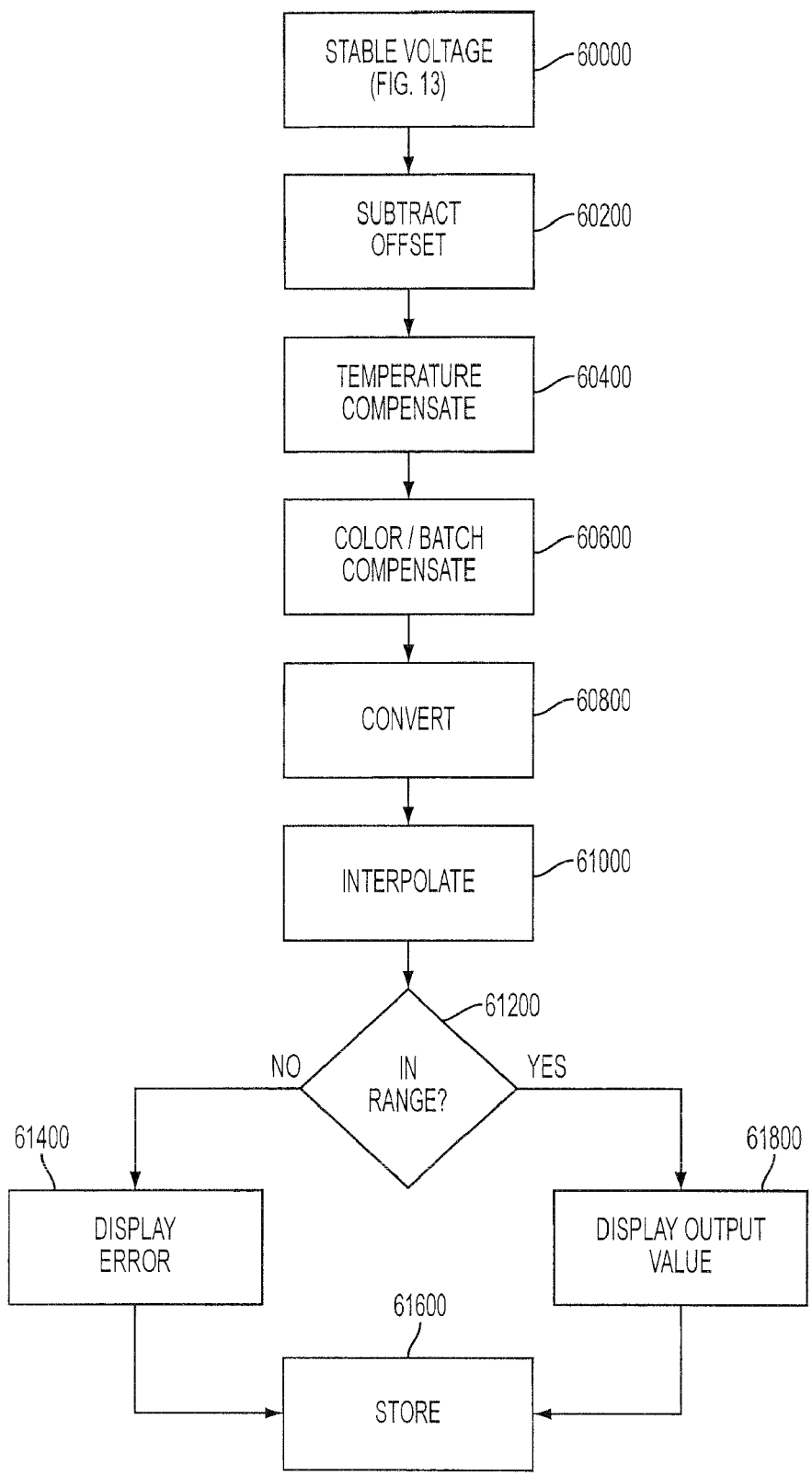

FIG. 26 describes generally a method of testing the permeation enhancing power of the skin permeation enhancer in accordance with the present invention;

FIG. 27 is a plot of data which compares the results obtained from a noninvasive transdermal patch of the present invention with results obtained from capillary blood glucose utilizing standard LSII methods;

FIG. 28 is a plot of data which compares the results obtained from a noninvasive transdermal patch of the present invention with results obtained from capillary blood glucose utilizing standard LSII methods;

FIG. 29 is a plot of data showing the sensitivity of a noninvasive transdermal glucose patch of the present invention;

FIG. 30 is a plot of data comparing results obtained from a noninvasive transdermal patch of the present invention with results obtained from blood glucose by standard method;

FIG. 31 is a plot of data comparing results obtained from a noninvasive transdermal patch of the present invention with results obtained from blood glucose by standard method;

FIG. 32 is a plot of data comparing results obtained from a noninvasive transdermal patch of the present invention with results obtained from blood glucose by standard method;

FIG. 33 is a plot of data comparing results obtained from a noninvasive transdermal patch of the present invention with results obtained from blood glucose by standard method;

FIG. 34 is a plot of data which compares the results obtained from a noninvasive transdermal patch of the present invention with results obtained from capillary blood glucose utilizing standard method;

FIG. 35 is a plot of data which compares the results obtained from a noninvasive transdermal patch of the present invention with results obtained from capillary blood glucose utilizing standard method;

FIG. 36 is a plot of data which compares the results obtained from a noninvasive transdermal patch of the present invention with results obtained from capillary blood glucose utilizing standard method;

FIG. 37 is a plot of data which compares the results obtained from a noninvasive transdermal patch of the present invention with results obtained from capillary blood glucose utilizing standard method;

FIG. 38 is a plot of data which compares the results obtained from a noninvasive transdermal patch of the present invention with results obtained from capillary blood glucose utilizing standard method;

FIG. 39 is a plot of data which compares the results obtained from a noninvasive transdermal patch of the present invention with results obtained from capillary blood glucose utilizing standard method;

FIG. 40 is a plot of data which compares the results obtained from a noninvasive transdermal patch of the present invention with results obtained from capillary blood glucose utilizing standard method;

FIG. 41 is a plot of data which compares the results obtained from a noninvasive transdermal patch of the present invention with results obtained from capillary blood glucose utilizing standard method;

FIG. 42 is a plot of data which compares the results obtained from a noninvasive transdermal patch of the present invention with results obtained from capillary blood glucose utilizing standard method;

FIG. 43 is a plot of data which compares the results obtained from a noninvasive transdermal patch of the present invention with results obtained from capillary blood glucose utilizing standard method;

FIG. 44 is a plot of data which compares the results obtained from a noninvasive transdermal patch of the present invention with results obtained from capillary blood glucose utilizing standard method;

FIG. 45 is a plot of data which compares the results obtained from a noninvasive transdermal patch of the present invention with results obtained from capillary blood glucose utilizing standard method;

FIG. 46 is a bar graph of data showing the effectiveness of different gels without the use of wipes in noninvasive transdermal glucose patches of the present invention;

FIG. 47 is a perspective views of a testing strip, which develops a color shade indicative of a detected analyte of interest presence within a patient;

FIGS. 48A and 48B are top and side views, respectively, of a hand-held reflectometer suitable for reading developed color shade on the transdermal patch of FIGS. 1A, 1B and 1C;

FIG. 49 is a cross-sectional view of the sensor head of the hand-held reflectometer shown in FIGS. 48A and 48B;

FIG. 50 is a perspective view of a desk-top reflectometer suitable for reading developed color shade on the testing strip of FIG. 47;

FIG. 51 is a cross-sectional view of the reading site of the desk-top reflectometer shown in FIG. 47;

FIGS. 52A and 52B are block diagrams of an electronic circuit for two embodiments of a reflectometer in accordance with the present invention;

FIGS. 53A-1, 53A-2, 53B-1 and 53B-2 are circuit diagrams for an analog portion of the reflectometer of the present invention as shown in FIGS. 52A and 52B, respectively;

FIGS. 54A and 54B are waveform diagrams illustrating operation of a synchronous detector of the present invention;

FIGS. 55A and 55B are circuit diagrams illustrating alternative implementations for providing temperature indicative data to a reflectometer;

FIG. 56 is a diagram illustrating an exemplary operation of the peak hold detection algorithm used in processing a signal representative of the detected light;

FIG. 57 illustrates a lookup table which correlates a certain voltage indicative of detected target surface color and shade to a certain concentration of an analyte of interest;

FIG. 58A is a cross-sectional view illustrating an improper engagement of the reflectometer sensor head and the transdermal patch due to excessive pressure;

FIG. 58B is a cross-sectional view illustrating the use of a window on the nose portion of the reflectometer sensor head to ensure accurate positioning of the reflectometer with respect to the target surface;

FIG. 58C is a cross-sectional view illustrating the use of a tapered nose portion for the reflectometer sensor head;

FIG. 59 is a flow diagram illustrating the peak hold detection algorithm used in processing a signal representative of the detected light;

FIG. 60 is a flow diagram illustrating a process for performing a first order calibration of the reflectometer;

FIG. 61 is a flow diagram illustrating a process for performing a second and third order calibration of the reflectometer;

FIG. 62 is a graph illustrating an exemplary compensated voltage-analyte concentration curve and the affect thereon of the first, second and third order calibration processes of FIGS. 60 and 61, respectively; and FIG. 63 is a flow diagram illustrating a process for converting an input voltage indicative of read color shade into a concentration value output.

DETAILED DESCRIPTION

By way of illustrating and providing a more complete appreciation of the present invention and many of the attendant advantages thereof, the following detailed description and examples are given concerning the novel methods, formulations and configurations.

Figure 2:
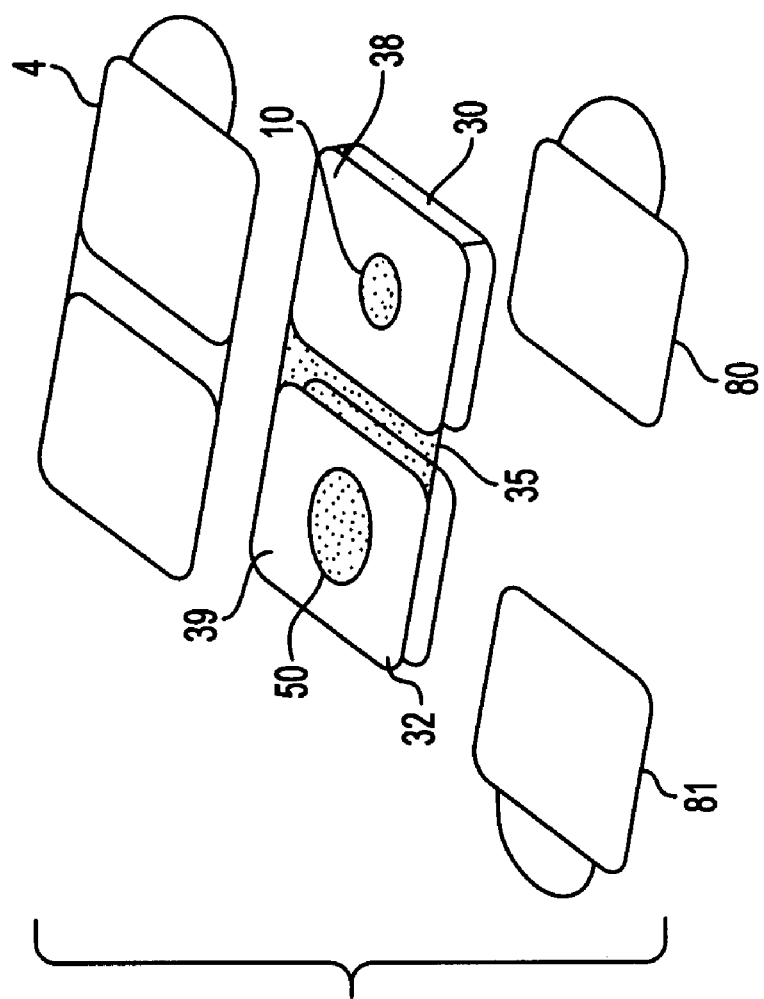
FIG. 2 is an exploded elevational view of an alternative noninvasive transdermal patch of FIG. 1A in accordance with the present invention.

Referring now to the Figs. in detail and first, particularly to FIGS. 1A, 1B, 1C and 2 thereof, there is depicted an exemplary noninvasive transdermal patch of a multi-layer composite construction in accordance with the present invention, designated generally as 1, which is in a rounded rectangle clam shell shape. The noninvasive transdermal patch 1 includes two separate housing 30, 32 and an outer pulltab layer 4 on the frontal side of device 1. Therefore, patches of similar shapes, such as rectangular-shaped patches with square corners, are likewise contemplated by the present invention. The outer pulltab layer 4 and separate housing 30 and 32 function to keep the wet chemistry component 10 and the dry chemistry component 20 separate from one another, dry and uncontaminated during non-use. The outer pulltab layer 4 also functions on the upper-outer most protective layer to which a pressure sensitive adhesive layer 5 is affixed. The outer pulltab layer 4 may be formed of an air, moisture and light barrier material, such as a pink foil supplied by 3M Pharm. under the name Scotch Pak, product number 1006 KG90008, which is about 0.010 inches thick. The adhesive layer 5 may be a pressure sensitive adhesive, such as a double coated Medium tape on liner, product number 3M 1522796A and obtained from Sunshine Tape, which is approximately 0.005 inches in thickness. Adhered to the outer pulltab layer 4 are two separate housings 30, 32, each connected by hinge 35. Housing 30 contains a through aperture 31 for receiving and maintaining the wet chemistry component 10, whereas housing 32 includes a through aperture 33 for visualizing the dry chemistry component 20, as depicted in FIG. 1B and FIG. 2. As indicated above, aperture 33 should be of such a dimension and the reading head should be so configured that they interface precisely during use to maximize the reflectometer's ability to read the color intensity to detect the analyte. In addition to receiving wet chemistry 10 in through aperture 31 of housing 30, housing 30 functions to maintain the wet chemistry component 10 in aperture 31, so that the wet chemistry component 10 remains in contact with the dry chemistry component 20 during use. In this regard, it should be appreciated that the gels of the present invention should be formulated with a gel consistency sufficient to keep the gel in the aperture 31 during storage and use and to permit the analyte to pass through to the dry membrane for detection. Thus, if the gels of the present invention are too viscous, they will interfere with detection. On the other hand, if the gels are not sufficiently viscous, they will simply leak out of and away from the patch during testing, thereby preventing detection of the analyte.

The function of through aperture 33 in housing 32 is to permit visualization of the chemical reaction based on the differential colorimetric chemistry employed for a given analyte. In addition, through aperture 33 of housing 32 functions to receive the electronic interpretation component, such as a reflectance spectrophotometer, for visualizing the test reaction based upon the differential colorimetric chemistry electronically, as indicated above. While the dimensions of through apertures 31 and 33 may be of any suitable size, an exemplary size in accordance with the present invention is about 3/16 to about 4/16 inches in diameter. Preferably, housings 30 and 32 are manufactured with a cross-linked closed cell sponge impervious to moisture. More particularly, the crosslink closed cell sponge is a polyethylene foam, 12 lb density, type A, product number GL-187 acrylic psa, supplied by 3M Pharm. Alternatively, housings 30, 32 can be made of any other suitable materials such as nylon, rubber, etc.

Affixed to each housing 30, 32 is a continuous white mylar sheet 40 via adhesive 41. A suitable white mylar sheet is Dermaflex PM 500 supplied by Flexcon Co., Inc. The Dermaflex PM 500 is a white mylar sheet coated with TC200 to make it more printable and adhesive #525. Sandwiched between white mylar sheet 40 and housing 32 is a dry chemistry membrane 20. Adjacent the surface of white mylar membrane 40 and in contact with the dry chemistry membrane 20 is adhesive #525 of the Dermaflex PM 500 mylar sheet material. The Dermaflex PM 500 white nylon sheet is also coated on both sides with adhesive #525. White mylar sheet 40 is of a thickness of about 0.05 inches including the 50K6 liner. The white mylar sheet 40 is equipped with through apertures 55 and 56. Through apertures 55 and 56 permit the wet chemistry component 10 to be in continuous contact with the dry chemistry membrane 20 when housings 30 and 32 are folded together at hinge 35, as depicted in FIG. 3A. Affixed to the dorsal side 41 of white mylar sheet 40 is a bottom pull cover 70. Bottom pull cover 70, like outer pulltab layer 4, is formed of a similar pink foil which also functions as an air, moisture and light barrier.

To use the noninvasive transdermal patch 1, as depicted in FIGS. 1A, 1B and 1C, the subject preferably first cleans the area of skin to which the test patch device is to be applied. The skin may be cleansed with, for example, deionized water by rinsing. Once the area of skin is properly and thoroughly cleansed and dried, a skin permeation enhancer may be directly applied to the cleansed area. As indicated hereinabove, however, if a skin permeation enhancer is embodied into the wet chemistry component 10, it is not necessary to also apply a skin penetrator to the skin. Before applying the noninvasive transdermal patch 1 to the cleansed skin area, both outer pulltab 4 and bottom pulltab cover 70 are removed. Once outer pulltab 4 and bottom pulltab cover 70 are removed, housings 30 and 32 are folded along hinge 35, so that dorsal surfaces 36, 37 of housings 30, 32, respectively, are brought into direct contact with one another, so that the wet chemistry component 10 is now in contact with the dry chemistry membrane 20, as depicted in FIG. 1C, to ensure continuous and uniform wetting of the dry chemistry component or super sensitive or conditioned membrane 20. In other words, through aperture 31 of housing 30 and through aperture 33 of housing 32 are now in perfect alignment. Frontal surface 38 of housing 30 is then directly applied to the cleansed skin area, so that the wet chemistry component 10 is in constant contact with the cleansed skin area during testing for transferring the analyte from the biological fluid within or underneath the skin, such as the interstitial fluid, to the drychemistry membrane 20 for chemical reaction indicator molecular formation and analyte detection. While depicted in FIG. 1A, 1B or 1C, frontal surface 38 may include a pressure sensitive adhesive for adhering the patch to the skin during testing.

Exemplary dimensions of the noninvasive transdermal patch 1, when in a folded operable condition as depicted in FIG. 1C, are as follows. The width is approximately 0.750 inches and the length is about 0.75 inches, the diameter of the through apertures 31, 33 is between about 0.1875 and 0.25 inches, and the height or thickness is about 0.125 inches.

Alternatively, the rounded rectangle clam shell shaped noninvasive transdermal patch 1 may further include bottom and top pulltabs 80, 81, respectively, sandwiched between the outer pulltab layer 4 and frontal surface 38 of housing 30 and frontal surface 39 of housing 32 as depicted in FIG. 2. When such top and bottom pulltabs 80, 81 are utilized, the sequence of events during use is as follows. Following skin cleaning, the outer pulltab layer 4 and the bottom pulltab cover 70 are removed as before. However, the bottom pulltab 80 is then removed and frontal surface 38 of housing 30 is applied to the cleansed skin area. After a period of time of about 3 to about 15 minutes, top pulltab 81 is removed and the formal indicator molecule (color change) is observed either visually by the user or by an electronic detector component to confirm the presence of the analyte, as described herein before. The bottom and top pulltabs 80, 81 may also be made of a similar white mylar sheet material as membrane 40 referenced above.

While the patches depicted in FIGS. 1A, 1B and 1C are rectangular in shape with rounded corners, the patches of FIGS. 1A, 1B and 1C are exemplary of patches contemplated by the present invention.

While there is no set length of time which the noninvasive transdermal test patch devices of the present invention must be applied, it is generally believed that a time of about 3 to about 15 minutes, and preferably from about 4 to 6 minutes, and most preferably about 5 minutes is believed to be sufficient to develop proper analyte transfer and reaction for reliable detection and quantification. Moreover, while the noninvasive transdermal patches of the present invention can be applied to any suitable skin area from which an analyte of interest can be extracted from a biological fluid within or underneath the skin, such as the arms, under arms, behind ears, legs, inside portions of legs, fingertips, torso, etc., it is preferable to place the noninvasive transdermal patches on an area of skin free of hair, such as on the forearms and, in particular, the right or left volar portions of the forearm.

Figure 3:
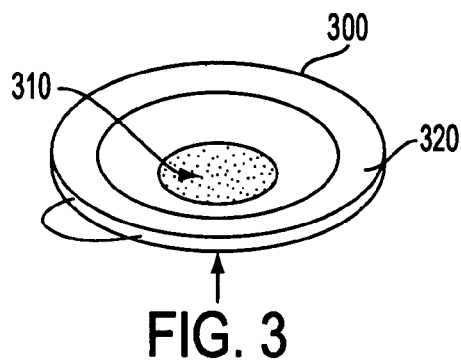
FIG. 3 is a perspective view of a noninvasive transdermal patch according to yet another embodiment of the present invention.

Configurations depicted in FIGS. 2-8 constitute further alternative exemplary embodiments of noninvasive transdermal patches of the present invention. For example, FIG. 3 depicts a round-shaped flat patch comprising an outer shell 300 comprised of a dry chemistry membrane 310 shown in the center of housing 320. The dry chemistry component 310 is a membrane saturated with a chemical reagent system for interaction and detection of an analyte of interest. In use, the targeted skin area is precleansed and then optionally treated with a skin permeation enhancer. Flat patch 300 is then removed from its foil packaging with desiccant (not shown) and a selected wet chemistry gel component (not shown) is applied on the back of membrane 310, which is then applied to the pretreated skin area for a sufficient period of time to enhance analyte transfer from the biological fluid within or beneath the skin to the dry chemistry membrane 310 for analyte detection.

Figure 4:
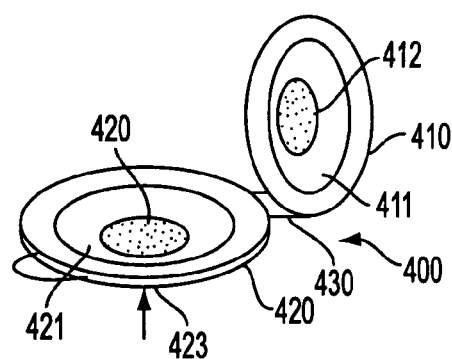
FIG. 4 is a perspective view of a noninvasive transdermal patch according to another embodiment of the present invention.

FIG. 4 depicts yet another example of a noninvasive transdermal patch in accordance with the present invention. In FIG. 4, a clam shell patch 400 is disclosed which includes a top housing 410 and a bottom housing 420. Top housing 410 contains the dry chemistry membrane 412 and bottom housing 420 contains the wet chemistry component or gel 422. Housings 410 and 420 are preferably connected by hinge 430 and each includes a concave interior surface 411 and 421, respectively, which complement one another. In use, the targeted skin area is precleansed and optionally treated with a skin permeation enhancer. Following skin pretreatment, the cover (not shown) is removed from the clam shell patch 400 and it is closed, so that the dry chemistry membrane 412 is in now contact with the wet chemistry component or gel 422 to ensure continuous and uniform wetting of the dry chemistry membrane 411. The bottom 423 of wet chemistry component or gel 422 is then applied to the pretreated skin area for sufficient time to permit interaction between the analyte under investigation and the chemical reagent system saturated on the dry chemistry membrane 412 for analyte detection.

Figure 5:
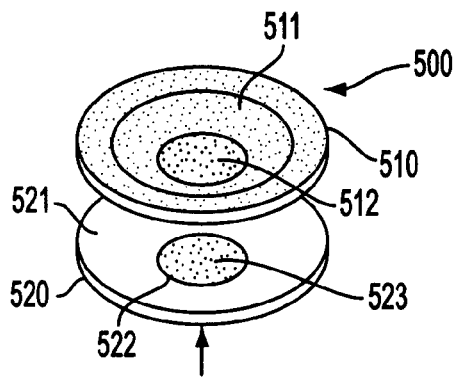
FIG. 5 is an exploded elevational view of a noninvasive transdermal patch according to yet another embodiment of the present invention.

Turning now to FIG. 5, it discloses a squeezer patch 500 in accordance with the present invention, which comprises two separate housings 510 and 520. Both housings 510 and 520 are circular in shape and have concave interior surfaces 511 and 521, respectively, which compliment one another. Housing 510 includes the dry chemistry membrane 512 and housing 520 contains the wet chemistry component 522. In addition, the wet chemistry component or gel 522 includes a small hole 523 which activates the chemistry when it is squeezed. In use, the targeted skin area is precleansed and optimally treated with a skin permeation enhancer. The squeezer device 500 is removed from its foil packet with desiccant (not shown), and housing 510 is inserted into housing 520, so that the dry chemistry component 512 and the wet chemistry component or gel 522 are in contact with one another. The two housings 510 and 520 are squeezed to activate the chemistry and to continuously and uniformly wet the dry chemistry membrane 512. The bottom of the wet chemistry component or gel 512 is applied to the pretreated skin area for a sufficient time to permit analyte transfer from the biological fluid within or underneath the skin to the dry chemistry membrane 512 for analyte detection.

Figure 6:
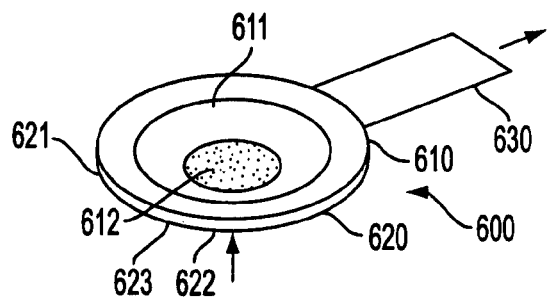
FIG. 6 is a perspective view of a noninvasive transdermal patch according to another embodiment of the present invention.

FIG. 6 depicts, as a further alternative, a slider patch 600. In accordance with the present invention, slider patch 610 comprises top housing 610 and bottom housing 620. Pulltab 630 is sandwiched between top and bottom housings 610 and 620, respectively. Housing 610 includes the dry chemistry membrane 612 and bottom housing 610 contains the wet chemistry component or gel 622. Pulltab 630 can be made of any suitable material which maintains an inpenetrable barrier between dry chemistry membrane 612 and wet chemistry agents or gel 622 during nonuse. Preferably the interior surfaces 611 and 621 of housings 610 and 620, respectively, are concave in shape and match one another, so that when pulltab 630 is removed, the dry chemistry component 612 and the wet chemistry component 622 are in constant contact for continuously and uniformly wetting the dry chemistry component 612. To use, the targeted skin area is precleansed and pretreated with a skin permeation enhancer, if necessary. The slider patch 600 is then removed from the foil packet with desiccant (not shown) and pulltab 630 is removed to activate the chemistry between the dry and wet components 612 and 622, respectively. The bottom of the wet chemistry component 623 is then applied to the pretreated skin area for a sufficient amount of time for analyte detection of an analyte in a biological fluid located within or beneath the skin.

Figure 7:
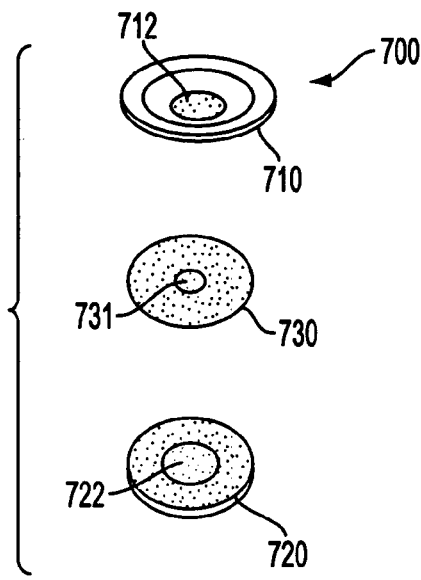
FIG. 7 is an exploded elevational view of a noninvasive transdermal patch according to yet another embodiment of the present invention.

In FIG. 7, a piercer patch 700 in accordance with the present invention is illustrated. The piercer patch 700 comprises housings 710 and 720 and piercer disk 730. Housing 710 includes a dry chemistry membrane 712 and 720 contains the wet chemistry component or gel 722. Piercer disk 730 includes sharp points 731 for nicking foil, into which the wet chemistry component 722 is packed and stored (not shown), to release the wet chemistry component 722 to continuously and uniformly wet the dry chemistry membrane 712. The piercer disk 730 and sharp points 731 can be made of any suitable material, such as metal or plastic. In use, piercer patch 700 is removed from the foil packet with desiccant (not shown) and the targeted skin area is precleansed and, optionally, pretreated with a skin permeation enhancer. The piercer patch 700 is activated by pressing housings 710 and 720 together so that the sharp points pierce the foil (not shown) between housings 710 and 720 to release the wet chemistry components in contact with one another. The bottom surface of the wet chemistry component 722 is then applied to the skin area for a sufficient period of time for analyte detection.

Figure 8:
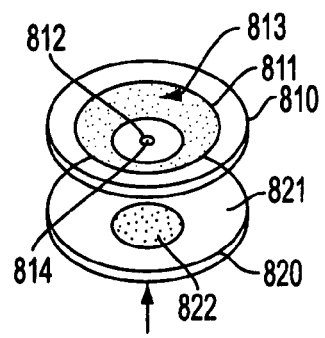
FIG. 8 is an exploded elevational view of a noninvasive transdermal patch according to yet another embodiment of the present invention.
Figure 9:
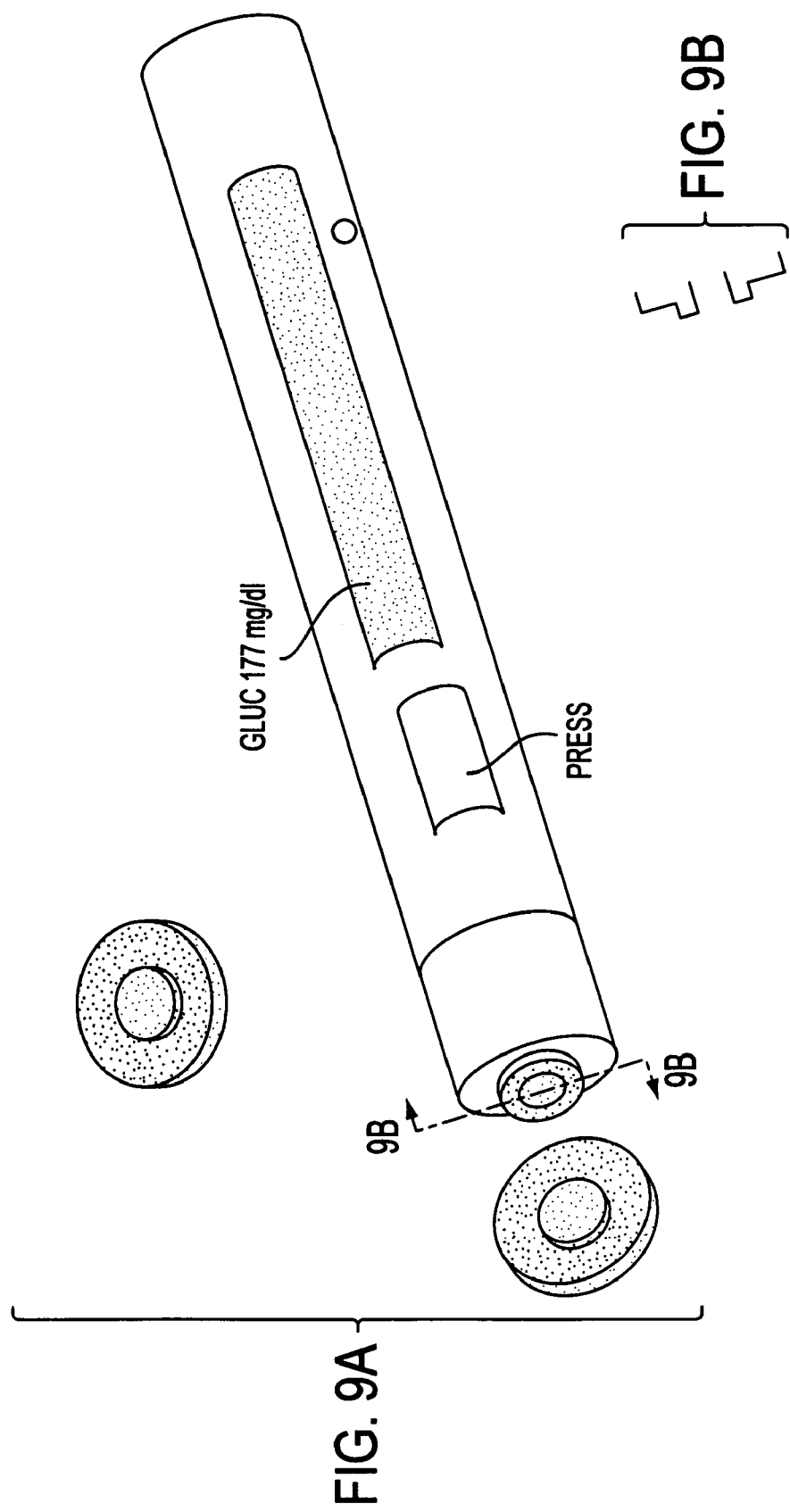
FIG. 9 is a perspective view of a reflectometer in accordance with the present invention.
Figure 10:
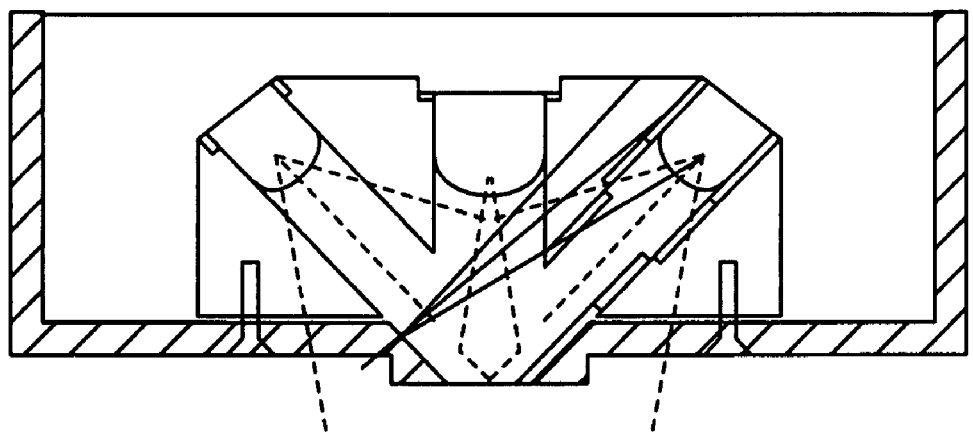
FIG. 10 is a cross-sectional view of the reading head of the reflectometer of FIG. 9.

Turning now to FIG. 8, it discloses a radial flow immunoassay patch 800 which comprises two separate housing 810 and 820. Both housings 810 and 820 are circular in shape and have concave interior surfaces 811 and 821, respectively, which compliment one another. Housing 810 includes the dry chemistry membrane 812 and a donut 813 of absorbent material, such as diagnostic paper, #470, supplied by Schleichr and Schull, and housing 820 contains the wet chemistry component 822. Wet chemistry component 822 is pre-wet with a conjugate disk monoclonal antibody such as anti-BHCG. In addition, the dry chemistry component or gel 812 includes a small spot of antibody, such as AHCG, thereon for detecting the antigen. In use, the targeted skin area is precleansed and optimally treated with a skin permeation enhancer. The device 800 is removed from its foil packet with desiccant (not shown), and housing 810 is inserted into housing 520 so that the wet chemistry component 812 and the wet chemistry component or gel 822 are in contact with one another. The two housing 810 and 820 are squeezed together to activate the chemistry component 812. The bottom of the wet chemistry component or gel 812 is applied to the pretreated skin area for a sufficient time to permit analyte transfer from the biological fluid within or underneath the skin to the dry chemistry membrane 812 for analyte detection.

It should be understood to those of skill in the art that the above alternative patches depicted in FIGS. 3-8 represent examples of various patch configurations in accordance with the present invention. It should be further understood that these exemplary patch configurations do not constitute the only patch variations contemplated by the present invention; but rather, the present invention contemplates any patch configuration which accomplishes the objectives of the instant invention. Moreover, it should be understood that the exemplary patch configurations depicted in FIGS. 3-8 can be made from, for example, the materials and chemical reagent systems discussed herein or any other suitable materials within the ambit of those skilled in this field.

As discussed above, the noninvasive transdermal systems of the present invention include a wet chemistry component comprised of a transfer medium which allows for liquid bridge transfer of an analyte of interest from the biological fluid within or beneath the skin to the dry chemistry component for biological reaction with the chemical reagents to release or form a reporter or indicator molecule (color change), which is indicative of the presence of the analyte in the biological fluid. In accordance with the present invention, the wet chemistry component is in the form of gel layer and is present in the patch in an amount of about 20 mcls to about 35 mcls, and preferable in an amount of about 25 mcls. In a preferred embodiment, the gel layer is a hydrophobic gel. A preferred hydrophobic gel is one formed with carboxy polymethylene, Carbopol™, in a concentration of from about 0.5% to about 2%. A preferred hydrophobic gel in accordance with the present invention is an about 1% carboxy polymethylene, Carbopol™ gel. It should be appreciated that while a carboxy polymethylene gel matrix is preferred, any other suitable gels prepared from, for example, 1% carboxy methylcellulose, agarose, 10% glycerin and 1% carboxy polymethylene in $dH_2O$, 10% polyethylene glycol in 1% carboxy polymethylene in $dH_2O$, and 10% sodium lauryl sulfate and 1% carboxy polymethylene in $dH_2O$, etc., may be utilized, so long as they have the proper viscosity and do not interfere with analyte transfer or detection.

In a further feature of the present invention, the wet chemistry component may include a skin permeation enhancer. Examples of skin permeation enhancers that may be included within the wet chemistry component are propylene glycol, distilled water, ionized water, DMSO, isopropyl alcohol, ethyl acetate, ethyl alcohol, polyethylene glycol, carboxy methylcellulose, 1:1-water:acetonitride, 1:1:1-ethanol:propylene glycol: $dH_2O$, 1:1-ethanol: propylene glycol, 70:25:5-ethanol: $dH_2O$: oleic acid, 70:25:5-ethanol:$OH_2O$:isopropyl palmitate, 1:1-ethanol:water, 75% lactic acid in isopropyl alcohol, 90% lactic acid and 10% Tween80 20% salicylic acid in 50% isopropyl alcohol in $dH_2O$, 1:1:1-ethyl acetate: isopropyl alcohol: $dH_2O$, etc.

In preparing the wet chemistry components or gels of the present invention, it is generally preferable when making, for example, a hydrophobic gel to sprinkle the hydrophobic, such as carboxy polymethylene, slowly with slow mixing to avoid bubbles, followed by deaeration by vacuum. Autoclave, when appropriate, may be utilized for sterilization.

An especially preferred hydrophobic gel with a skin permeation enhancer incorporated therein comprises about 1% carboxy polymethylene, e.g., carbopol and about 10% propylene glycol. Such a preferred hydrophobic gel can be prepared by slowly sprinkling and mixing about 1 g of Carbopol™ 1342 (BF Goodrich) in a total of about 100 ml of deionized water (18 meg ohm) containing about 10% propylene glycol. During mixing, bubbles should be avoided. Following mixing, the gel is deaerated by vacuum.

It should be understood by those of skill in the art that while transfer mediums containing skin permeation enhancers, are preferred, it is not necessary to incorporate skin permeation enhancers into the transfer medium. Alternatively, the present invention envisions the use of transfer mediums, e.g., a hydrophobic gel which is free of a skin permeation enhancer. An example of such a transfer gel is a 1% carboxy polymethylene gel or a 1% carboxy methylcellulose gel, as mentioned hereinabove. Nevertheless, it should be understood, that when a skin permeation enhancer is embodied into the transfer medium, the use of a separate skin permeation enhancer on the skin prior to the application of the noninvasive transdermal patch is optional. However, when a transfer medium free of skin permeation enhancer is selected, as the wet chemistry component 10 in accordance with the present invention, the skin is preferably pretreated with a skin permeation enhancer. A preferred skin permeation enhancer contemplated by the present invention is propylene glycol or a 1:1:1 mixture of isopropyl alcohol, deionized water (18 meg ohm) and ethyl acetate, which can be prepared by simply mixing the three components together. Other skin permeation enhancers that may be used in accordance with the present invention include DMSO, ethyl alcohol, distilled water, deionized water (18 meg ohm), propylene glycol, isopropyl alcohol, lactic acid, ethyl acetate, carboxyl methylcellulose, Tween 80, salicylic-acid (20% in deionozed water/isopropyl alcohol—50/50), limonene, lactic acid 10% in isopropyl alcohol, 90:5:5—isopropyl alcohol:Tween 80:limonene, 10% lactic acid in isopropyl alcohol and 90% lactic acid and 10% Tween 80, etc. Of course, it should be understood that when a skin permeation enhancer is selected, it should be applied to the skin area, which will undergo testing in advance, in a sufficient quantity and for a sufficient period of time prior to the application of the noninvasive transdermal system, so that if the skin permeation enhancer may act in an effective manner to assist in the transfer of the analyte of interest in a biological fluid, such as interstitial fluid, or detection by the dry chemistry component 20 of the present invention. While the quantity and time will vary depending upon the skin penetrant selected, the skin permeation enhancer should be applied in an amount that will permit it to rapidly dry within a short period of time to avoid excess accumulation at the targeted skin site. It should also be appreciated that when a skin permeation enhancer is selected for use in accordance with the present invention, the analyte under investigation should be taken into consideration so that a skin penetrant is not selected which will somehow interfere with the analyte of interest or its detection. For example, a cellulose-type skin permeation enhancer may be possibly incompatible when the analyte under investigation is glucose.

The dry chemistry component 20 of the present invention is comprised of a novel super sensitive or conditioned membrane (a dry chemistry membrane) which, in general, is approximately at least 100 times, and as much as 400-500 times, more sensitive than those dry chemistry membranes currently used to detect an analyte in whole blood. In fact, and quite surprisingly, it has been discovered that, a super sensitive or conditioned membrane has the ability to detect and quantify accurately and quickly the analyte under investigation even though they are in very small concentrations, e.g., about 5 mg/dl or 5 mcg/ml, in small volumes, such as in a 25 mcl sample. Moreover, the sensors of the present invention have the ability to detect analytes in sample sizes generally to small for detection by HPLC methods. Generally speaking, in order for HPLC methods to detect analyte under investigation, it is believed that a sample size of at least about 200 mcl is needed. While any suitable material may be utilized as the base material for the super sensitive or conditioned membranes of the present invention, such as mylar materials, like BioDyne A or BioDyne B supplied by Paul Gelman, an especially preferred material is polyether sulfone distributed under the product name Supor 450™ by Gelman Sciences. This particular polyether sulfone material has a pore size of about 0.45 microns. While this particular polyether sulfone material is preferred, it is nevertheless believed that other polyether sulfone materials may be utilized, such as nylon, having a pore size of about 0.8 microns.

A typical super sensitive or conditioned membrane in accordance with the present invention comprises a glucose reactive formulation for a noninvasive transdermal glucose patch. The glucose reactive formulation comprises a base preparation and an enzyme component as follows:

| Glucose Reactive Formulation for Glucose Patch | |
|---|---|
| Base preparation. 100 ml | |
| 6.0 gm | Polyvinyl Pyrrolidinone K-30 [mw 40,000] (Sigma Chemical) |
| 1.2 gm | Citric Acid Trisodium Salt (Aldirch) |
| 0.10 gm | Citric Acid Monohydrate |
| 0.028 gm | NaBH4 [Sodium Borohidrate] |
| 0.10 gm | Bovine Serum Albumine [BSA] |
| 0.545 gm | O-Tolidine (Sigma Chemical) adjust pH to 5.9-6.0 Add 2.0 ml 10% Gantrez S-95,2 Butendonic [10/0 gm/100 ml] (ISP Technologies) adjust pH to 5.9-6.0 with NaOH |
| 4.0 gm/L | 75% Dioctylsulfosuccinate DOSS[0.533 gm] (Sigma Chemical) |
| 121.0 mg | Glucose Oxidase (GOD) 150 u/ml[150 u 100 ml/124 u/mg] (Fynn Sugar) |
| 38.53 mg | Horse Radish Peroxidase (POD) 100 u/ml [100 u 100 ml/259.55 u/mg] (Worthington) |

The glucose reactive formulation can be prepared as follows. First, prepare the base preparation by intimately mixing the ingredients recited above with one another. Second, mix O-Tolidine in deionized water until dissolved. Third, prepare an enzyme solution as follows: Into a clean suitable sized container, measure the calculated enzyme solution. Slowly add the prepared O-Tolidine to the base solution while mixing until solution is clear. While mixing, add the 20% Gantrex and mix for approximately 15-20 minutes. Thereafter add the DOSS while mixing and continue to mix for an additional 15-10 minutes. Adjust the pH using NaOH to 6.8-6.9. At this point, solution should be clear. Thereafter, add GOD to the clear solution while mixing. Once the GOD has been added, stop mixing and add the POD. Once the POD is dissolved, mix for an additional 15-20 minutes. The glucose reactive solution is now ready for use. During preparation, the mixing should be done in such a way to prevent foaming, so as to avoid denaturing the BSA. It should be appreciated by those of skill in the art that because the glucose reactive formulation contains excessive quantities of both the enzymes and chromophore, O-Tolidine, the base preparation is needed in the preparation to dissolve the excessive amounts of the chromopore, O-Tolidine, and enzymes.

A super sensitive or conditioned glucose reactive membrane may be prepared as follows. A sheet of the polyether sulfone or other material is submerged into the glucose reactive solution as prepared above, at an angle of about 45° to drive air out of the membrane material while introducing the glucose reactive solution into the membrane material. Slowly pull the membrane material through the solution to saturate the membrane material. The wet, saturated membrane material is then dried by passing it through a conventional 10 foot-long drier at a temperature of less than about 41° C. at a speed of about 2 feet/minute or for about 5 minutes. Once dried, the top and bottom ends of the super sensitive or conditioned membrane should be removed because of the unevenness of the saturation at the top and bottom ends. The super sensitive or conditioned membrane is now available for use as the dry chemistry membrane 20 of the present invention.

An alternative glucose reactive membrane may be prepared as follows:

Dry chemistry strips are prepared, in accordance with the process of this invention, from the following materials and reagents in similar concentrations as noted above:

(a) Membrane
  1.) Gelman Sciences, Ann Arbor, Mich., Polyethersulfone (Supor) Porosity 0.22-0.8 microns
(b) Indicator about 1% (w/w) aqueous solution deionized water (18 meg ohm) O-Tolidine hydrochloride
(c) Glucose Specific Reagent Cocktail
  1.) glucose oxidate 125 IU activity per ml
  2.) peroxidase 50 IU of activity per ml
  3.) albumin 0.2% (w/v) (enzyme stabilizer)
(d) conditioning and flow control agents—polyvinyl pyrolidone 3% (w/v) dioctylsulfosuccinate 0.2% and 2 Butendioic acid polymer (0.35%) all buffered with 0.1 m citrate, (pH 6.4)

Each of the above reagents are prepared fresh from reagent grade chemical and deionized water. The base preparation is first prepared by mixing the components together. The indicator is then added followed by the cocktail. Once prepared, the membrane is dipped briefly (about 30 seconds) into it until uniformly wetted. It is then air dried at 37° C. for about 15 minutes. The dried membrane is stored with desiccant protected from moisture and light. This dry chemistry membrane is cut into strips and can be encapsulated, (i.e. glued) within the fold of an adhesive coated mylar that is then affixed within the device. It is believed that when this alternative glucose formulation and process are selected, approximately 5 liters will effectively coat about 200 sq. Ft. of a membrane, such as a BioDyne A membrane.

It has been surprisingly found that the above described glucose reactive membranes have the unique ability to detect as little as about 5 mg/dl or 5 mcg/ml of glucose which has diffused from the interstitial fluid into the wet chemistry component. It can now be readily appreciated by those of skill in this art that the novel noninvasive transdermal patches of the present invention are quite capable of accurately, reliably and quantitatively detecting glucose in a subject. Moreover, the novel noninvasive transdermal patches of the present invention are simple and easy to use by nonmedically trained personnel while eliminating the need for invasive, painful techniques utilized heretofore. Those skilled in this art should therefore readily appreciate that the novel noninvasive transdermal patches of the present invention provide a significant advancement over the prior systems and techniques concerning the body fluid analyte collecting and detection.

While the dry chemistry membrane 20 of the present invention is described herein with particular reference to a certain glucose membranes, it should nevertheless be understood that any other suitable membrane may be employed in accordance with the present invention, such as those described and illustrated in U.S. Pat. No. 4,774,192, which is incorporated herein by reference in its entirety. It should also be understood by those of skill in the art that, while the above-discussed super sensitive or conditioned membranes are prepared with the chromophore, O-Tolidine, any other suitable chromophore, such as tetra-methyl benzidine (TMB), may be employed. It should further be appreciated that other indicator systems, such as fluorphores or polarographic or enzyme electrodes, may be employed to detect the analytes with the noninvasive systems of the present invention, so long as the objectives of the instant invention are not defeated.

Moreover, it should be understood by those of skill in the art, that the above-discussion, with respect to glucose analysis of interstitial fluid, can by analogy be readily extrapolated to the preparation of super sensitive or conditioned membranes and performance of clinical assays for the detection of a wide variety of other analytes typically found in biological fluid samples, such as interstitial fluid. The super sensitive or conditioned membrane systems of this invention are, thus, applicable to clinical analysis of, for example, cholesterol, triglycerides, bilirubin, creatinine, urea, alpha-amylase, L-lactic acid, alanine aminotransferase (ALT/GPT), aspartate aminotransferase (AST/GOT), albumin, uric acid, fructose amine, potassium, sodium, chloride, pyruvate dehydrogenase, phenylalaninehydroxylase, purine nucleotide enzymes and phenylalanine hydroxylase or its substrates, such as phenyl-alanine, phenyl-pyruvate or phenyl-lactate, to name a few. The assay format can be essentially the same as that described previously for glucose, or optionally involve the combination of a conditioned membrane/reagent system with one or more additional lamina (i.e. spreading layer, radiation blocking layer, semipermeable diffusion layer, etc.).

The preparation of a conditioned membrane, incorporating a dry chemistry reagent system for each of the above analytes, follows essentially the same process as described for preparation of glucose specific dry chemistry reagent systems (e.g. conditioning the membrane with a flow control agent and the absorption of the indicator/reagent cocktail). The conditioning of the membrane can, thus, occur prior to or concurrent with contact of the membrane with one or more of the constituents of the dry chemistry reagent systems.

Generally speaking, in an alanine aminotransferase (ALT/GPT) assay, the enzyme reacts with alanine and alpha-ketoglutarate to form pyruvate and glutamate. The pyruvate that forms reacts with 2,4-dinitro phenylhydrazine that is colored at 490-520 nm. High levels of alanine aminotransferase are associated with hepatitis and other liver diseases. In an aspartate aminotransferase (AST/GOT) assay, the enzyme reacts with aspartate 1 and 2-oxoglutarate to form oxaloacetate and glutamate. The oxaloacetate that forms reacts with 2,4-dinitro phenylhydrazine that is colored at 490-520 nm. High levels of oxaloacetate are associated with myocardial infarction hepatitis and other liver diseases as well as muscular dystrophy dermatomyositis. In an albumin assay, bromcresol purple binds quantitatively with human serum albumin forming a stable complex with maximum absorbance at 600 nm. Low levels of human serum albumin are associated with liver disease, nephrotic syndrome, malnutrition and protein enteropathies. High levels of human serum albumin are consistent with dehydration. Prealbumin may be of diagnostic value for diabetes and malnutrition. Normal values are 3-5 gm/dl (30-50 gm/L). Critical limits for children are lows of 10-25 gm/L or highs of 60-80 gm/L. In a bilirubin assay, diazotized sulfanilic acid reacts quantitatively with conjugated bilirubin forming azobilirubin with maximum absorbance at 560 nm. High levels of bilirubin are associated with biliary obstruction and hepatocellular disease. In the presence of dimethyl sulfoxide (DMSO) both conjugated (direct) and unconjugated (free), bilirubin reacts and is then indicative of hemolytic disorders in adults and newborns. Critical limits for adults are highs of 5-30 mg/dl (86-513 micromol/L) and 86-342 micromol/L for children; normal levels are up to 0.3 mg/dl serum conjugated, but 1-12 mg/dl (96-308 micromol/L) for newborns. Patches in accordance with the present invention, after a few minutes, would read 1/50th of these values. In a chloride assay, mercuric thioisocyanate reacts with chloride ions to give mercuric chloride, the thiocyanate produced reacts with iron to give a reddish brown product. Low levels of chloride ions are associated with gastrointestinal or salt losing nephritis, Addisons disease. High levels are associated with heart failure and Cushing's syndrome. The critical limits are 60-90 mmol/L (1/50th of that is to be expected in a patch of the present invention). Normal levels are 95-103 mEq./L). In a cholesterol, total assay, cholesterol esters are reacted with cholesterol esterase. The total free cholesterol is further reacted with cholesterol oxides which in turn generates peroxide detected with peroxidase coupled to a colored dye O-Tolidine. Increased levels of cholesterol are associated with atherosclerosis, nephrosis, diabetes mellitus, myxedema, and obstructive jaundice. Decreased levels of cholesterol are observed in hyperthyroidism, anemia, malabsorption and wasting syndromes. Normal values are 150-250 mg/dl. (varies with diet and age). Values above 200 mg/dl would suggest consulting a physician. In a fructose amine assay, fructose amine reduces nitrotetrazolium blue at alkaline pH. Fructose amine is useful in the management of diabetes mellitus. Levels are indicative of glucose control. In a lactic acid assay, porcine lactate dehydrogenase (Boehringer Mannehim) reacts with lactate in the presence of nicotinamide adeninine dinucleotide (NAD) to produce NADH (NAD reduced) plus pyruvate. The NADH is then detected by using the enzyme diaphorase (Unitika) to react with a tetrazolium salt producing a colored formazan. The color produced is directly proportional to the lactic acid concentration. Lactic acid is useful in critical care situations, as a measure of the success of supportive therapies to predict the mortality rate. High levels correlate with severity of clinical outcome. Blood lactate has become a prognostic indicator of survival in patients with acute myocardial infarction and is also used as an indicator of severe neonatal asphyxia. Lactic acidosis is also found in patients with diabetes mellitus and hepatic failure. Can be used in sports medicine to evaluate endurance and fitness. Normal values are 5-20 mg/dl in venous blood; lower (3-7 mg/dl) in arterial blood. Critical limits are highs of 20.7-45 mg/dl (2.3-5.0 mmol/L). In a potassium assay, ion specific electrodes have become stable and sensitive enough to be used to detect the levels expected in a patch (critical limits are 1/50th of that found in the blood: i.e., 0.05-0.07 mmol/L) after a few minutes skin contact. Potassium is useful in critical care situations as a measure of the success of supportive therapies to predict the mortality rate. High levels of potassium correlate with severity of clinical outcome. Blood potassium has become a prognostic indicator of survival in patients with acute myocardial infarction. The normal values are 3.8-5.0 mEq./L (same as mmol/L) in plasma; critical limits are low 2.5-3.6 mmol/L or high of 5-8 mmol/L. In a sodium assay, ion specific electrodes have become stable and sensitive enough to be used to detect the levels expected in a patch (critical limits are 1/50th of that found in the blood after a few minutes skin contact. The normal values are 136-142 mEq./L (same as mmol/L) in plasma; critical limits are low of 110-137 mmol/L or heights of 145-170 mmol/L. In a triglycerides assay, triglycerides react with lipoprotein lipase giving glycerol that when phosphorylated produces peroxide in the presence of glycerol phosphate oxidate. This can be detected with a color dye and peroxidase with the noninvasive transdermal systems of the present invention. High levels of triglycerides are involved with nephrotic syndrome, coronary artery disease, diabetes and liver disease. Normal values are 10-190 mg/dl in serum. In an uric acid assay, uric acid reacts with uricase to form allantoic and peroxide that is detected by appropriate means. High levels of uric acid are associated with gout, leukemia, toxemia of pregnancy and sever renal impairment. Normal values are male 2.1-7.8 Mg./gl; female 2.0-6.4 mg/dl. The critical limits are a high of 10-15 mg/dl (595-892 micromol/L).

Such examples of super sensitive or conditioned membranes which can be made in accordance with the present invention are now illustrated.

A super sensitive or conditioned membrane for urea can be prepared by absorption into a conditioned membrane, of appropriate concentrations of urease, buffer, and an indicator sensitive to changes in pH. When a whole blood sample is brought in contact with the sample receptive surface of the membrane, the serum is taken up by the membrane. The urea present in the serum is digested by the urease enzyme, thereby liberating ammonia in solution. The ammonia can then react with a suitable indicator (i.e., a protonated merocyanide dye). The pH of the membrane is buffered to about 8.0 to keep the equilibrium concentration of the ammonia relatively low. The indicator is monitored at 520 nm. Additional details of this specific reagent system are described in the open literature, see for example Spayd, R. W. et al., *Clin. Chem.*, 24(8):1343.

A super sensitive or conditioned membrane for alpha-amylase can be prepared by absorption, into a conditioned membrane, of appropriate concentrations of a derivatized substrate (i.e., starch) and buffer. When the whole blood sample is applied to the sample receptive surface of the test strip, the serum is absorbed into the membrane, thus, initiating digestion of the derivatized substrate by the alpha-amylase in the sample. This digestion of the substrate releases a chromophore or fluorophore which can be monitored in accordance with accepted techniques and readily available equipment. Additional details for this specific reagent system also appear in the Spayd publication, previously referenced herein.

A super sensitive or conditioned membrane for bilirubin can be prepared by absorption, into a conditioned membrane, of appropriate concentrations of certain cationic polymers (i.e., polymeric quaternary salts) and phosphate buffer (pH approximately 7.4). When an interstitial sample is applied to the sample receptive surface of the test strip, the fluid is absorbed into the membrane, thereby initiating interaction of the bilirubin and the cationic polymer. Such interaction results in a shift in the maximum absorption of the bilirubin from 440 to 460 nm with an accompanying substantial increase in absorption at the new peak. Additional details relating to this specific reagent system also appear in the previously referenced Spayd publication.

A super sensitive or conditioned membrane for triglycerides (triaclyglycerols) can be prepared by absorption, into a conditioned membrane, or surfactant, lipase, adenosine triphosphate (ATP), glycerol kinase and L-alpha-glycerol phosphate oxidase, and a triarylimidazole leuco dye. In brief, the surfactant aids in dissociation of the lipoprotein complex so that the lipase can react with the triglycerides for form glycerol and fatty acids. The glycerol is then phosphorylated with the adenosine triphosphate in the presence of the glycerol kinase enzyme. The L-alpha-glycerol phosphate thus produced is then oxidized by the L-alpha-glycerol phosphate oxidase to dihydroxy acetone phosphate and hydrogen peroxide. The hydrogen peroxide oxidizes the lueco dye, producing a colored indicator which has a peak absorption at 640 nm. Additional details relating to this specific reagent system appear in the previously referenced Spayd publication.

An alternative and preferred chemistry reagent system for triglyceride analysis can be prepared by absorption, into a conditioned membrane, of lipase, glycerol dehydrogenase, p-iodonitrotetrozolium violet (INT) and diaphorase. The serum triglycerides initially interact with the chemistry reagent system and are hydrolyzed to free glycerol and fatty acids. The free glycerol is now converted to the dihydroxyacetone by glycerol dehydrogenase, in the presence of NAD. Simultaneous with such conversion, INT (colorless) is reduced by diaphorase, in the presence of NADH, to red dye (maximum gamma=500 nm). The change is absorbance of the test strip at 500 nm is directly proportional to the concentration of serum triglycerides.

A super sensitive or conditioned membrane for determination of total cholesterol in interstitial fluid can be prepared by absorption, into a conditioned membrane, of cholesterol ester hydrolase, cholesterol oxidase, a leuco dye and peroxidase. Upon application of a whole blood sample to the sample receptive surface of the test strop, the serum is absorbed into the membrane, thereby initiating conversion of the cholesterol esters to cholesterol, the oxidation of the cholesterol is accomplished by the cholesterol oxidase enzyme, thereby liberating peroxide. The peroxide and leuco dye then interact in the presence of peroxidase to form a highly colored indicator which can be monitored either visually or through the use of instrumentation. Additional details relating to this specific reagent system appear in the open literature, see Dappen, G. N., et al. Clin. Chem., Vol 28, No. 5 (1982), 1159.

Alternatively, a super sensitive membrane for detection of total cholesterol in interstitial fluid can be prepared, in accordance with this invention, from the following materials and reagents:

(a) Membrane
  1) Corning Costar, Cambridge, Mass., Bioblot nylon plus Porosity 0.22-0.8 microns
(b) Indicator about 1% (w/w) aqueous solution deionized water Tetramethylbenzidine
(c) Cholesterol Specific Mixed Reagent Cocktail
  1) Cholesterol oxidase 150 IU activity per ml
  2) Cholesterol esterase 150 IU activity per ml
  3) peroxidase 50 IU of activity per ml
  4) stabilizer for the enzyme-albumin 0.2% (w/v)

(d) conditioning and flow control agents-polyvinyl pyrolidone 3% (w/v) and dioctylsulfosuccinate 0.2% with 2 Butendioic acid polymer (0.35%) all buffered with 0.1 M citrate, (pH 6.4).

Each of the above reagents are prepared fresh from reagent grade chemical and deionized water. They are mixed together as one homogenous solution and the membrane is dipped briefly (about 30 second) into it until uniformly wetted. This is then air dried at about 37° C. for about 15 minutes. This is stored with desiccant protected from moisture and a light. This dry chemistry membrane is cut into strips and encapsulated, (i.e. glued) within the fold of an adhesive coated mylar that is then affixed within the device.

In yet another alternative, a super sensitive or conditioned membrane for a cholesterol reactive formulation for cholesterol detection can be prepared from the following enzymatic solution preparation. The enzymatic solution preparation can then be formulated with the base preparation as described earlier hereinabove for the glucose reactive formulation for glucose patch.

| Cholesterol Enzymatic Solution Preparation | | | |
|---|---|---|---|
| To make 30 ml: | | | |
| O-TOLIDINE 5.45 gm/L | | 163.5 mg | |
| HORSERADISH PEROXIDASE | 14.3 U/mg | [259.55] | 1.65 mg |
| CHOLESTEROL OXIDASE 20.0 U/ml | | [25.1 U/mg] | 23.9 mg |
| CHOLESTEROL ESTERASE | 60.5 U/mg | 160.0 U/mg | 11.34 mg |

Once such a cholesterol reactive formulation is prepared, it can be air dried onto a suitable membrane material, such as a polyether sulfone membrane, Supor 450. supplied by Gelman Sciences or the BioDyne A or BioDyne B membranes supplied by Paul Gelman, and used with a wet chemistry component 10 of the present invention, such as the hydrophobic gel comprising about 1% carboxy polymethylene and about 10% propylene glycol.

A super sensitive or conditioned membrane for lactate detection can be prepared from, for example, the following formula, which is admixed with the base preparation described hereinabove for the glucose reactive formulation for glucose patch, and then saturated into a suitable membrane material such as a polyether sulfane Supor 450 membrane supplied by Gelman Sciences or a BioDyne A or BioDyne B membrane supplied by Paul Gelman.

| Lactate Reactive Formula for Lactate Patch Based on 100 ml | |
|---|---|
| PVP K-30 | 6.0% |
| K—PO$_4$ | 0.15 M |
| BSA | 0.10% |
| LDH (rabbit muscle) | 15000 U (Boehringer Mannehim) |
| NAD | 2.0 mM (Unitika) |
| Diaphorase II | 10000 U (Dojindo) |
| WST4 (tetrazolium) | 1.0 mM |

A super sensitive or conditioned membrane for creatinine can be prepared by absorption into a conditioned membrane of appropriate concentrations of creatinine imino hydrolase and an ammonia indicator (i.e., bromphenol blue). Upon application of an interstitial fluid sample to the receptive surface of the membrane, the interstitial fluid sample is absorbed into the membrane, thereby initiating interaction of the creatinine and the enzyme, creatinine amino hydrolase, resulting in the liberation of ammonia. The ammonia thereby reacts with the indicator and the color development monitored visually or with conventional instrumentation. Additional details relating to this specific reagent appear in the open literature, see for example Toffaietti, J., et al., Clin. Chem., Vol. 29, No. 4 (1983), 684. It is also contemplated that the dry chemistry reagent systems of this invention be utilized in a multiple lamina test slide of the type developed by Eastman Kodak Company of Rochester, N.Y. (Hereinafter "Kodak format"). Where a permeable material (i.e. spreading layer) is placed in contiguous contact with the sample receptive surface of a treated membrane, such contract will influence (change) the rate and quantity of interstitial fluid transported through the membrane, and consequently the rate and extent of the reaction mediated by the analyte specific components within the membrane. At higher blood analyte levels the transport of sample across the membrane can result in an overabundance of analyte and thus a foreshortening of the usable range of measurement.

Also contemplated by the present invention is the adaption of the membrane to a displacement immunoassay of the type described in Liotta U.S. Pat. No. 4,446,232, which is hereby incorporated by reference in its entirety. In the configurations, the receptive surface of the membrane is coated with an enzyme labeled antigen or antibody (hereinafter "enzyme labeled conjugate"). The method of application of the coating of the receptive surface insures against penetration of the coating material into the matrix of the membrane. The balance of the immunochemistry reagent system, notably, a chromogenic or fluorogenic substrate for the enzyme is incorporated into the conditioned membrane, so as to preserve its physical isolation from the surface coating. The contact of the sample with the coating on the surface of the membrane results in displacement of enzyme labeled material. The displacement of the enzyme labeled conjugate is based upon the dynamic equilibrium which is caused by the presence of an analyte in the sample and the competition with the conjugate for binding to an analyte mimic in the surface coating.

This displaced enzyme labeled conjugate, along with a portion of the fluid fraction of the sample, is absorbed in the matrix of the membrane. The enzyme portion of this conjugate interacts with a substrate specific for the enzyme and thereby produces a discernible change in color or fluorescence which is indicative of the analyte of interest. This change can be observed visually, (in the case of color change) or by instrumentation designed for that purpose.

In practicing the present invention, the targeted skin area for testing should first be thoroughly cleansed. This can be accomplished by washing the area thoroughly with water by rinsing and then permitted to dry. Once cleansed, the skin permeation enhancer, if separately utilized, should be applied to that area of skin in a sufficient quantity and for a sufficient period of time. Typically, there is no set amount, but the amount applied should be effective as described herein. The time should be sufficient to permit the skin permeation enhancer to penetrate the skin to assist extraction of the body fluid such as interstitial fluid. This generally takes only a few seconds. Of course, if a skin permeation enhancer is selected, it should not in any way interfere with the analyte under investigation. Thereafter, the noninvasive transdermal system, such as the patch depicted in FIG. 1A, 1B, 1C or 2, should be immediately applied, so that the wet chemistry component 10 is in direct and continuous contact with the cleansed skin area, which may or may not have been pretreated with a skin permeation enhancer, and the dry chemistry component 20 is in direct and continuous contact with the wet chemistry component 10. Preferably, such application should be for a period of between about 3 and 15 minutes, preferably between about 4 to about 6, minutes and more preferably, about 5 minutes. Also, immediately prior to skin application, the wet and dry chemistry components 10 and 20, respectively, should be placed in contact with one another for purposes of continuously and uniformly wetting the dry chemistry component 20, so that reliable analyte detection can be made.

While not wishing to be limited to any particular theory or mechanism of action, it is believed that the underlying mechanism of the patch is as follows. First, chemicals in the patch temporarily dissolve the lipid barrier of the skin which seals the dead cells of the uppermost layer of the stratus corneum. This results in a penetration of the stratus corneum by converting it into a semi-permeable membrane through which the interstitial fluid containing glucose is withdrawn. The glucose from the interstitial fluid in combination with the patented transport medium, diffuses through the skin to the site of the chemical reaction on the membrane containing the glucose-specific reactants. After about 3-4 minutes, a biochemical equilibrium is reached resulting in an end point color reaction which is measured optically by a highly sensitive reflectance meter.

Reference is now made to FIGS. 1A, 1B and 1C and FIG. 2 wherein there is shown a perspective view of a transdermal patch 1 which develops a color shade indicative of the detected presence within the body of an analyte of interest (and perhaps also its concentration). As discussed hereinbefore, the patch 1 has a rounded rectangular shape (as shown), but may also have other shapes as desired, such as depicted in FIGS. 3-8. A top surface 32 of the patch 1 includes a generally circular opening 33 which exposes a membrane 20 to view. In general, a bottom surface (not shown) of the patch 1 includes an adhesive layer and may be affixed to the skin of a patient. A certain analyte of interest is then extracted from the skin and transported through a gel-like transport medium to the membrane 20. At the membrane 20, a biological and chemical reaction occurs with respect to the extracted analyte of interest to develop a color indicator thereon which is indicative of the presence within the body of the analyte. The shade of the developed color indication may also be indicative of analyte concentration level within the body. As an example, the analyte of interest may relate to blood sugar, and thus the developed color shade on the membrane would be indicative of glucose level. Other analytes of interest could be extracted by the patch 1 and used to develop color indications on the membrane 20 related to cholesterol, triglycerides, bilirubin, creatinine, urea, alpha-amylase, L-lactic acid, alanine aminotransferase (ALT/GPT), aspartate aminotransferase (AST/GOT), albumin, uric acid, fructose amine, potassium, sodium, chloride, pyruvate dehydrogenase, phenylalaninehydroxylase, purine nucleotide enzymes and phenylalanine hydroxylase or its substrates such as phenyl-alanine, phenyl-pyruvate or phenyl-lactate, to name a few.

Reference is now made to FIG. 47 wherein there is shown a perspective view of a testing strip 2000 which develops a color shade indicative of the presence within the body of an analyte of interest (and perhaps also its concentration). The strip 2000 has a generally rectangular shape. A top surface 2200 of the strip 2000 includes a testing region 2400. In general, a drop of bodily fluid (such as blood, urine, saliva, perspiration, and the like) is deposited on the testing region 2400. A biological and chemical reaction occurs with respect to an analyte of interest within the deposited fluid to develop a color indicator on the stip 2000 indicative of the presence within the body of the analyte. The shade of the developed color indication may also be indicative of analyte concentration level within the body. As an example, the analyte of interest may relate to blood sugar, and thus the developed color shade on the strip 2000 would be indicative of glucose level. Other analytes of interest, such as those discussed above with respect to the transdermal patch 1, could be processed in the testing region 2400 and used to develop color indications related to analyte concentrations.

Reference is now made to FIGS. 48A and 48B wherein there are shown top and side views, respectively, of a handheld reflectometer 3000 suitable for reading developed color and shade on the transdermal patch 1 of FIGS. 1A, 1B and 1C and FIG. 2. The reflectometer 3000 includes a sensor head 3200 on one end of a semi-cylindrical case 3400 that can be comfortably held in one hand. A "READ" button 3600 activates the reflectometer 3000 to make a measurement of color and shade at the sensor head 3200. A liquid crystal display (LCD) 3800 provides numerical output to a user of the reflectometer 3000 that is indicative of the color shade, such as for example, a voltage level, or of some measurable quantity or quality related to that read color shade, such as, for example, a concentration level. The display 3800 may also provide other important information to the user such as date and time of day. If the display 3800 is capable of producing alphabetic and/or graphic as well as numeric characters, the display may also be used to provide messages to the user, perhaps relating to instructions for use, error indications, icons, reminders, and the like. Two key switches, a "SCROLL" button 4000 and a "SELECT" button 4200, are located on the face of the reflectometer 3000. Utilizing these buttons 4000 and 4200, the user may set date and time of day information. These buttons 4000 and 4200 may further be utilized to program alarms which alert the user as to when it is necessary to take a reading. The user may still further utilize the buttons 4000 and 4200 to enter data into the reflectometer 3000 that is necessary to ensure accurate measurement and information output. As an example, the user may select a manufacturing batch code for the transdermal patch 1, or input color/shade data for calibrating the reflectometer 3000, or select the type of testing to be performed, for example, glucose versus cholesterol. A battery compartment 4400 is located in the top end of the meter. An external port connection (not shown) may also be provided to allow the user to connect the reflectometer 3000 up to a personal computer or a telephone line or an infra-red communications link in order to communicate readings. The reflectometer 3000 further includes an opening 4600 for a speaker (not shown) that may produce sounds such as alarm sounds and data entry confirmation sounds.

Operation of reflectometer 3000 may be better understood by presentation of the following example of its use with a transdermal patch 1, such as that illustrated in FIGS. 1A, 1B and 1C and FIG. 2. Once applied to the skin, the transdermal patch 1 requires approximately a three to five-minute incubation period, dependent on number of factors including temperature. As an example, the transdermal patch 1 is preferably attached to the skin on the inside of the patient's forearm. Once the transdermal patch 1 is applied to the skin, the user may depress the SELECT button 4200 to start a user chosen, reflectometer calculated or pre-programmed count-down period which measures the time required for incubation and development of the color shade indicative of extracted analyte. After the time expires, an audible alarm alerts the user that it is now time to take a reading. A cylindrical shaped protruding nose portion 4800 of the sensor head 3200, generally matching in size and shape the circular shape of the opening 33, is then inserted into the opening 33 of the transdermal patch 1 and positioned adjacent the membrane 20. The user then depresses the "READ" button 3600 to power up the device and initiate reflectometer 3000 operation to detect and measure any developed color and shade present on the membrane 20. Data such as a signal voltage level relating to the detected color shade or an analyte concentration relating to the detected color shade is then output for user consideration on the display 3800. Alternatively or additionally, this data may be output through the external port connection for remote processing and analysis to inform the user of analyte concentration information.

Reference is now made to FIG. 49 wherein there is shown a cross-sectional view of the sensor head 3200 of the hand-held reflectometer 3000 shown in FIGS. 48A and 48B. The sensor head 3200 contains a dual light source to increase the reflective signal strength and to more uniformly illuminate the target surface of the membrane 20 where the color and shade indicative of analyte presence and concentration level is developed. Two light emitting diodes (LEDs) 5000 are mounted in a housing 5200 at a certain angle Θ to normal 5400 with respect to the membrane 20. The LEDs 5000 may be of any suitable color related to the color shades to be detected. As an example, red LEDs 5000 with a wavelength of approximately 637 nm have been found to produce excellent results in detecting the color shades which develop on the membrane 20 from the use of an appropriate chromophore or fluorophore indicator, such as O-Tolidine, tetra-methyl benzine, and the like, during glucose analyte testing. LEDs of other colors, such as green, or perhaps infra-red may be used, perhaps in conjunction with the red LEDs, depending on the selected chromophore or fluorophore indicator. The housing 5200 is constructed with a low-expansion plastic such as Ryton, preferably with a non-reflective surface, and should be opaque as to the wavelength of the light source to substantially eliminate any background signal from stray reflection of light emitted from the LEDs 5000. The angle Θ may be any angle that minimizes detection of specular reflection and is preferably approximately forty to forty-five degrees. The LEDs 500 each have a relatively narrow (for example, fifteen degree) projection angle with respect to their emitted light output. The light output from the LEDs 5000 is directed along a light pipe (or collimator) 5600 through an opening 5800 in the protruding nose 4800 portion of the sensor head 3200 to illuminate the target surface. The position of the LEDs 5000 along the length of the light pipe 5600 may be adjusted during fabrication of the reflectometer to alter the intensity of target surface illumination and the effects and instances of side reflections within the light pipe. A photo transistor 6000 is mounted within the housing 5200 and oriented along the normal 5400 with respect to the target surface of the membrane 20 for the transdermal patch 1. The photo transistor 6000 similarly has a relatively narrow, for example, fifteen degree, viewing angle. Reflected light emitted from the target surface of the membrane 20 passes through the opening 5800 in the protruding nose 4800 portion of the sensor head 3200, and is directed along a light pipe (or collimator) 6200 to the photo transistor 6000. The position of the photo transistor 6000 along the length of the light pipe 6200 may be adjusted during fabrication of the reflectometer to alter the sensitivity and tolerance of the reflectometer in reading target surface illumination and color shade. Arrangement of the LEDs 5000 and photo transistor 6000 in the illustrated angle Θ offset and symmetrical orientation serves to minimize detection of specular reflection off the target surface of the membrane 20 and reduce the effect of rotational error about the normal 5400 that may result from a slightly uneven illumination of the target surface.

Reference is now made to FIG. 50 wherein there is shown a perspective view of a desk-top reflectometer 3000' suitable for reading developed color shade on the testing strip 2000 of FIG. 47. The reflectometer 3000' includes a reading site 3200'. A "READ" button 3600 activates the reflectometer 3000' to make a measurement of color shade at the reading site 3200'. A liquid crystal display (LCD) 3800 provides numerical output to a user of the reflectometer 3000' that is indicative of the detected color shade or of some measurable quantity or quality related to that read color shade. The display 3800 may also provide other important information to the user such date and time of day. If the display 3800 is capable of producing alphabetic and/or graphic as well as numeric characters, the display may also be used to provide messages to the user, perhaps relating to instructions for use, error indications, icons, reminders, and the like. Two key switches, a "SCROLL" button 4000 and a "SELECT" button 4200, are located on the face of the reflectometer 3000'. Utilizing these buttons 4000 and 4200, the user may set date and time of day information. These buttons 4000 and 4200 may further be utilized to program alarms which alert the user as to when it is necessary to take a reading. The user may still further utilize the buttons 4000 and 4200 to enter data into the reflectometer 3000' that is necessary to ensure accurate measurement and information output. As an example, the user may select a manufacturing batch code for the testing strip 2000, or input color/shade data for calibrating the reflectometer 3000', or select the type of testing to be performed, for example, glucose versus cholesterol. An external port connection (not shown) may be provided to allow the user to connect the reflectometer 3000' up to a personal computer or a telephone line or an infra-red communications link in order to communicate readings. The reflectometer 3000' further includes an opening 4600 for a speaker (not shown) that may produce sounds such as alarm sounds and data entry confirmation sounds.

Operation of reflectometer 3000' may be better understood by presentation of the following example of its use with a testing strip 2000 such as that illustrated in FIG. 47. The reflectometer 3000' is activated and recognizes from detected voltage level whether a testing strip is in place within a slot 7000. If not, the reflectometer 3000' prompts the patient to insert a strip. Responsive to insertion of a testing strip into the slot 7000, the reflectometer 3000' prompts the patient to deposit a sufficient amount of bodily fluid, such as blood, urine, saliva, perspiration, and the like, is then deposited on the testing region 2400 of the strip 2000. A biological and chemical reaction occurs with respect to an analyte of interest within the deposited fluid to develop a color indicator on the strip 2000 whose shade can be related to analyte concentration levels. A timer is then initiated to measure whether sufficient progress in the chemical reaction, based on detected voltage level, occurs within a predetermined first time period, that may be user chosen, reflectometer calculated or pre-programmed. If not, the patient is prompted to start the testing process over with a new strip. If sufficient progress occurs within this first time period, the timer then starts measuring a second time period, that may be user chosen, reflectometer calculated or pre-programmed, to detect completion of the testing process. In one supported testing procedure, expiration of the second time period initiates reflectometer 3000' operation to detect and measure color shade on the strip 2000. Data such as a signal voltage level relating to the developed color shade or an analyte concentration relating to the developed color shade is then output for user consideration on the display 3800. In another supported testing procedure, the reflectometer 3000' operates to measure a voltage level indicative of detected color shade on the strip 2000. If the measured voltage level stabilizes before expiration of the second time period, data such as a signal voltage level relating to the developed color shade or an analyte concentration relating to the developed color shade is then output for user consideration on the display 3800. Alternatively or additionally, the data may be output through the external port connection for remote processing and analysis to inform the user of analyte concentration information. In the event that either 1) the measured voltage level does not stabilize, or 2) the measured voltage level drops below an acceptable threshold, an error message is displayed to prompt the patient to start the testing process over with a new strip.

Reference is now made to FIG. 51 wherein there is shown a cross-sectional view of the reading site 3200' of the desk-top reflectometer 3000' shown in FIG. 50. The reading site 3200' contains a dual light source to increase the reflective signal strength and to more uniformly illuminate the target surface of the strip 2000. Two light emitting diodes (LEDs) 5000 are mounted in a housing 5200 at a certain angle Θ to normal 5400 with respect to the strip 2000. The LEDs 5000 may be of any suitable color related to the color shades to be detected. As an example, red LEDs 5000 with a wavelength of approximately 637 nm have been found to produce excellent results in detecting the color shades which develop on the strip 2000 from the use of an appropriate chromophore or fluorophore indicator during cholesterol analyte testing. LEDs of other colors, such as green, or perhaps infra-red may be used, perhaps in conjunction with the red LEDs, depending on the selected chromophore or fluorophore indicator. The housing 5200 is constructed with a low-expansion plastic such as Ryton, preferably with a non-reflective surface, and should be opaque as to the wavelength of the light source to substantially eliminate any background signal from stray reflection of light emitted from the LEDs 5000. The angle Θ may be any angle that minimizes detection of specular reflection and is preferably approximately forty to forty-five degrees. The LEDs 5000 each have a relatively narrow, for example, fifteen degree, projection angle with respect to their emitted light output. The light output from the LEDs 5000 is directed along a light pipe (or collimator) 5600 through an opening 5800 in the top 7200 of the reflectometer case along the slot 7000. The position of the LEDs 5000 along the length of the light pipe 5600 may be adjusted during fabrication of the reflectometer to alter the intensity of target surface illumination and the effects and instances of side reflections within the light pipe. A photo transistor 6000 is mounted within the housing 5200 and oriented along the normal 5400 with respect to the target surface of the strip 2000. The photo transistor 6000 similarly has a relatively narrow, for example, fifteen degree, viewing angle. Light emitted from the target surface of the strip 2000 passes through the opening 5800, and is directed along a light pipe (or collimator) 6200 to the photo transistor 6000. The position of the photo transistor 6000 along the length of the light pipe 6200 may be adjusted during fabrication of the reflectometer to alter the sensitivity and tolerance of reflectometer in reading target surface illumination and color shade. Arrangement of the LEDs 5000 and photo transistor 6000 in the illustrated angle Θ offset and symmetrical orientation serves to minimize specular reflection off the target surface of the strip 2000 and reduce any adverse effects arising from a slightly uneven illumination of the target surface.

Reference is now made to FIGS. 52A and 52B wherein there are shown block diagrams for two embodiments of an electronic circuit for the reflectometer 3000/3000' in accordance with the present invention. A light source 10000 is driven by a square wave current to emit pulses of light 10400 which illuminate a target surface 10600. In one embodiment, as shown in FIG. 52A, the square wave is generated by an oscillator 10200. In another embodiment, as shown in FIG. 52B, the square wave is generated by a microprocessor 14200. As shown in FIGS. 49 and 51, the light source may comprise a pair of LEDs 5000 of the same or different colors. In situations where different colors are used, the LEDs may be pulsed either simultaneously or alternately. The pulses of light 10400 are output from the light source 10000 with a frequency of seventy-five Hertz and a duty cycle of fifty percent. Any frequency may be chosen provided it does not comprise a harmonic or sub-harmonic of AC line voltage, i.e., fifty or sixty Hertz, and is sufficiently high enough to read the target surface and allow for a statistically significant number of reflectivity samples to be taken within an acceptably short measurement period. The target surface 10600 that is illuminated by the light source 10000 may comprise, for example, the membrane 2000 of a transdermal patch 1 like that shown in FIGS. 1A, 1B and 1C and FIG. 2 or the surface of a strip 2000 like that shown in FIG. 47. Alternatively, any other substrate may be illuminated by the light source 10000.

The illuminated target surface 10600 reflects the received light 10400 and thus radiates light 10800 corresponding to the developed color and shade on the target surface 10600 which is detected by an optical detector 11000. As shown in FIGS. 49 and 51, the optical detector 11000 may include a photo transistor 6000. The optical detector 11000 generates in a differential amplifier configuration a pair of differential outputs 11200 and 11600, one-hundred and eighty degrees out of phase from each other, whose peak-to-peak voltages are representative of the detected color and shade of the target surface 10600. The pair of differential outputs 11200 and 11600 are applied to a differential (to unbalanced conversion) amplifier 11400 to generate a single output signal 12200 whose peak-to-peak voltage is representative of the detected color and shade of the target surface 10600. The second output 11600 of the optical detector 11000 is applied to a buffer 11800 before being applied to the differential amplifier 11400. The buffer 11800 output is also applied to an integrator 12000 which compares the signal to a reference voltage and integrates the result of the comparison to generate a DC signal 16200 to bias the optical detector 10000 back to its designed quiescent operating point and thus compensate for any detected ambient (DC) background light. The output 12200 of the differential amplifier 11400 accordingly provides a signal whose peak to peak voltage level is indicative of the color and shade of the target surface, when the light source is illuminated, as opposed to any color or shade that relates to the effects of ambient DC light at the target surface, when the light source is off.

The output 12200 of the differential amplifier 11400 is then applied to a synchronous detector 12400. The synchronous detector 12400 also receives the light source 10000 drive signal which is output from the oscillator 10200 and obtains information concerning when the light source 10000 is illuminating, and not illuminating, the target surface. As this illumination is being detected by the optical detector 11000, and since the signal output 12200 from the differential amplifier 11400 is affected by the detected illumination, the synchronous detector 12400 may then process the output 12200 to full wave rectify the signal output 12200 from the differential amplifier 11400 and produce a substantially steady DC voltage that is indicative of the color or shade of color at the target surface. The output 12600 from the synchronous detector 12400 is then low pass filtered to remove any included high frequency components resulting from the synchronous detection process before any subsequent processing occurs.

Positioned adjacent to the light source 10000, perhaps with some included thermo-mechanical coupling, is a temperature sensor 12800. The temperature sensor 12800 generates an output 13000 that is indicative of temperature at or near the light source. This information is important to consider in situations where the brightness and intensity of the light 10400 emitted from the light source 10000 varies with changes in temperature. Any experienced brightness or intensity changes in the emitted light 104000 cause corresponding changes in the output signal 12600. With knowledge of temperature indicative information, appropriate actions can be taken during subsequent processing of the signal 12600 output from the synchronous detector 12400 in order to account for the temperature driven variations in emitted light and the corresponding variations in the output signal 12600.

Reference is now specifically made to FIG. 52A. In accordance with a first embodiment of the present invention, the previously described components of the reflectometer 3000/3000' are contained within a case, such as the hand held or desk top units described above. The reflectometer 3000/3000' outputs the signal 12600 and the signal 13000 through an external port connection 13200 and over a communications link 13400 to a personal computer 136, separate and apart from the case for the reflectometer 3000/3000', where the signal are processed. The communications link 13400 may comprise, for example, multi-wire cable if the reflectometer 3000/3000' is proximately located to the personal computer 13600, or a telephone line or infra-red transceiver if the reflectometer is remotely located to the personal computer 13600. A PC/MCIA card (not shown) may be utilized to interface the reflectometer 30/30' to the personal computer 13600. It will, of course, be understood that suitable equipment, not shown but well known to those skilled in the art, must also be included to interface the reflectometer 3000 to a telephone line. In the personal computer 13600, the received signals 12600 and 13000 are converted by a internal digital-to-analog converter 13800 to digital values. These digital values are then processed by an internal processing unit 14000 to generate information concerning analyte concentration level. The detected concentration information is then displayed by the personal computer 13600 on its display screen and stored in computer memory for later retrieval, consideration, analysis and transfer. In this embodiment, the signals output from the "READ" button 3600, "SCROLL" button 4000 and "SELECT" button 4200, see FIG. 48A, of the reflectometer 3000/3000' are also transmitted through the external port connection 13200 and over the communications link 13400 to the personal computer 13600.

Reference is now specifically made to FIG. 52B. In accordance with a second embodiment of the present invention, all the required reading and processing components of the reflectometer 3000/3000' are advantageously contained within a case, such as the hand held or desk top units described above. This provides for a self-contained, portable device. The signal 12600 and the signal 13000 are presented to a microprocessor 14200 located within the reflectometer 3000/3000' case. The microprocessor 14200 includes an analog-to-digital conversion functionality 14400 for converting the analog signals 12600 and 13000 to digital values. These digital values are then processed by the microprocessor 14200 to generate information concerning detected analyte concentration level. The detected concentration information is then displayed by the reflectometer 3000/3000' on the liquid crystal display 3800 and stored in the microprocessor 14200 memory 14600 for later retrieval, consideration and transfer. An external port connection 14800 is provided through the microprocessor 14000 in order to allow for the communication of the detected concentration information over a communications link 13400 to a personal computer 13600. The communications link 13400 may comprise, for example, multi-wire cable if the reflectometer 3000/3000' is proximately located to the personal computer 13600, or a telephone line if the reflectometer is remotely located to the personal computer 13600. Preferably, the microprocessor 14200 includes the appropriate circuitry for interfacing the reflectometer 3000/3000' to a telephone line. As an alternative, the microprocessor 14200 may utilize the light source 10000 to allow for the communication of the detected concentration information over an optical communications link, such as an infra-red connection. In this embodiment, the processor appropriately modulates the light source with the detected concentration information to effectuate a data communication.

The "READ" button 3600, "SCROLL" button 4000 and "SELECT" button 4200, see FIG. 48A, are connected as inputs to the microprocessor 14200. Using the "READ" button 36000, the user activates the reflectometer 3000/3000' to make a measurement of color shade. The liquid crystal display 3800 then provides a numerical output to the user that is indicative of the color shade or of some measurable quantity or quality related to that read color shade. Using the "SCROLL" button 4000 and "SELECT" button 4200, the user may set date and time of day information, request current date and time of day information, program alarms which alert the user as to when it is necessary to take a reading, enter reflectometer data, such as a manufacturing batch code for the transdermal patch 1, or input color/shade data for calibrating the reflectometer, and select the type of testing to be performed, for example, glucose versus cholesterol. A speaker 15000 is connected to the microprocessor 14200 to provide audible signals to the user, such as an alarm.

Reference is now made to FIGS. 53A-1, 53A-2, 53B-1 and 53B-2 wherein there are shown circuit diagrams for an analog portion of the reflectometer of the present invention, as illustrated in FIGS. 52A and 52B, respectively. The square wave oscillator 10200 in the embodiment of FIG. 52A comprises a conventional LM555 timer integrated circuit 15100 configured with appropriately connected resistors and capacitors to generate a square wave output on line 15200 at a selected frequency, for example, about seventy-five Hertz, and with a selected duty cycle, for example, about fifty percent. Alternatively, the square wave is generated by the microprocessor 14200 in the embodiment of FIG. 52B and supplied by a buffer 10200' for output on line 15200. The square wave output on line 15200 is applied to a pair of series connected LEDs 5000, which emit pulses of light, and a light level adjustment circuit 15400 comprising a potentiometer 15600 within the light source 10000.

The adjustment provided through use of the potentiometer comprises a factory performed adjustment to set the level or intensity of pulsed light output from the LEDs 5000 for the reflectometer 3000/3000'. More specifically, the adjustment comprises a first order calibration of the reflectometer 3000/3000'. A more complete explanation of how this calibration process is executed is provided below.

The modulated light is reflected from a target surface and detected (with minimal spectrally reflected components) by the optical detector 11000. This optical detector 11000 includes a photo transistor 6000 differentially connected to another transistor 15800, wherein the differentially connected photo transistor and other transistor share substantially similar operating characteristics. By differential connection it is meant that the emitters of the photo transistor 6000 and the transistor 15800 are connected to each other. The base of the transistor 15800 is driven by a signal output from a voltage divider circuit 16000 to set the quiescent operating point of the detector 11000. The base of the photo transistor 6000 is driven by a feedback signal, to be described in more detail below, on line 16200 in order to bias the photo transistor back to the optimum quiescent operating point and, thus, account for the detection of ambient DC light. A current mirror circuit 16400 supplies a fixed constant current to the connected emitters of the photo transistor 6000 and the transistor 15800 in the differential connection.

The photo transistor 6000 generates a first differential output signal 11200 at its collector. The transistor 15800 generates a second differential output signal 11600 at its collector. The first and second differential output signals 11200 and 11600 are one hundred eighty degrees out of phase with each other and each have a peak to peak voltage that is representative of detected light, including its color and shade, which is reflected from the target surface. The second differential output signal 11600 is applied to a buffer 11800 comprising a voltage follower connected operational amplifier 16600. The signal 11600 output from the buffer 11800 is applied to the integrator 12000 which comprises an integrator connected operational amplifier 16800. The integrator 12000 makes a comparison of the buffered signal 11600 to a DC reference voltage, and integrates the result of that comparison to generate the feedback signal on line 16200 whose voltage is proportional to a detected error between the desired quiescent operating point of the optical detector 11000 and an average voltage shift therein caused by ambient (DC) light detected by the photo transistor 6000, temperature variations in the differential pair and other external factors, like component aging. The generated feedback signal on line 16200 is then applied to the base of the photo transistor 6000 to bias the component back to the preferred quiescent operating point and thus account for these external factors, in the peak to peak voltages of the generated first and second differential output signals 11200 and 11600, which would otherwise result in measurement errors with respect to the color and shade detection of the reflected pulsed light emitted from the light source 10000.

The first and second differential output signals 11200 and 11600 are applied to the differential amplifier 11400 comprising a differentially connected operational amplifier 17000. The differential amplifier 11400 subtracts the first differential output signal from the second differential output signal to provide a single output signal 12200 on line 17200 having a peak to peak voltage that is representative of detected light, including its color and shade, which is reflected from the target surface. Any DC components within this output signal 12200 are removed by a DC blocking capacitor 17400. The remaining AC components, comprising generally speaking a square wave whose peak to peak voltage is proportional to the reflected light detected by the photo transistor 6000 and representative of the color and shade characteristics of that light, is then applied to the synchronous detector 12400.

The synchronous detector 12400 receives the square wave signal output from the square wave oscillator 10200 and uses it to perform a synchronous full wave rectification of the output signal 12200 (demodulation) to produce a substantially steady DC voltage indicative of the color or shade of color at the target surface. This synchronous detection process further functions to eliminate any shifts in the output signal 12200 caused by ambient (AC) light, for example, from fluorescent light, detected by the photo transistor 6000. More specifically, the synchronous detector 12400 functions to produce the substantially steady DC voltage which accurately measures the peak to peak AC voltage of the output signal 12200 derived from the optical detector without being subject to any DC effects.

The synchronous detector 12400 includes an operational amplifier 19200 that is selectively configured, based on the received square wave signal, to provide for either inverting or non-inverting unity gain processing of the output signal 12200. This functionality is provided through the actions of a plurality of CMOS switches. A first CMOS switch 18000 buffers and phase inverts the square wave signal, and drives a second CMOS switch 18200 and a third CMOS switch 18400. The second CMOS switch 18200 functions as a phase inverter, such that the first and second CMOS switches generate square wave output signals on line 18600 and 18800 that are one-hundred eighty degrees out of phase with each other. One of those signals (line 18800) is applied to the third CMOS switch 18400, and the other one of the signals (line 18600) is applied to a fourth CMOS switch 19600. The third CMOS switch 18400, when activated by the line 18800 signal, connects the non-inverting input of the operational amplifier 19200 to a reference ground supplied by diode 23800. The fourth CMOS switch 196000, when activated by the line 18600 signal, connects the non-inverting input of the operation amplifier 19200 to receive the DC blocked output signal 12200. The output signal 12200 is further provided to the inverting input of the operational amplifier 19200.

When the third CMOS switch 18400 is activated, the fourth CMOS switch 19600 is not activated. Due to the grounding of the non-inverting terminal, the operational amplifier 19200 is configured to provide for unity gain inverted processing of the output signal 12200. Conversely, when the third CMOS switch 18400 is activated, the fourth CMOS switch 19600 is not activated. Due to the lifting of the ground and the connection of the output signal 12200 to the non-inverting and inverting terminals, the operational amplifier 19200 is configured to provide for unity gain non-inverted processing of the output signal 12200. By appropriately phasing the square wave signal application to control CMOS switch activation, a synchronous full wave rectification of the output signal 12200 is provided.

Operation of the synchronous detector 12400 of the present invention to provide for synchronous full wave rectification may be better understood by reference to FIGS. 54A and 54B. In FIG. 54A, there is shown the waveform 21000 for the output signal 12200 as received by the synchronous detector 12400. The waveform 21000 includes a positive portion 21200 and a negative portion 21400 with a peak to peak voltage that is indicative of the color or shade of color at the target surface. Responsive to the square wave signal (correctly phased), the third CMOS switch is activated to ground the non-inverting terminal, and the operational amplifier 19200 thus is configured to provide non-inverting unity gain processing of the output signal 12200 during the positive portion 21200. Next, again responsive to the square wave signal (correctly phased), the fourth CMOS switch is activated to connect the output signal 12200 to the non-inverting terminal and the operational amplifier 19200 thus is configured to provide inverting unity gain processing of the output signal 12200 during the positive portion 21400. The switching of the third and fourth CMOS switches continues as driven by the square wave signal. The result of this selective processing is to generate the output signal 12600 on line 20800, as shown in FIG. 54B, having a substantially steady DC voltage indicative of the color or shade of color at the target surface. The waveform 22000 includes a first portion 22200 corresponding to the non-inverted (positive) portion 21200 of the output signal 12200, and a second portion 22400 corresponding to the inverted (negative) portion 21400 of the output signal 12200. It is noted that the waveform 22000 still further includes a slight negative spike 21600 at each point where the output signal from the square wave oscillator 10200 switches between low and high due to the CMOS switch effects.

With reference now once again to FIGS. 53A-1, 53A-2, 53B-1 and 53B-2, the output signal 12600 on line 20800 is filtered by an R-C first order low pass filter to remove the slight negative spikes 21600 within the waveform 22000. The resulting filtered output signal 12600 is then provided as a first analog signal output from the analog portion of the reflectometer 3000/3000' for subsequent digital processing, see FIGS. 52A and 52B).

The diode 23800 introduced DC level shift affects the DC voltage level of the output signal 12600 from the synchronous detector and, hence, the first analog signal output from the analog portion of the reflectometer 3000/3000'. The DC level shift therefore must be accounted for in order to ensure that the output first analog signal is properly interpreted to detect color and shade at the target surface. More specifically, the DC level shift must be subtracted from the output signal 12600. Thus, the DC level shift voltage is output on line 24000 as a second analog signal output from the analog portion of the reflectometer 3000/3000' for subsequent digital processing. This may be performed during digital processing or, alternatively, taken care of in the analog portion of the reflectometer 3000/3000' by utilizing a differential amplifier (not shown) to perform the subtraction of the second analog signal from the first analog signal prior to any subsequent digital processing.

As discussed above, the reflectometer 3000/3000' further includes a temperature sensor 12800. It is recognized that the LEDs 5000 are temperature sensitive components with respect to their light output. In order to be able to accurately track operational changes due to temperature variation, the temperature sensor 12800 preferably comprises a diode 23000, having operational characteristics complementing those of the LEDs 5000, thermo-mechanically coupled to the LEDs 5000 and electrically connected between ground and the line 15200 square wave output from the oscillator 10200 through a level adjustment circuit 23200 comprising a potentiometer 23400. This adjustment comprises a factory performed adjustment to set a level for the temperature indicative voltage output from node/line 23600. The temperature indicative voltage on line 23600 thus comprises a third analog signal output from the analog portion of the reflectometer 3000/3000' for subsequent digital processing.

Reference is now once again made to FIGS. 52A and 52B. The first analog signal output, after subtracting the second analog signal output, and the third analog signal output from the analog portion of the reflectometer 30/30' are next digitally processed. More specifically, the DC voltage of the first analog signal representative of the detected reflected light at the target surface, and indicative of color and shade, is analog-to-digital converted to a first digital value. Similarly, the DC voltage of the third analog signal representative of temperature is analog-to-digital converted to a second digital value. The first and second digital values are then processed to calculate a compensated voltage that directly relates to the color and shade of the non-spectral reflectance off the target surface at standard conditions. The processor, by use of a stored lookup table that correlates a certain compensated voltage, indicative of target surface color and shade, to a certain analyte concentration, or through the use of an appropriate mathematical formula, identifies an analyte concentration level output value. The user selection of reflectometer data, such as a manufacturing batch code for the transdermal patch 1 or testing strip 2000, and type of testing to be performed, for example, glucose versus cholesterol, identifies which one of a plurality of stored lookup tables or formulae should be considered by the processor in evaluating the compensated voltage indicative of target surface color and shade to determine the corresponding analyte concentration level output value.

As discussed briefly above, the intensity of the light output from the LEDs 5000 is affected by ambient temperature. As temperature increases, the intensity of the light output decreases. Conversely, as temperature decreases, the intensity of the light output increases. Accounting for any temperature changes at the light source is thus imperative in order to ensure that the detected steady DC voltage is an accurate representation of color and shade.

A number of different temperature sensing mechanisms may be utilized. In accordance with a first one of those mechanisms, it is recognized that the LEDs 5000 are diodes, and that the diode 23000 may be advantageously used as a temperature sensor which mimics the temperature sensitive operation of the LEDs. The voltage drop across the diode is affected by temperature in the same way the light intensity output from the LEDs 5000 is affected by temperature. With a measurement of this voltage drop in comparison to a reference voltage drop at a known temperature, it is possible to determine current temperature.

As an example, the temperature dependance of the voltage drop ($V_{dC}$) of a small signal diode (such as 1N4148) is measured to be approximately 0.0021 volts/degree C. At factory calibration of the reflectometer 3000/3000', the forward voltage drop across the diode 23000 is set by adjustment to the potentiometer 23400 to, for example, 0.609 volts at twenty-five ° C. Once this baseline voltage drop is established, any measured difference between the actual voltage drop and the baseline voltage drop can be easily converted into a temperature variation, and that determined temperature variation accounted for in evaluating both the operation of the LEDs 5000 and the first analog output signal.

In this regard, it is noted that the temperature effect on the light intensity output from the LEDs 5000 varies with the detection signal nearly linearly over the limited temperature range of interest with respect to the reflectometer 3000/3000'. A plot of the temperature error in volts versus the reflectance, i.e., the first analog signal representative of the detected reflected light at the target surface and indicative of color and shade, accordingly reveals a substantially straight line that intersects the origin and has a positive slope of substantially 0.0035 volts/° C. (hereinafter k1). The voltage adjustment ($\Delta V$) that must be made to account for changes in temperature from a standard may be calculated as follows:

$$\Delta V = k1 \times SV \times \Delta C$$

wherein: SV is the signal representative of the detected reflected light at the target surface and indicative of color and shade; and $\Delta C$ is the sensed temperature change, i.e., detected offset, from a reference standard of twenty-five ° C., and is equal to:

$$\Delta C = \frac{V_{dt} - V_{dr}}{V_{dC}}$$

wherein: $V_{dt}$ is the currently measured voltage drop across the diode; and $V_{dr}$ is the voltage drop across the diode at a reference standard of twenty-five ° C.

The compensated voltage CV, which accounts for the effects of temperature, may be calculated through the use of standard mathematical manipulations, the compensated voltage may be calculated as follows:

$$CV = SV \times (1 - k2 \times (V_{dt} - V_{dC}))$$

wherein: k2 is a constant equal to $k1/V_{dC}$.

In the case of the specific example signal diode mentioned above, k2 equals 0.0035/0.0021=1.667.

Reference is now made to FIG. 55A wherein there is shown a circuit diagram illustrating a second temperature sensing mechanism useful in compensating for temperature. In this implementation, direct first order compensation for the variations in light intensity due to temperature is provided. One or two diodes 23000' are connected in series with each other and the LEDs 5000 between the square wave output on line 15200 and the light level adjustment circuit 15400 comprising the potentiometer 15600. The diodes 23000' are, like the diode 23000, thermo-mechanically coupled to the LEDs 5000. The voltage drop across the series connected diodes 23000' with increased temperature results in the application of increased current to the LEDs 5000. This increased current application provides a first order compensation for any diminishment in light intensity output from the LEDs 5000 due to increasing temperature. For this series diode 23000' compensation scheme, it is preferable to use a germanium or Schottky diode since the low forward voltage drop of these types is an advantage in controlling the sensitivity of the light-adjusting potentiometer 15600. This series diode 23000' compensation scheme may also be utilized in combination with the diode 23000 sensor configuration illustrated in FIGS. 53A-1, 53A-2, 53B-1 and 53B-2 to provide for improved temperature detection and compensation.

Reference is now made to FIG. 55B wherein there is shown a circuit diagram illustrating a third temperature sensing mechanism useful in compensating for temperature. In this implementation, a measurement of voltage drop is taken across one of the LEDs 5000, across each of the LEDs, or across all of the LEDs. Using this measured instantaneous LED voltage drop, dynamic temperature compensation may be implemented to account for not only currently experienced temperature variations, but also long term degradation of the LEDs 5000. In connection with the reflectometer 3000/3000' illustrated in FIG. 52A, a voltage drop detector 25200 is provided to measure the voltage drop across one, each or all of the LEDs 5000. The measured voltage drop may then be output through the external port connection for processing by the personal computer in accordance with the CV equation discussed above. In connection with the reflectometer 3000/3000' illustrated in FIG. 52B, on the other hand, a pair of analog taps 25400 are taken off the anode/cathode leads of one, each or all of the LEDs 5000 and input to the microprocessor. The analog to digital converter of the microprocessor then converts the measured voltages to digital signals, subtracts the values from each other and determines a resulting voltage drop for subsequent processing in accordance with the CV equation discussed above.

With reference now once again to FIGS. 53A-1, 53A-2, 53B-1 and 53B-2, a fourth temperature sensing mechanism useful in compensating for temperature advantageously utilizes the synchronous detector DC level shifting diode 23800 to measure temperature by sensing the voltage drop across the diode. In one configuration, the diode 23800 may be thermo-mechanically coupled to the LEDs 5000 to provide light source related temperature information for subsequent processing in accordance with the CV equation discussed above.

In another configuration, the diode 23800 may remotely located from any heat sources within the reflectometer 3000/3000' in order to provide ambient temperature information for subsequent processing in connection with evaluations which are dependent on knowing ambient, as opposed to light source temperature. As an example, the biological and chemical reactions on the transdermal patch and/or strip are ambient temperature dependent. In order to calculate accurate incubation times, the diode 238 ambient temperature data may be processed to identify when is the proper time to take a reading.

Reference is now once again made to FIGS. 48A, 48B and 49. As discussed above, the reflectometer 3000/3000' is minimally affected by the external influence of light, induced noise, and temperature. Accordingly, the cylindrical shaped protruding nose 4800 portion of the sensor head 3200 need not necessarily provide a light-tight fit with the opening 33 in the transdermal patch 1 because leakage of ambient light, just like skin color, is compensated for by the synchronous detection feature. Internally, the alternating nature of the light source and detector circuit is not subject to DC drift. Furthermore, temperature compensation concerns have also been addressed through the use of temperature detection and compensation circuitry and processing as discussed above.

There are, however, other factors that can effect the accuracy of the color and shade reading. For example, the unsteady operation of the reflectometer 3000 due, for example, to a rocking motion or other movement, may alter the illumination geometry at interface between the sensor head 3200 and the transdermal patch 1. Another concern is the application of varying degrees of contact pressure between the reflectometer 3000 and the transdermal patch 1. With specific respect to a hand-held device, it is vitally important that the routine to measure a repeatable peak hold on the output signal indicative of detected color and shade must be tolerant of vibrations and unsteady operation. To achieve this goal, data is sampled at a high enough rate such that as many data points as practical are input into an averaging routine. The technique for averaging these samples should be able to determine the correct reading within a few seconds and not be affected however by the time to take a reading.

Peak detection voltage stability is utilized as the test for insuring a repeatable result. If, for example, the detection voltage range is between 0.5 and 0.8 volts, then a peak detection voltage stability of 0.002 volts would provide for better than one percent resolution. A signal gain of five would result in a range of two and half to four volts, a range that is more compatible with a microprocessor having an analog to digital converter with a five volt supply.

Reference is now made to FIGS. 56 and 59 wherein there is shown an exemplary operation of the peak hold detection algorithm used in processing the DC voltage of the first analog signal representative of the detected reflected light at the target surface, and indicative of color and shade.

Raw data relating to un-compensated voltage is collected at a certain sampling rate (step 50000). A moving block average (Av(i)) is then calculated for the last n samples (step 50200). The moving block average Av(i) is then compared in step 50400 to the most recent previous moving block average (Av(i−1)). If the deviation between the current moving block average Av(i) is less than a certain deviation voltage threshold from the most recent previous moving block average Av(i−1), then a steady state condition has been satisfied, and the current moving block average Av(i) is held as a peak value in step 506oo for subsequent processing as the steady DC voltage indicative of the color and shade of the target surface. If the step 50400 measured deviation exceeds the certain deviation voltage threshold, the process returns to step 50200 to calculate a new current moving block average. The process continues sampling (step 50000), calculating moving block averages (step 50200), and comparing (step 50400) until the determined deviation between the current moving block average Av(i) and the most recent previous moving block average Av(i−1) is less than a certain deviation voltage threshold.

The held peak value for the steady DC voltage is then processed first to adjust for the DC offset, then to correct for temperature, and then to adjust for color and/or batch calibration, if desired or necessary. The resulting compensated voltage directly relates to the color and shade of the reflectance off the target surface at standard conditions. The processor, by use of a stored lookup table or mathematical formula, based perhaps upon lookup table related data, that correlates a certain compensated voltage, indicative of target surface color and shade, to a certain analyte concentration, identifies an analyte concentration level output value. If the compensated voltage value falls between two rows in the lookup table, the end data points for the analyte concentration level are interpolated to produce an output. The user selection of reflectometer data, such as a manufacturing batch code for the transdermal patch 1 or testing strip 2000, and type testing to be performed, for example, glucose versus cholesterol, identifies which one of a plurality of stored lookup tables should be considered by the processor in evaluating the compensated voltage indicative of target surface color and shade to determine the corresponding analyte concentration level output value. Other factors that may affect the calibration to an individual can also be affected by the choice of the lookup table. An example of a lookup table suitable for use in the reflectometer of the present invention is illustrated in FIG. 57.

In the context of the lookup table of FIG. 57, or its equivalent mathematical formula, an example of the use of the reflectometer 3000/3000' to monitor glucose level is now presented. At 10:00 am, a pre-set audible alarm alerts the diabetic patient to take a glucose reading. A transdermal patch 1 is attached to the inside of the patient's forearm and the SELECT button is pressed, signaling the beginning of an incubation countdown period. After the period expires, another audible alarm having a distinct tone sequence alerts the patient that it is time to take a reading on the patch 1. The cylindrical shaped protruding nose 4800 portion of the sensor head 3200 is inserted within the opening 33 in the transdermal patch 1, and the READ button is pushed. After about one second of reading time, the first analog output signal has not yet reached a steady state condition, relative to the certain deviation voltage threshold. After about two seconds, steady state is reached and a DC offset adjusted, but temperature uncompensated, voltage is obtained with a value of 0.664 volts. This steady DC voltage is then presented to the processor as the first analog output signal for analysis. In addition, the temperature sensor diode 23000 provides the third analog output signal with a value of 0.611 volts. In accordance with the temperature correction algorithm described above, a compensated voltage CV indicative of target surface color and shade is then calculated at 0.662 volts. If necessary, appropriate color and/or batch calibration adjustment may also be made. In the lookup table of FIG. 57, or its equivalent mathematical formula, this compensated voltage correlates with a glucose level of between 14000 and 180 mg/dL. Interpolation of these two end points produces a final result of 170.4 mg/dL. This glucose level is then rounded to the nearest whole number, and a final result of 170 mg/dL is displayed to the patient. The result is also stored in memory along with the date and time for future reference or to be downloaded to a computer as patient history.

Reference is now made to FIG. 58A wherein there is shown a cross-sectional view illustrating an improper engagement of the reflectometer and the transdermal patch. As mentioned previously, one of the factors that can affect the accuracy of the color and shade reading is the application of varying degrees of contact pressure between the reflectometer 3000 and the transdermal patch 1. In this regard, it is noted that accurate measurement is dependent upon the target surface being in proper position. Uneven or excessive pressure can, however, distort, i.e., bow or ripple, the membrane 20 and move the target surface out of proper position. This effect is shown in exaggerated fashion in FIG. 58A. It has been observed that the result of increasing pressure applied to the patch by the reflectometer meter causes an increased reflectance signal due to the target surface deflecting toward the photo transistor. Furthermore, in some instances the membrane is inherently distorted or is distorted as a result of the biological and chemical reaction.

Reference is now made to FIG. 58B wherein there is shown a cross-sectional view illustrating the use of a window 29000 on the cylindrical shaped protruding nose 4800 portion of the reflectometer sensor head 3200. The window 29000 serves to flatten out any existing distortions, bows, ripples and the like, in the membrane 20 and further render the measurement process relatively insensitive to variations in applied pressure. The target surface is accordingly accurately positioned for color and shade reading. The window 29000 is transparent and is preferably made of a plastic or glass that exhibits a high transmissivity at the wavelength of the light source light used, in this case, that wavelength emitted by the LEDs 5000. Additional requirements include durability and resistance to cleaning solutions and scratching. As an added benefit, the clear window 29000 prevents dirt, dust and debris, which could reduce the sensitivity of the reflectometer and might also affect the calibration, from entering and accumulating within the sensor head.

Reference is now made to FIG. 58C wherein there is shown a cross-sectional view illustrating the use of a tapered cylindrical shaped nose portion 4800' of the reflectometer sensor head 3200. As discussed above, the reflectometer 3000/3000' is substantially immune to the external influence of light. Accordingly, the nose portion 4800/4800' of the sensor head 3200 need not necessarily provide a light-tight fit within the opening 33 in the transdermal patch 1. Leakage of ambient light, just like skin color, is compensated for by the included feedback signal and synchronous detection features. However, it is important, as illustrated in FIG. 58A, that the target surface be placed in proper position with respect to the head 4800/4800'. A cylindrical shaped sensor head 4800, like that shown in FIGS. 49, 58A and 58B, having a diameter nearly identical to the diameter of the circular opening in the transdermal patch 1 may not, in instances where the user is not careful, seat itself properly within the opening flush against the membrane. As an additional concern, the top surface of the transdermal patch may have an adhesive layer that could catch the nose making it more difficult to properly seat the nose within the patch opening. To assist the user in obtaining proper flush positioning of the reflectometer 3000, the tapered shape of the cylindrical shaped nose portion 4800' of the reflectometer sensor head 3200 functions to find the opening in the patch 1 during insertion and facilitate proper placement of the reflectometer against the membrane. The window 29000 is preferably recessed into the nose by its thickness to seal the opening in the sensor head and prevent the edge of the window from being caught and possibly damaged or removed during handling.

Reference is now once again made to FIGS. 52A and 52B. As mentioned previously, the reading process is initiated by having the user depress the SELECT button. This button signals the beginning of an incubation countdown period. It is recognized that the time required for completion of the biological and chemical processes that occur on the patch 1 or strip 2000 may be temperature dependent. Thus, the processor of the reflectometer 3000/3000' utilizes the diode 23800 to obtain information indicative of ambient temperature. When the SELECT button is activated, the processor uses the current ambient temperature information provided by the diode 23800 to determine an incubation countdown period of sufficient length to insure completion of the biological and chemical processes on the patch 1 or strip 2000 before signaling the user with an audible alarm indicating that it is time to take a reading.

Reference is now made to FIGS. 53A-1, 53A-2, 53B-1 and 53B-2 and to FIG. 60 wherein there is shown a flow diagram illustrating a process for performing a first order calibration of the reflectometer 3000/3000'. It is noted that this first order calibration must be performed at a controlled temperature, such as twenty-five ° C. A point on the compensated voltage-analyte concentration curve, such as that represented by the lookup table of FIG. 57, is chosen in step 35000 where it is preferred that the reflectometer be able to read most accurately. In most instances this point will be at or close to midrange on the curve. The reflectometer 3000/3000' is then exposed in step 35200 to a standard color shade that corresponds with that chosen analyte concentration. A resulting compensated voltage or analyte concentration values is then output in step 35400. The internal potentiometer 15600 of the light level adjustment circuit 15400 is then adjusted in step 35600, with an adjusted compensated voltage being output in step 35800. A test is then made in step 36000 to determine whether the step 35600 adjustment produced an adjusted compensated voltage in step 35800 that matches the step 35000 selected point on the compensated voltage-analyte concentration curve. If not, the process returns to perform steps 35600, 35800 and 36000 over again. This is repeated until such time as the potentiometer 15600 adjustment produces an adjusted compensated voltage that matches the compensated voltage at the selected point on the compensated voltage-analyte concentration curve. If this first order calibration process is performed with respect to each reflectometer 3000/3000', then each reflectometer will read exactly the same way at the midpoint, thus providing consistency in reflectometer operation from device to device.

Reference is now made to FIGS. 52A and 52B and to FIG. 61 wherein there is shown a flow diagram illustrating a process for performing a second order calibration of the reflectometer 3000/3000'. It is noted that this second order calibration must be performed at a controlled temperature, such as twenty-five ° C. A point on one end of the compensated voltage-analyte concentration curve, such as that represented by the lookup table of FIG. 57, is chosen in step 37000. The reflectometer 3000/30' is then exposed in step 37200 to a standard color shade that corresponds with that chosen analyte concentration. A resulting compensated voltage value is then output in step 37400. A first end point offset between the output compensated voltage value and the compensated voltage at the selected end point on the compensated voltage-analyte concentration curve is then determined in step 37600 and stored, in non-volatile memory, by the processor in step 37800. At this point, a measurement is also made of the voltage drop across the temperature sensor 12800 diode 23000 and stored, in non-volatile memory, by the processor in step 36200. A point on the other end of the compensated voltage-analyte concentration curve is then chosen in step 38000. The reflectometer 3000/3000' is then exposed in step 38200 to a standard color shade that corresponds with that chosen analyte concentration. A resulting compensated voltage value is then output in step 38400. A second end point offset between the output compensated voltage value and the compensated voltage at the selected end point on the compensated voltage-analyte concentration curve is then determined in step 38600 and stored, in non-volatile memory, by the processor in step 38800. A point in the middle of the compensated voltage-analyte concentration curve is then chosen in step 39000. The reflectometer 3000/3000' is then exposed in step 39200 to a standard color shade that corresponds with that chosen analyte concentration. A resulting compensated voltage value is then output in step 39400. A mid-point offset between the output compensated voltage value and the compensated voltage at the selected end point on the compensated voltage-analyte concentration curve is then determined in step 39600 and stored, in non-volatile memory, by the processor in step 39800. The stored first and second end point offsets and mid-point offset may then be taken into account by the processor in using the stored lookup table, or mathematical algorithm, which correlates a certain compensated voltage, indicative of read target surface color and shade, to a certain analyte concentration, to identify an analyte concentration level output value. Although not specifically illustrated, more than two or three points on the curve may be selected for second order calibration in order to provide for more accurate operation.

It is noted that the second order calibration process of FIG. 61 may be performed multiple times on a single meter in situations where the meter is likely be utilized to make readings for different types of tests, for example, glucose and cholesterol. In such a case, the reflectometer 3000/3000' is programmed with plural stored lookup tables, or mathematical algorithms, which each correlate a certain compensated voltage, indicative of read target surface color and shade, to a certain analyte concentration. The reflectometer must be calibrated to applicable data for each of those tests in order to ensure proper performance.

It is recognized that the color indications developed on the transdermal patches or strips may vary between manufacturing batches. One way to handle this concern is to code each batch in accordance with its color indications. Each meter is then preprogrammed with the batch code designations and appropriate offsets at the first and second end points and mid-point. In situations where preprogramming in this manner is not possible, the process illustrated in FIG. 61 may be performed by the patient, as opposed to at the factory, with respect to each batch of transdermal patches or strips used. To support this patient batch code (third order) calibration process, each batch of transdermal patches or strips would include three standard color shades, with each shade corresponding with a certain analyte concentration as measured by that batch. After completion of the process, stored first and second end point offsets and mid-point offset relating to batch variation may then be taken into account by the processor in using the stored lookup table, or mathematical algorithm, which correlates a certain compensated voltage, indicative of read target surface color and shade, to a certain analyte concentration, to identify an analyte concentration level output value.

Reference is now made to FIG. 57 and to FIG. 62 wherein there is shown a graph illustrating an exemplary compensated voltage-analyte concentration curve 40000 and the affect thereon of the first and second order calibration processes of FIGS. 60 and 61, respectively. The curve 40000 represents the relationship between a certain measured compensated voltage, on the y-axis, and a corresponding analyte concentration, on the x-axis. More precisely, the curve 40000 presents the specific compensated voltage-analyte concentration relationship illustrated in FIG. 57.

Turning first to the first order calibration process of FIG. 60, a mid-point 40200 on the curve 40000 of FIG. 62 is selected, in this instance representing an analyte concentration of 30000 mg/dL. The reflectometer is then exposed to a standard color shade that corresponds with that chosen analyte concentration. Instead of producing a corresponding expected compensated voltage 40400 reading (in this instance comprising 550 mV), the reflectometer reports a different compensated voltage 40600. Appropriate potentiometer 15600 adjustment is then performed in order to bring the reflectometer reported compensated voltage 40600 into a matching relationship with the expected compensated voltage 40400. Storage is also made at this point of the voltage drop across the temperature sensor 12800 diode 23000.

Turning next to the second order calibration process of FIG. 61, a first end point 40800 on the curve 40000 of FIG. 62 is selected, in this instance representing an analyte concentration of 625 mg/dL. The reflectometer is then exposed to a standard color shade that corresponds with that chosen analyte concentration. Instead of producing a corresponding expected compensated voltage 41000 reading, in this instance comprising 400 mV, the reflectometer reports a different compensated voltage 41200. The offset d1 between the expected compensated voltage 41000 and the reflectometer reported compensated voltage 41200 is determined and stored. A second end point 41400 on the curve 40000 is selected, in this instance representing an analyte concentration of 55 mg/dL. The reflectometer is then exposed to a standard color shade that corresponds with that chosen analyte concentration. Instead of producing a corresponding expected compensated voltage 41600 reading, in this instance comprising 850 mV, the reflectometer reports a different compensated voltage 41800. The offset d2 between the expected compensated voltage 41600 and the reflectometer reported compensated voltage 41800 is determined and stored. A mid-point 42000 on the curve 40000 is selected, in this instance representing an analyte concentration of 300 mg/dL. The reflectometer is then exposed to a standard color shade that corresponds with that chosen analyte concentration. Due to the first order calibration provided above, the reflectometer should produce the expected compensated voltage 40400 reading, in this instance comprising 550 mV. If it does not, then the first and second order calibration processes should be performed again. In the event the reflectometer is being programmed for use in connection with different types of tests, for example, glucose and cholesterol, the reflectometer likely will not produce the expected compensated voltage 40400 reading. Rather, the reflectometer reports a different compensated voltage 40600. The offset d3 between the expected compensated voltage 40400 and the reflectometer reported compensated voltage 40600 is determined and stored. The stored first and second end point offsets d1 and d2 and mid-point offset d3 may then be taken into account by the processor in using the stored lookup table, see FIG. 57, or mathematical formula when processing a detected compensated voltage, indicative of read target surface color and shade, to identify an analyte concentration level output value. The result of this second order calibration is, in effect, to produce an adjusted compensated voltage-analyte concentration curve 40000', illustrated with a dashed line, for each type of test that takes into account the tolerances of the specific reflectometer 3000/3000' at issue. In processing the reflectometer 3000/3000' detected compensated voltage at points on the curve 40000, look-up table of FIG. 57, between the end-points 40800 and 41400, an interpolation of the appropriate d1, d2 or d3 offset may be calculated, along with any interpolation necessary to make the calculation between the data points in the look-up table or mathematical formula, making a final determination of an analyte concentration level output value. The foregoing process may then be repeated by the patient in order to calculate additional d1, d2 and d3 offsets and thus produce another adjusted compensated voltage-analyte concentration curve 39000', illustrated with a dashed line, for each batch of patches or strips.

Reference is now made to FIG. 63 wherein there is shown a flow diagram illustrating a process for converting an input voltage indicative of read color shade into a concentration value output. The illustrated process not only accounts for any temperature considerations in generating the compensated voltage, but also accounts for any interpolations required by the second order calibration offsets, see FIG. 61, and the calculation between the data points in the look-up table, see FIG. 57. In step 60000, a stable output voltage indicative of color and shade has been determined, see FIG. 59. If any DC offsets affecting the accuracy of stable output voltage are present, such as that provided with respect to the synchronous detector, these offset(s) are subtracted from the stable output voltage in step 60200. Next, in step 60400, the offset adjusted stable output voltage is processed using the equation discussed above to compensate for variations in light source intensity due to temperature and produce a compensated voltage (CV). The compensated voltage is then processed in step 60600 to make any needed adjustments relating to second order color calibration and third order batch code calibration, see FIGS. 61 and 62. A lookup table (or mathematical formula) is then used to convert the color (batch code) calibration adjusted compensated voltage in step 60800 to a concentration level. Any necessary interpolations to the determined concentration level are then made in step 61000. A determination is then made in step 61200 as to whether the (interpolated) determined concentration level is within an acceptable anticipated range for the particular test being made. If not, an error message is displayed in step 61400, and record of the error is stored in step 61600 along with a date and time of day. If so, the (interpolated) determined concentration level is displayed in step 61800, and record of the level is stored in step 61600 along with a date and time of day.

Examples of varies embodiments of the present invention will now be further illustrated with reference to the following examples.

Unless otherwise stated in a specific example, the targeted skin area and the dry chemistry membranes in the following Examples are treated and prepared, respectively, as follows.

To make a dry glucose chemistry membrane, a 100 ml base preparation is first prepared. This base preparation contains:
about 60 gm Polyvinyl pyrrolidinone K-30 (mw 40,000)
about 1.2 gm Citric Acid Trisodium Salt
about 0.1 gm Citric Acid Monohydrate
about 0.028 gm $NaBH_4$ (sodium Borohidrate)
about 0.1 gm Bovine Serum Albumin (BSA)

The ingredients for the base solutions are dissolved and thoroughly mixed. Once the base solution is prepared, the following quantities of conditioning, flow and stabilizing agents and indicators are added:
about 0.546 gm O-Tolidine
adjust pH to about 5.9 to about 6.0
about 2.0 ml 10% Ganttrez S-95 (10.0 gm/100 ml) is added
and pH is adjusted to about 5.9 to about 6.0 with NaOH.
about 4.0 gm/L 75% DOSS [0.533 gm].

The conditioning flow agents, stabilizing agent (BSA) and the indicator (O-Tolidine) is dissolved and mixed well into the base preparation. Once the agents and indicator are blended intimately into the base preparation, the specific enzymes for reaction with glucose are added:

about 121.0 mg Glucose Oxidase (60D) 150 u/ml [150 u*100 ml/124 u/mg]

about 38.53 mg Horse Radish Peroxidase (POD) 100 u/ml [100 u*1.00 ml/259.55 u/mg].

The enzymes are added and stirred throughly.

To prepare a membrane, a Biodyne A membrane (0.45 micron pore size) is dipped briefly for about 30 seconds into the prepared enzymatic cocktail until uniformly wetted. It is then air dried at about 37° C. for about 15 minutes. The dried membrane is stored with desiccant protected from moisture and light. The dried glucose chemistry membrane can be cut into strips of a size about 0.75 inches with an exposed testing area of about 3/16 inches, and the cut strips can be encapsulated or glued within the fold of an adhesive coated mylar, such as Dermaflex PM 500 within a patch configuration, such as illustrated in FIG. 3. It is believed that approximately 5 liters of the enzymatic cocktail will effectively treat 200 sq. ft. of the Biodyne A membrane.

Before conducting the experiments, the targeted skin area and the hands of the user are treated as follows unless specified otherwise.

First, user cleans his/her hands and the targeted skin area thoroughly with deionized water (18 meg ohm). The targeted skin area and hands may be rinsed with the deionized water or wiped with a non-bleached paper towel that has been wetted with the deionized water. The cleansed skin area and hands are then dried with a non-bleached paper towel. Users should avoid the use of bleached paper towels and chlorinated water.

If the targeted skin area is to be pretreated with a skin permeation enhancer, the cleansed and dry targeted skin area is then wiped one or more times with a KimWipe® which is wetted with about 0.5 ml of a selected permeation enhancer. A suitable size KimWipe® for application of the 0.5 ml skin permeation enhancer is dimensioned at 5×5 cm. While Kim-Wipes® are used, any other ultra clean, lint-free, non-bleached paper towels may be used. KimWipes® are supplied by Kimberly Clarke.

Once the precleansed targeted skin area is treated with a skin permeation enhancer, the pretreated skin is inspected to ensure that there is not excessive skin permeation enhancers on the skin. If too much has been applied, the patch adhesive may not stick. Thus, any excess skin permeation enhancer should first be removed with, for example, a KimWipe®, before applying the patch.

If an organic solvent type skin permeation enhancer is selected, such as isopropyl alcohol or ethyl acetate, it is preferable to allow the organic solvent to first dry or evaporate before applying the patch to the treated skin area to avoid potential negative interaction between the organic solvent type skin permeation enhancer and the chemical reagents on the membrane. If the skin permeation enhancer selected is not an organic solvent, the patch may be applied immediately following treatment of the skin area with such skin permeation enhancer.

Before the patch is applied, it is removed from its foil envelopes with 1 gram of desiccant. Following removal, the selected transfer medium or gel is loaded into the hole in the bottom of the patch to uniformly and continuously wet the membrane. Once the membrane is wetted with the gel, the test should be conducted within 5 to 10 minutes thereafter. Also, wetted membrane should not be exposed to bright lights.

Once the patch is positioned on the targeted skin area, it is left therefor about 5 minutes, at which time the color change is read by a reflectometer to detect the present of glucose.

Also, unless otherwise specified, the wet chemistry gel utilized is about 1% carboxy methylcellulose in deionozed water (18 meg ohm).

Example 1

The following two figures represent data obtained with a glucose patch in accordance with the present invention. The glucose membrane is prepared similar to that described immediately above.

Figure 11:
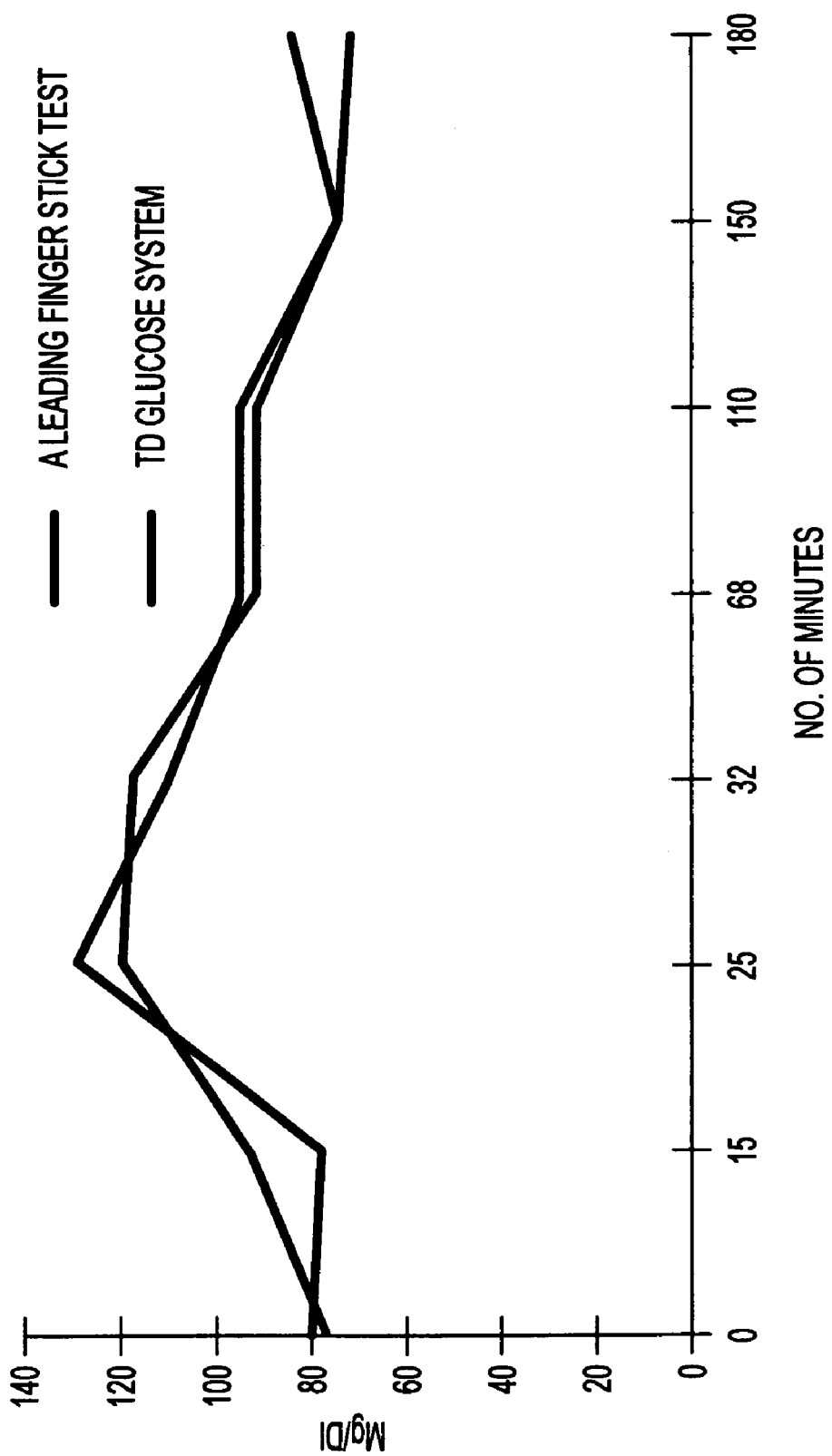
FIG. 11 is a plot of data of an oral glucose tolerance test comparing the results obtained from a noninvasive transdermal patch of the present invention with the results obtained from capillary blood glucose using the APG method.

FIG. 11 shows results of a glucose tolerance test performed on a non-diabetic subject over a three hour period. These results in FIG. 11 show a high correlation between the glucose patch and a current popular finger stick method. In this example, the wipe is propylene glycol.

Example 2

Figure 12:
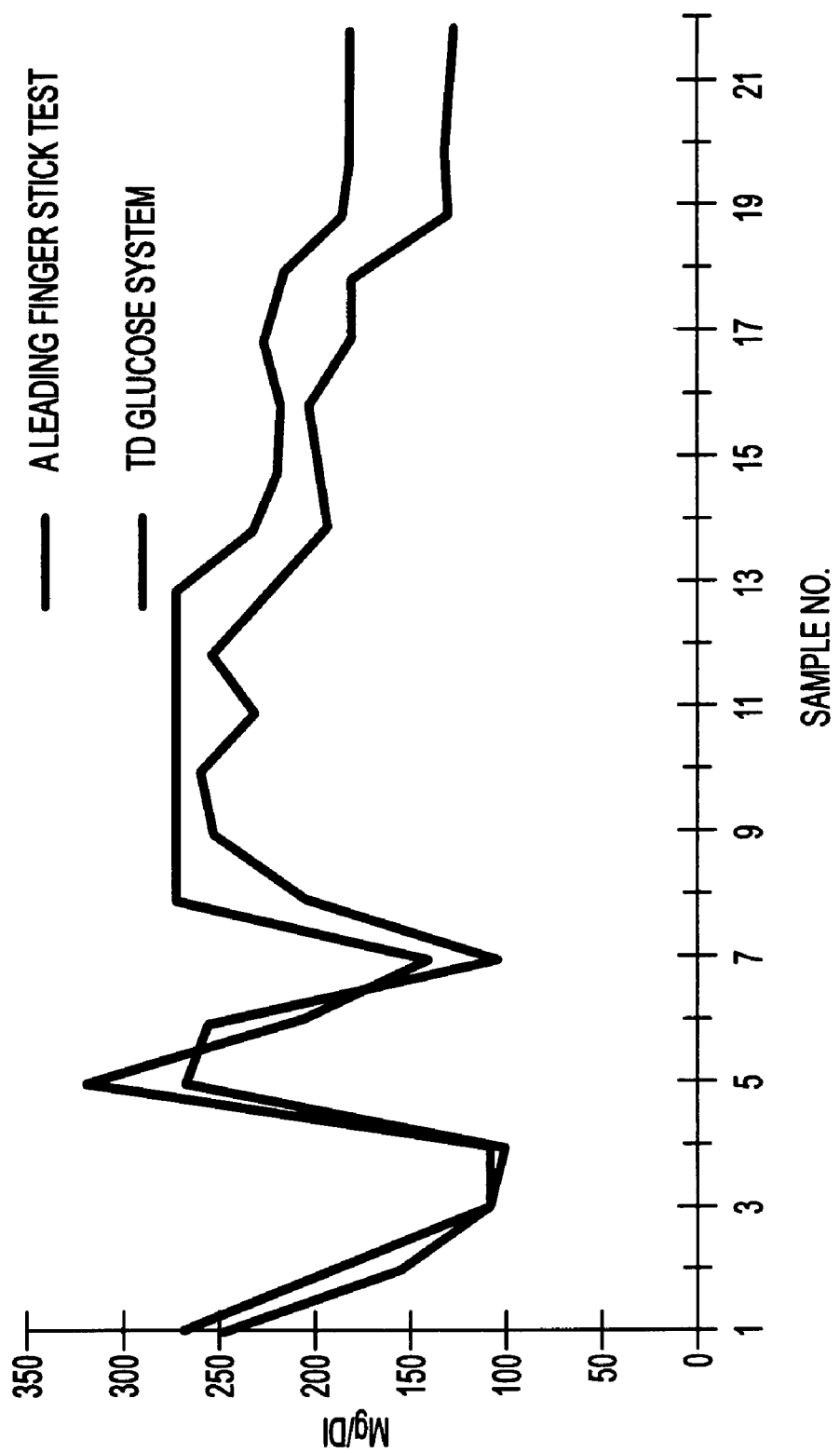
FIG. 12 is a plot of data of an oral glucose tolerance test comparing the results obtained from a noninvasive transdermal patch of the present invention with the results obtained from capillary blood glucose using the APG method.

FIG. 12 shows the results of a series of tests that are performed on a Type I insulin dependent diabetic over a 21 day period. One sample is taken per day in a random manner—with no control over the sampling time of day or relation to the patient's insulin.

Example 3

Figure 13:
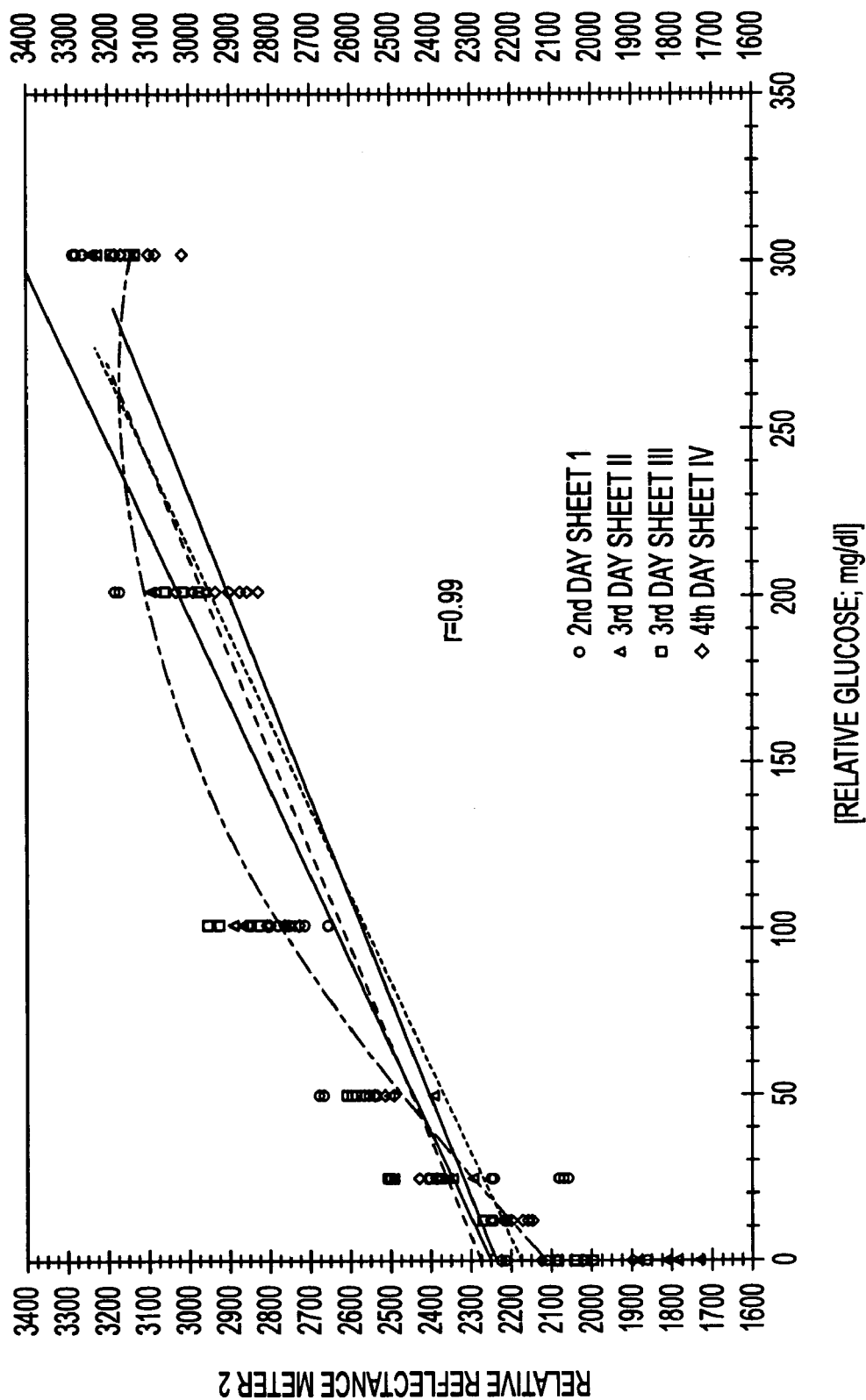
FIG. 13 is a plot of data of the results of testing linearity of glucose patch reaction chemistry in glucose patches of the present invention when increasing concentrations of glucose.

FIG. 13 depicts data from a series of experiments testing the linearity of the glucose patch reaction chemistry to increasing concentrations of glucose. Four glucose determinations are performed daily on a series of standards and the results correlated after four days of tests. These results show that the detection membrane is capable of measuring the minute amounts of glucose.

Figure 14:
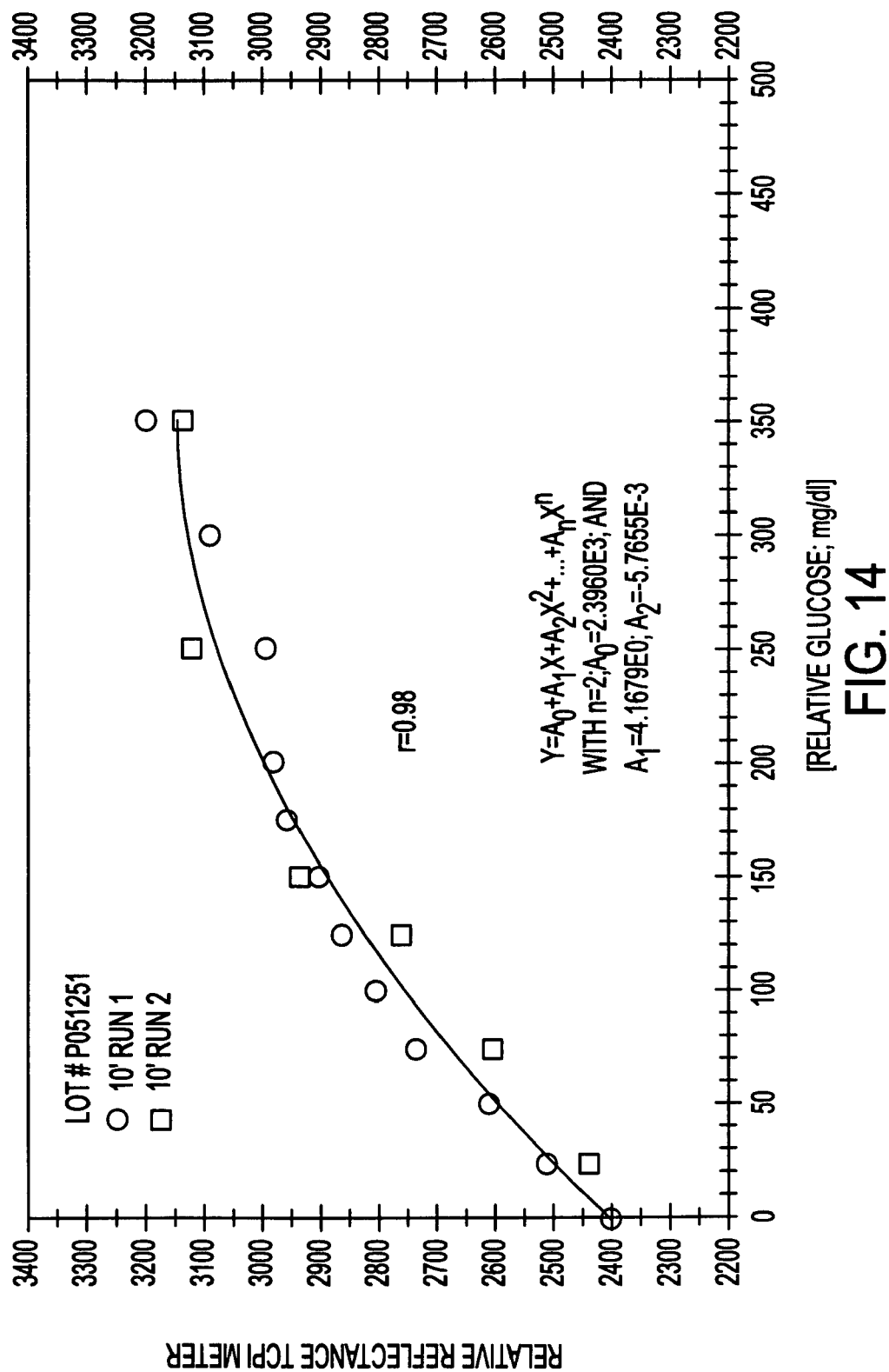
FIG. 14 is a graph of data depicting an actual calibration curve for a noninvasive transdermal glucose patch of the present invention.
Figure 16A:
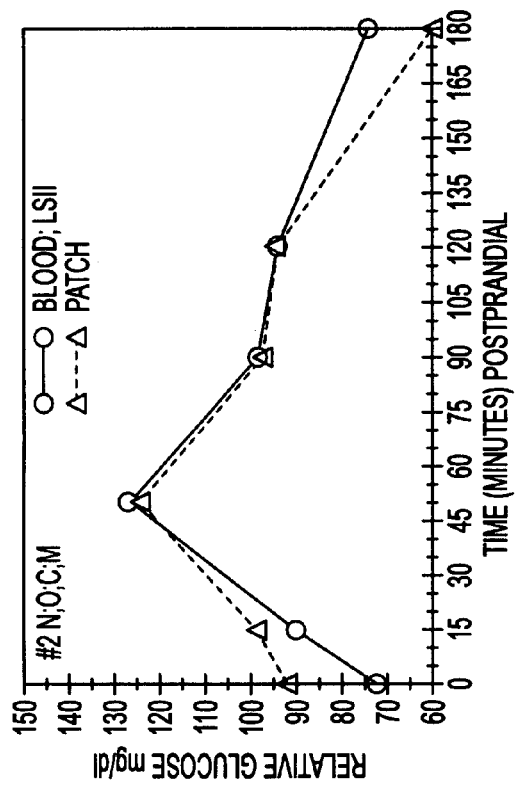
FIG. 16 illustrates plots of data which compares the results obtained from a noninvasive transdermal patch of the present invention with results obtained from capillary blood glucose utilizing standard LSII methods.
Figure 16B:
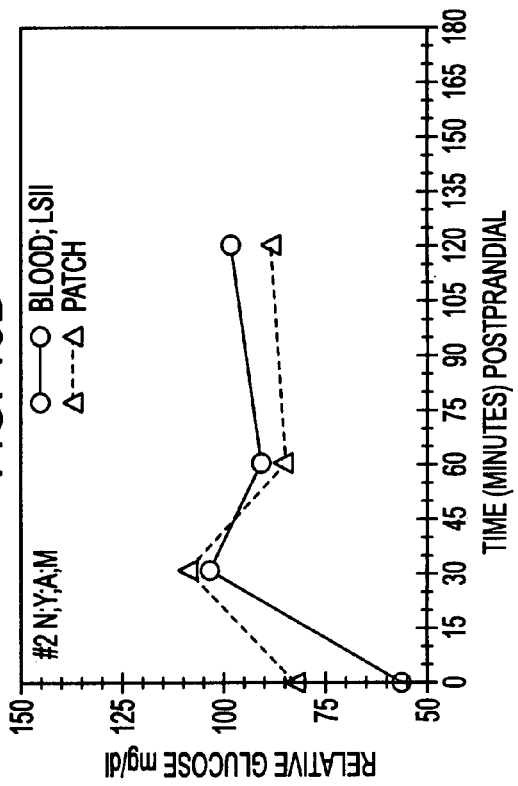
Figure 16C:
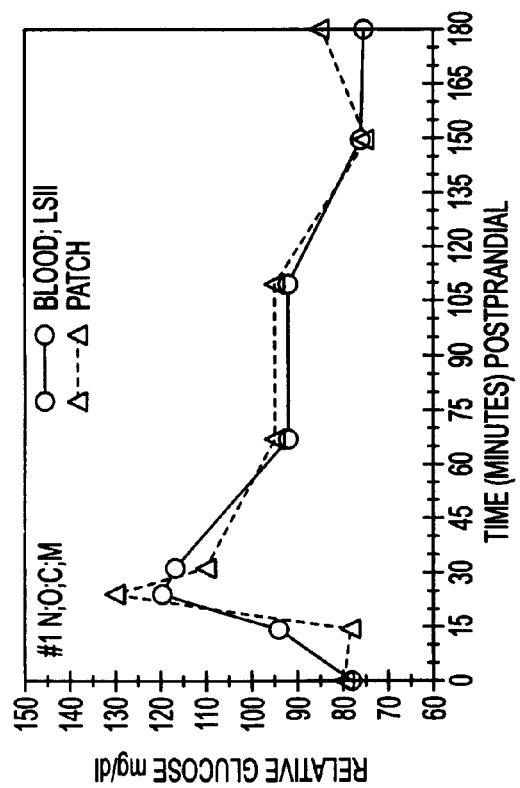
Figure 16D:
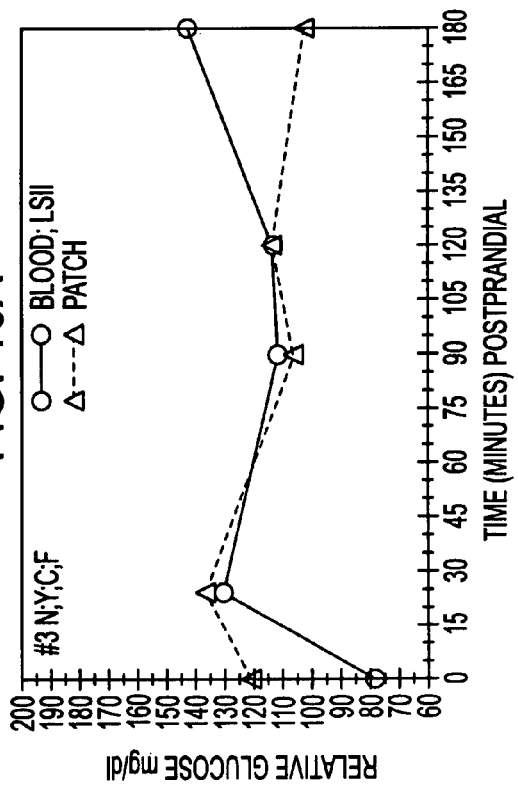
Figure 17A:
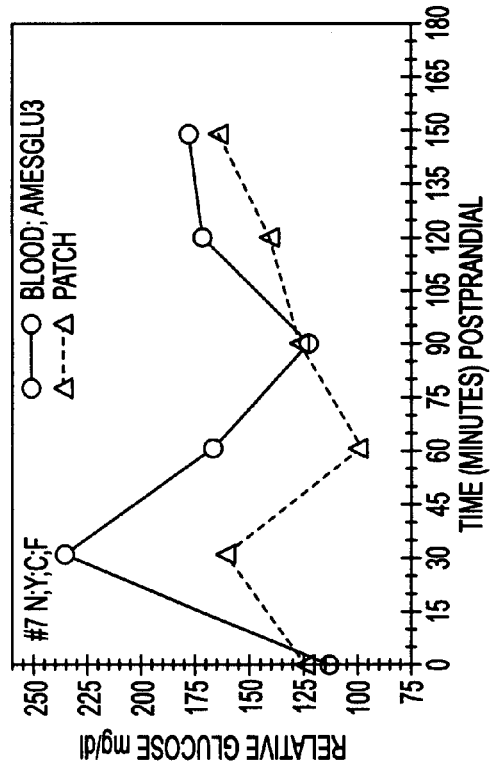
FIG. 17 illustrates plots of data which compares the results obtained from a noninvasive transdermal patch of the present invention with results obtained from capillary blood glucose utilizing standard LSII methods.
Figure 17B:
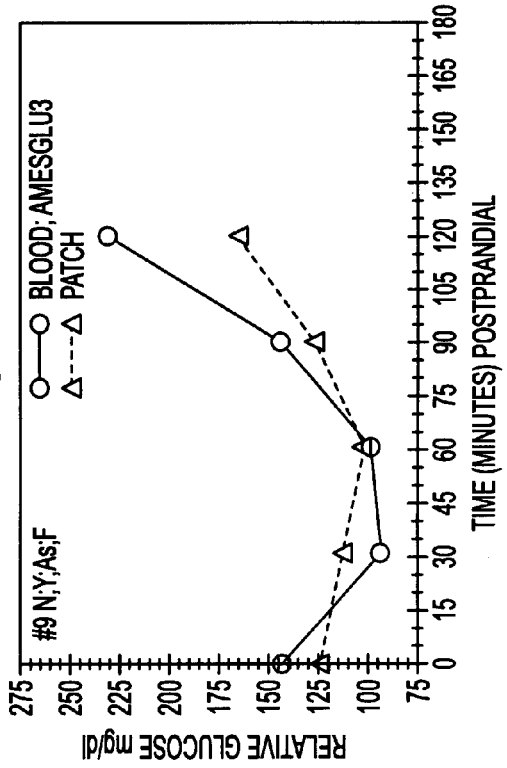
Figure 17C:
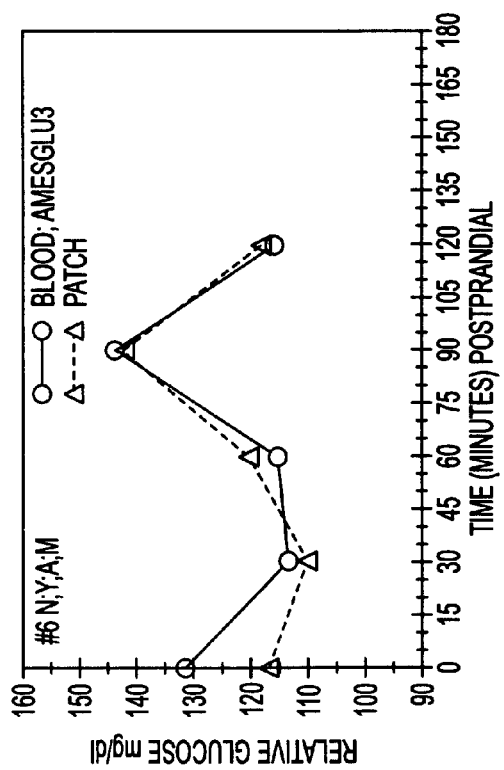
Figure 17D:
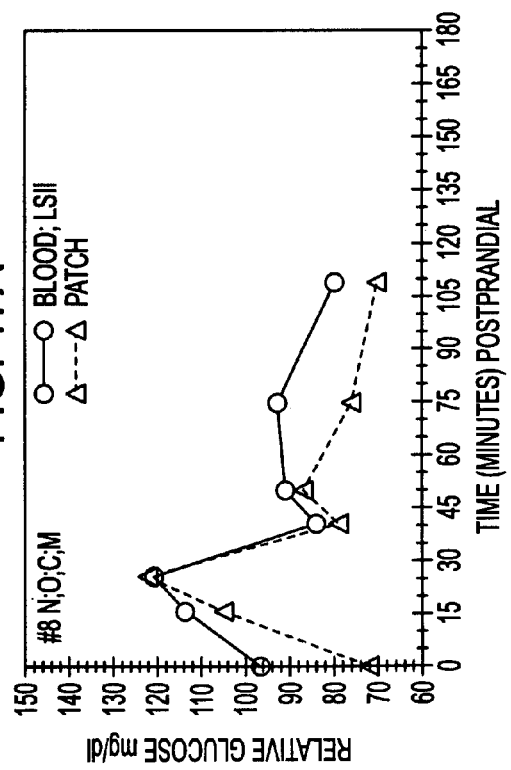

FIG. 14 depicts an actual calibration curve for the glucose patch. The data is depicted in FIG. 15A. A set of these glucose patches are evaluated with calibration standards using nine patches for each standard. The coefficient of variation averaged less than 4% with an r-value of 0.99 for the standard curve after 5 minutes of reaction time.

Example 4

The following is data resulting from oral glucose tolerance tests of volunteers. The tests are designed to compare the results obtained with the glucose patch to a "state of the art" capillary blood glucose method from other companies. The patch reflectance data is obtained using a reflectometer as described herein. These people have not eaten for twelve hours prior to the tests. After initial glucose determinations, they drank a solution of 100 grams of glucose within five minutes. The comparative tests are continued over the course of 1.5-3 hours. Note that the capillary blood glucose values rise to a peak level by 30-50 minutes and then return to "normal", as is expected with nondiabetics. The patch reflectance values parallel the capillary blood glucose values and are much easier to obtain.

All blood results are obtained using an FDA "accepted" standard finger stick capillary blood glucose method with the manufacturers electronic meter indicated for each test and strips by the recommended procedure.

Patient 1 is a normal person (older Caucasian male) who is tested at fasting level through postprandial 100 grams glucose for three hours:

| Time (min.) Postprandial | Blood Glucose Life Scan II mg/dl | Patch Glucose mg/dl |
| --- | --- | --- |
| 0 | 78 | 80 |
| 15 | 94 | 78 |
| 25 | 120 | 130 |
| 32 | 117 | 110 |
| 68 | 92 | 95 |
| 110 | 92 | 95 |
| 150 | 76 | 75 |
| 180 | 73 | 85 |

Patient 2 is a normal (older Caucasian male) person who is tested at fasting level through postprandial 100 grams glucose for three hours:

| Time (min.) Postprandial | Blood Glucose Life Scan II mg/dl | Patch Glucose mg/dl |
| --- | --- | --- |
| 0 | 73 | 92 |
| 15 | 91 | 99 |
| 50 | 128 | 125 |
| 90 | 99 | 98 |
| 120 | 95 | 95 |
| 180 | 75 | 60 |

Patient 3 is a normal person (young Caucasian female) who is tested after breakfast through lunch, moderate exercise, and a snack, for three hours:

| Time (min.) Postprandial | Blood Glucose Life Scan II mg/dl | Patch Glucose mg/dl |
| --- | --- | --- |
| 0 | 77 | 120 |
| 24 | 130 | 136 |
| 90 | 111 | 106 |
| 120 | 113 | 113 |
| 180 | 143 | 102 |

Patient 4 is a normal person (young African American male) who is tested fasted for two hours:

| Time (min.) Postprandial | Blood Glucose Life Scan II mg/dl | Patch Glucose mg/dl |
| --- | --- | --- |
| 0 | 55 | 81 |
| 30 | 103 | 108 |
| 60 | 90 | 85 |
| 120 | 98 | 88 |

Patient 5 is a type I diabetic patient (older Caucasian male) who is tested on twenty two occasions by several different extraction formulations:

| Time (min.) Postprandial | Blood Glucose Life Scan II mg/dl | Patch Glucose mg/dl |
| --- | --- | --- |
| 1 | 268 | 247 |
| 2 | 196 | 157 |
| 3 | 109 | 110 |
| 4 | 108 | 101 |
| 5 | 314 | 265 |
| 6 | 207 | 251 |
| 7 | 140 | 106 |
| 8 | 267 | 203 |
| 9 | 367 | 248 |
| 10 | 267 | 256 |
| 11 | 267 | 228 |
| 12 | 267 | 251 |
| 13 | 267 | 218 |
| 14 | 227 | 190 |
| 15 | 216 | 196 |
| 16 | 213 | 200 |
| 17 | 222 | 180 |
| 18 | 214 | 181 |
| 19 | 183 | 127 |
| 20 | 179 | 130 |
| 21 | 180 | 127 |
| 22 | 178 | 125 |

Patient 6 is a normal person (young African American male) who is tested over the course of two hours:

| Time (min.) Postprandial | Blood Glucose Life Scan II mg/dl | Patch Glucose mg/dl |
| --- | --- | --- |
| 0 | 132 | 116 |
| 30 | 113 | 110 |
| 60 | 115 | 120 |
| 90 | 144 | 142 |
| 120 | 116 | 118 |

Patient 7 is a normal person (young Caucasian female) who is tested after breakfast through lunch, moderate exercise, and a snack, for two and ½ hours:

| Time (min.) Postprandial | Blood Glucose Life Scan II mg/dl | Patch Glucose mg/dl |
| --- | --- | --- |
| 0 | 111 | 120 |
| 30 | 237 | 160 |
| 60 | 167 | 98 |
| 90 | 121 | 125 |
| 120 | 173 | 140 |
| 150 | 180 | 165 |

Patient 8 is a normal person (older Caucasian male) who is tested after fasting level through postprandial 100 grams glucose for two hours:

| Time (min.) Postprandial | Blood Glucose Life Scan II mg/dl | Patch Glucose mg/dl |
| --- | --- | --- |
| 0 | 95 | 70 |
| 15 | 113 | 104 |
| 25 | 120 | 122 |
| 40 | 83 | 78 |
| 50 | 90 | 86 |
| 75 | 92 | 75 |
| 110 | 79 | 69 |

Patient 9 is a normal person (young Asian female) who is tested after breakfast through lunch, and a snack, for two hours:

| Time (min.) Postprandial | Blood Glucose Life Scan II mg/dl | Patch Glucose mg/dl |
|---|---|---|
| 0 | 141 | 120 |
| 30 | 91 | 110 |
| 60 | 97 | 100 |
| 90 | 144 | 126 |
| 120 | 233 | 165 |

Patient 10 is a normal person (young Caucasian male) who is tested after breakfast then glucose load for two hours:

| Time (min.) Postprandial | Blood Glucose Life Scan II mg/dl | Patch Glucose mg/dl |
|---|---|---|
| 0 | 89 | 105 |
| 30 | 125 | 123 |
| 60 | 97 | 105 |
| 120 | 105 | 120 |

Figure 18A:
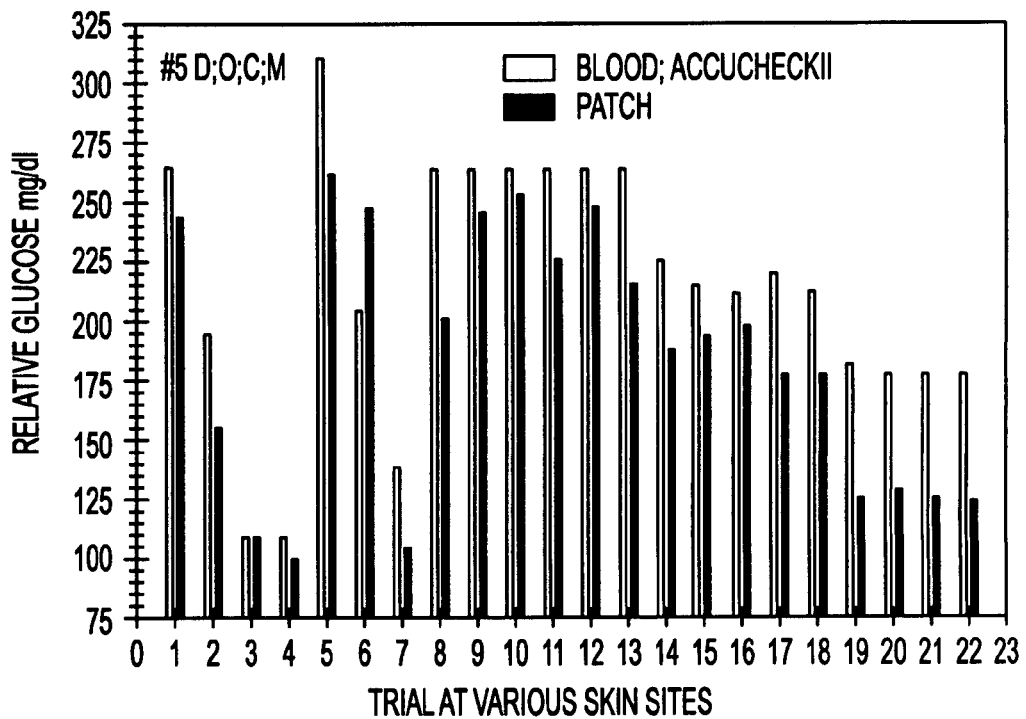
FIG. 18 illustrates plots of data which compares the results of a noninvasive transdermal patch of the present invention with the results obtained from capillary blood glucose utilizing standard LSII methods.
Figure 18B:
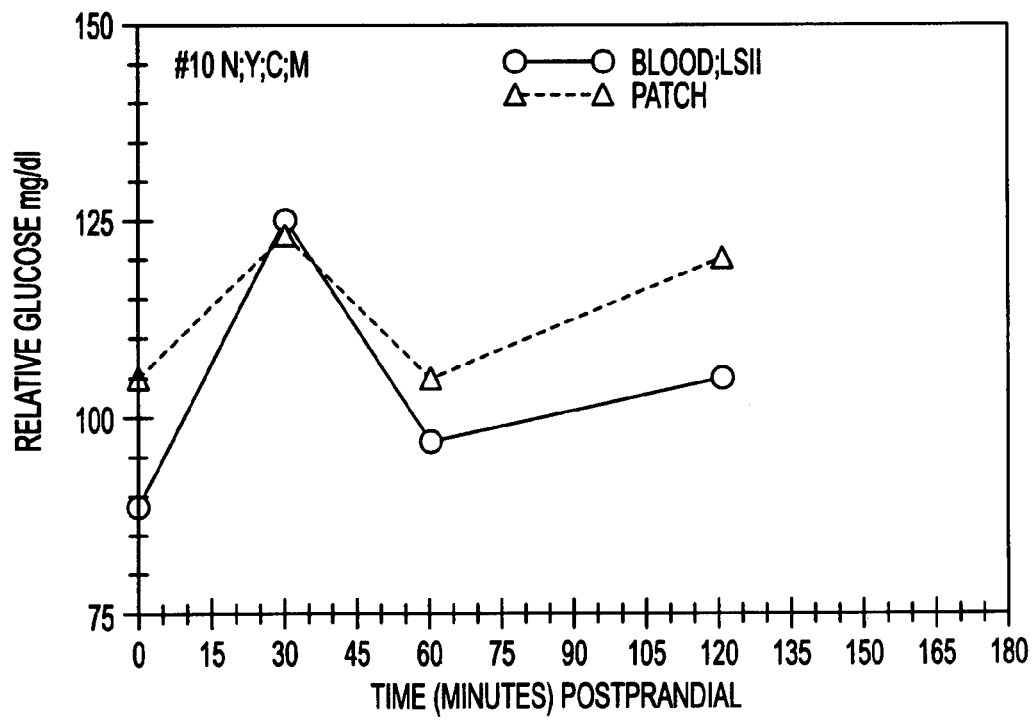

PATIENT KEYS
N = Normal
D = DIABETIC TYPE I;
O = OLDER
= MIDDLE AGE (NONE TESTED)
Y = YOUNGER
C = CAUCASIAN
A = AFRICAN AMERICAN
AS = ASIAN
M = MALE
F = FEMALE The results of the comparison of a standard finger stick method with glucose patch subjects undergoing glucose tolerance tests are depicted in FIGS. 16, 17 and 18. One type I diabetic subject (#5) is included. For comparison, two different "NO WIPE" finger stick method are also used. Subject #9 (see FIG. 11) engages in some extensive manual labor between testing, and as depicted, despite the glucose load she receives, her glucose level decreases. She also begins the glucose tolerance test late and eats lunch before the end of the test period.

Subject 5 (See FIG. 18, top graph) is a diabetic subject who subsequently performs 22 assays at various skin sites. Instead of receiving a glucose load as with the other 9 patients, this diabetic delays insulin administration then tests both before and after insulin for two separate, four test periods. Comparison #8-22 in FIG. 18, top graph, reflect one series of tests a day consisting of 6 simultaneous patches using different skin sites, which are performed before administering insulin, and which are followed by 5 simultaneous patches on the same sites which are performed later in the day after eating, but before diabetic's injection and finally 4 simultaneous patches at different sites after giving sufficient time for the insulin to lower the diabetic's glucose levels.

Example 5

Figure 19:
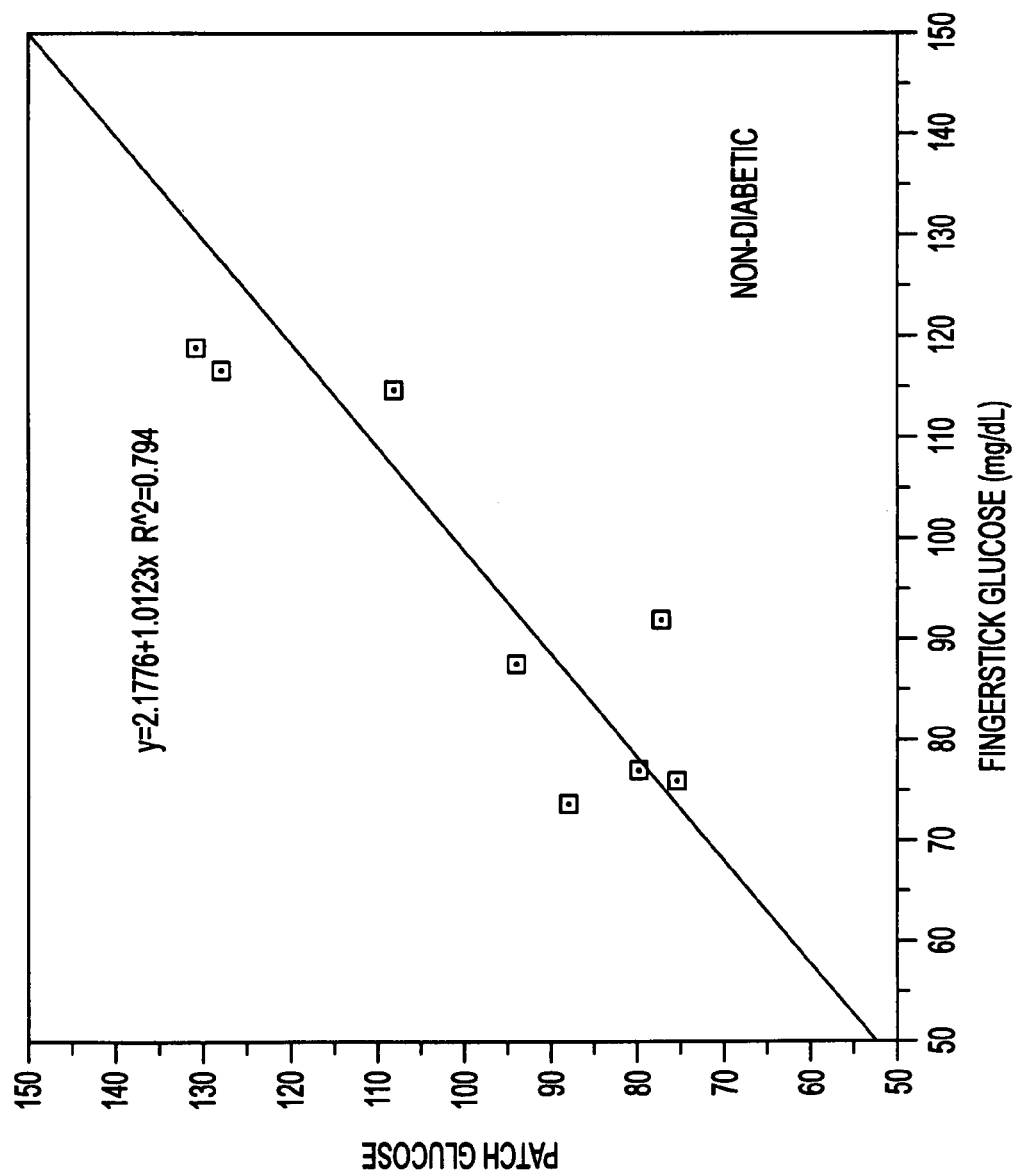
FIG. 19 is a plot of data which shows the correlation of results between a noninvasive transdermal patch of the present invention with results obtained from capillary blood glucose utilizing a standard method.

FIG. 19 illustrates the results of the comparison of blood glucose levels in eight (8) non-diabetics using patches vs. finger stick. It confirms that the correlation between finger stick tests and plasma glucose in the range of from $r^2=0.53$-$0.93$ comparing different finger stick tests using both name brand and generic strips.

Example 6

Figure 20:
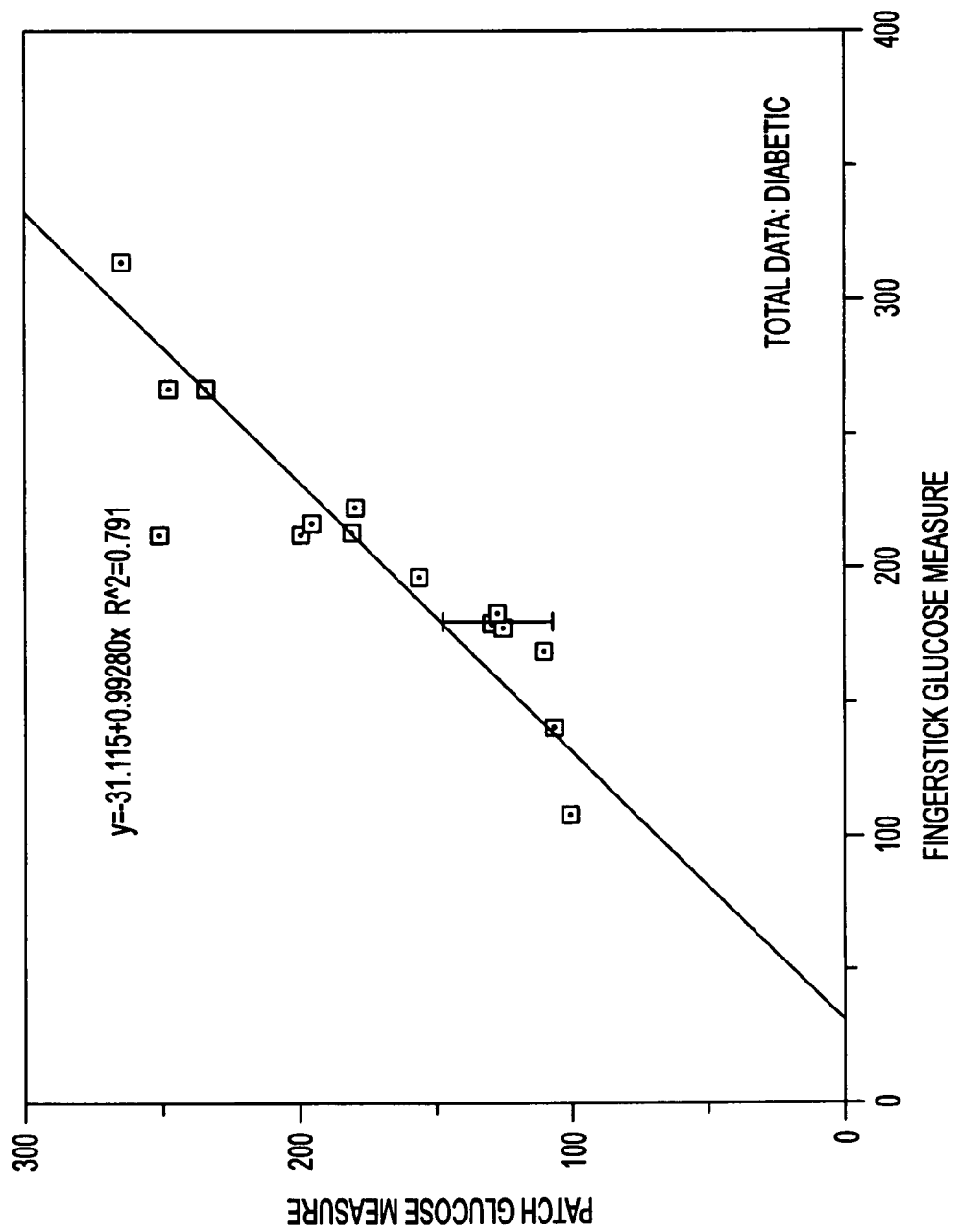
FIG. 20 is a plot of data which shows the correlation of results obtained from a noninvasive transdermal patch of the present invention with results obtained from capillary blood glucose utilizing a standard method.
Figure 21:
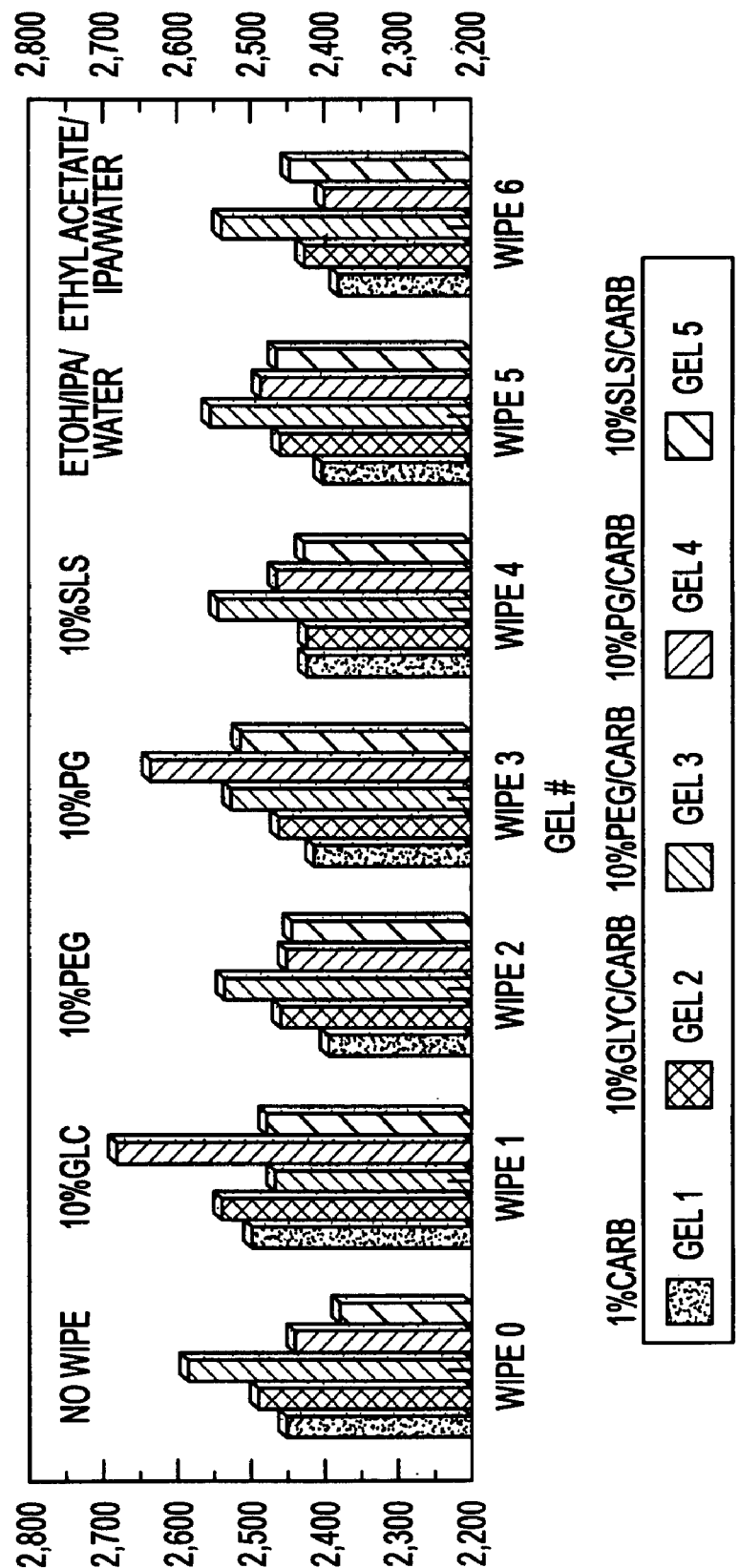
FIG. 21 is a bar graph of data which shows the results obtained from noninvasive transdermal patches of the present invention constructed with different gels which are tested with different wipes.
Figure 22:
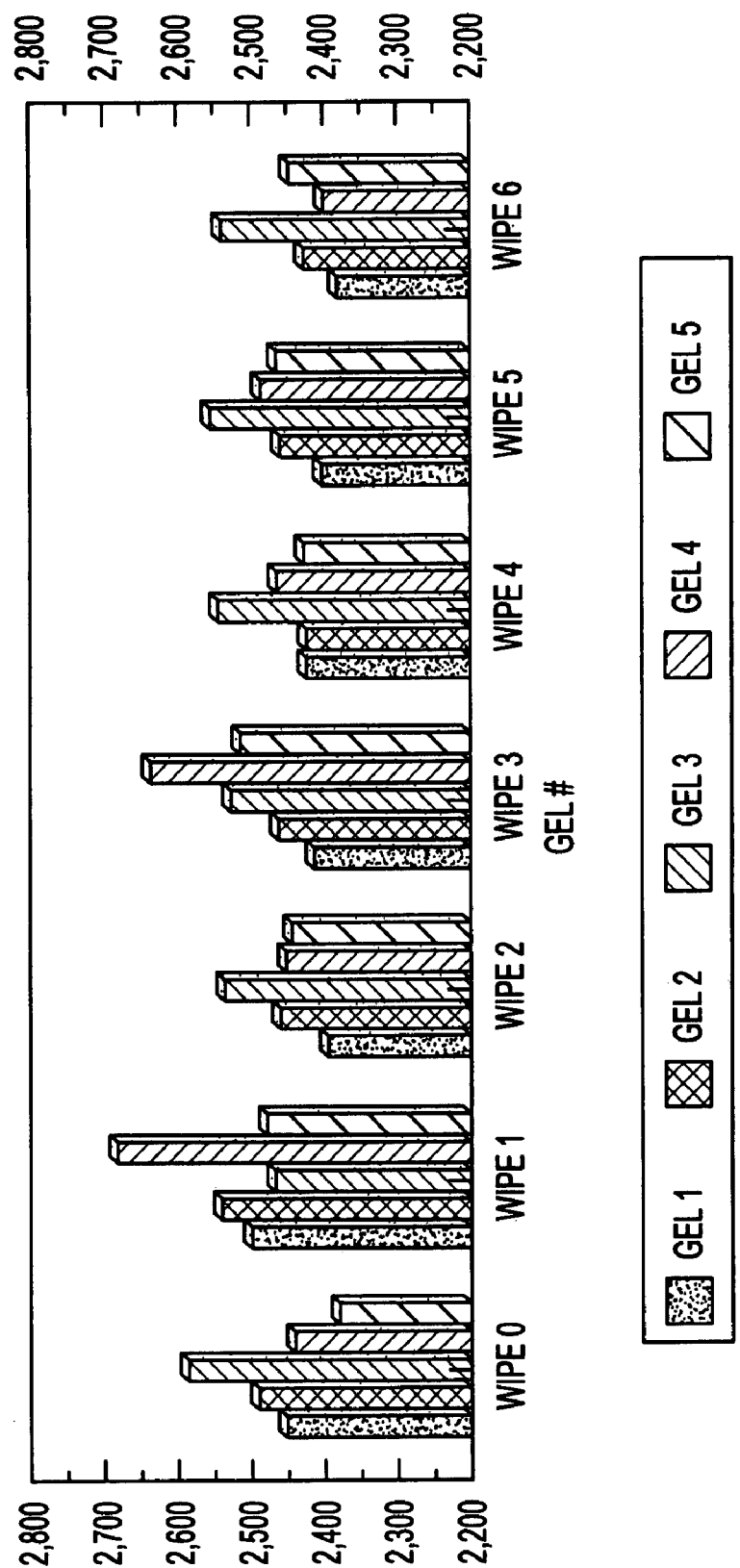
FIG. 22 is a bar graph of data which shows the results obtained from noninvasive transdermal patches of the present invention constructed with different gels which are tested with different wipes.
Figure 23:
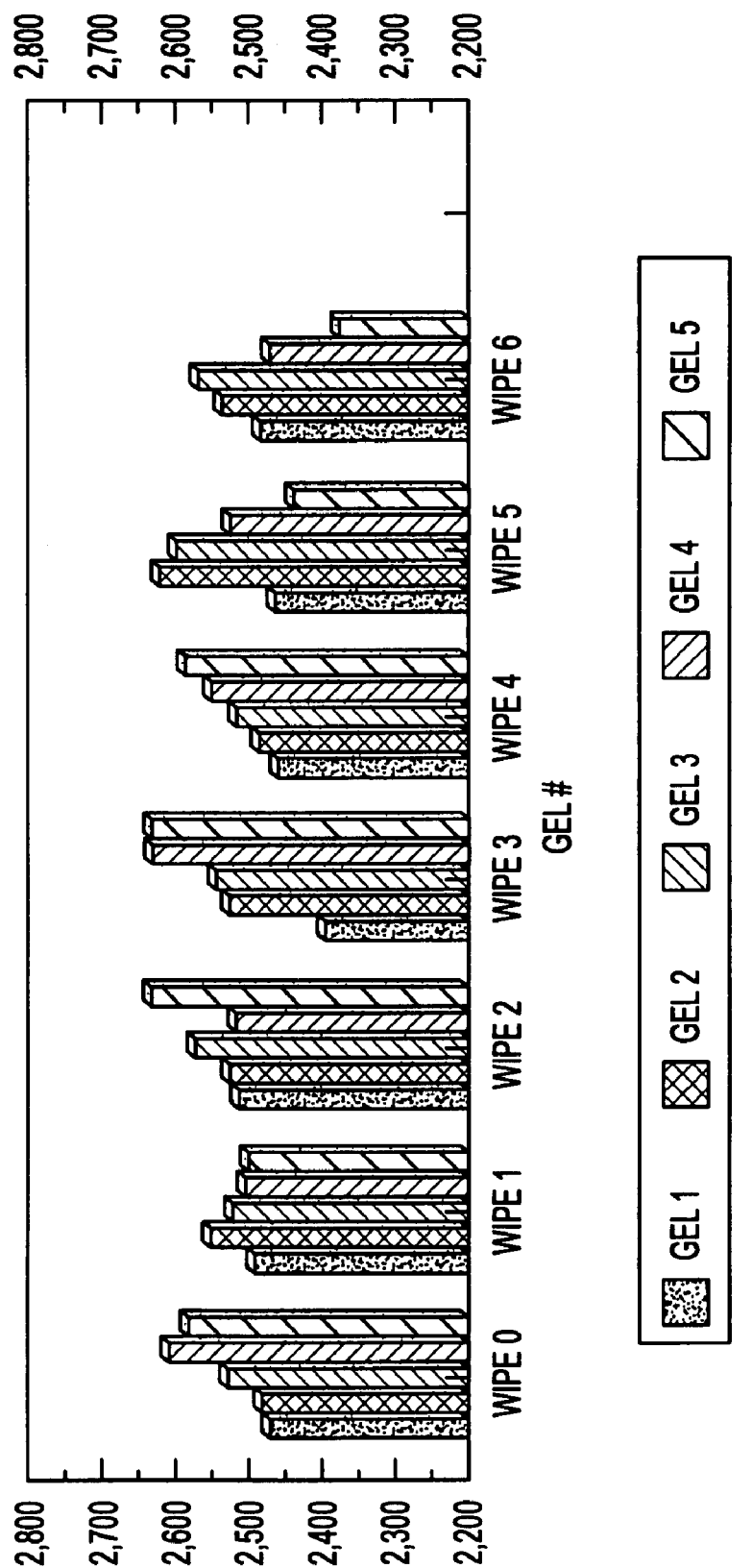
FIG. 23 is a bar graph of data which shows the results obtained from noninvasive transdermal patches of the present invention constructed with different gels which are tested with different wipes.
Figure 24:
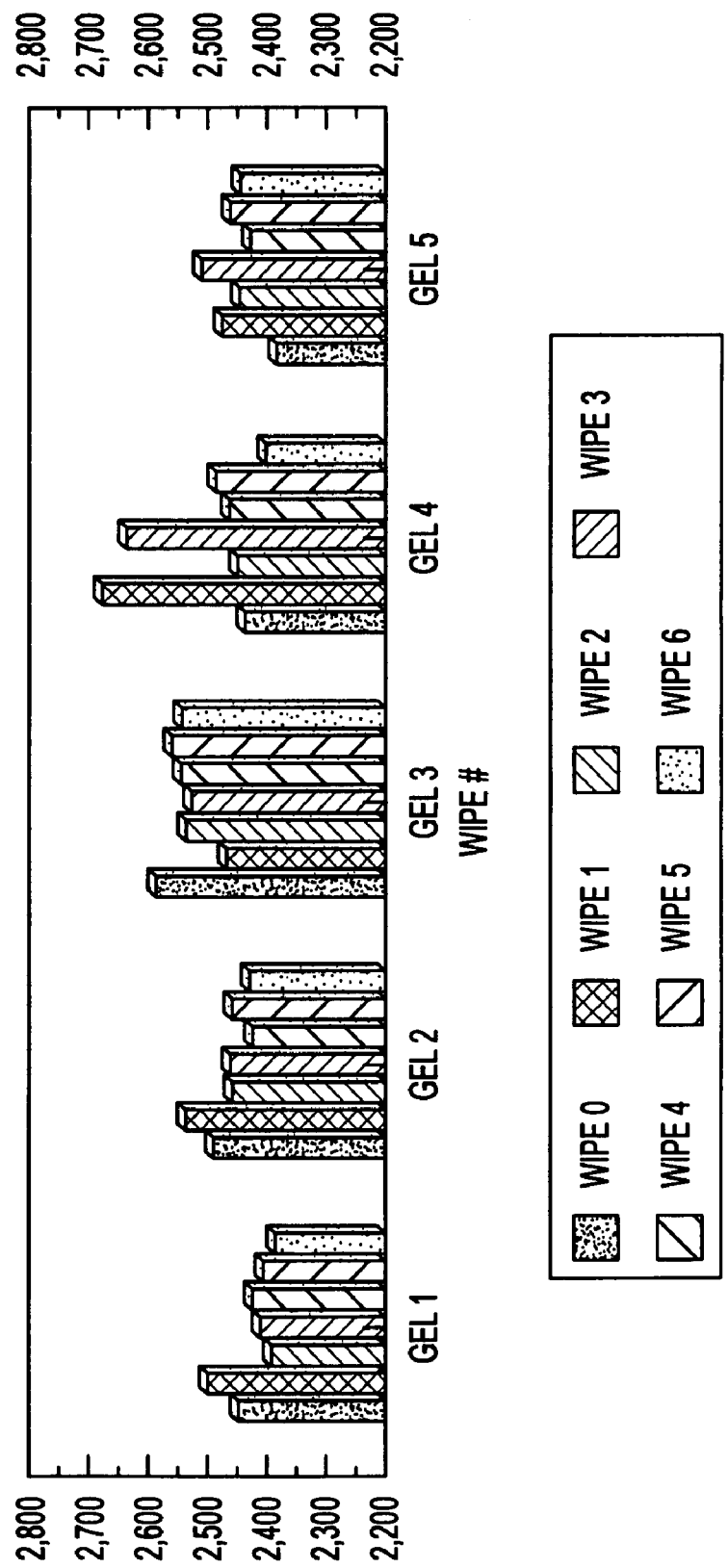
FIG. 24 is a bar graph of data which shows the results obtained from noninvasive transdermal patches of the present invention constructed with different gels which are tested with different wipes.
Figure 25:
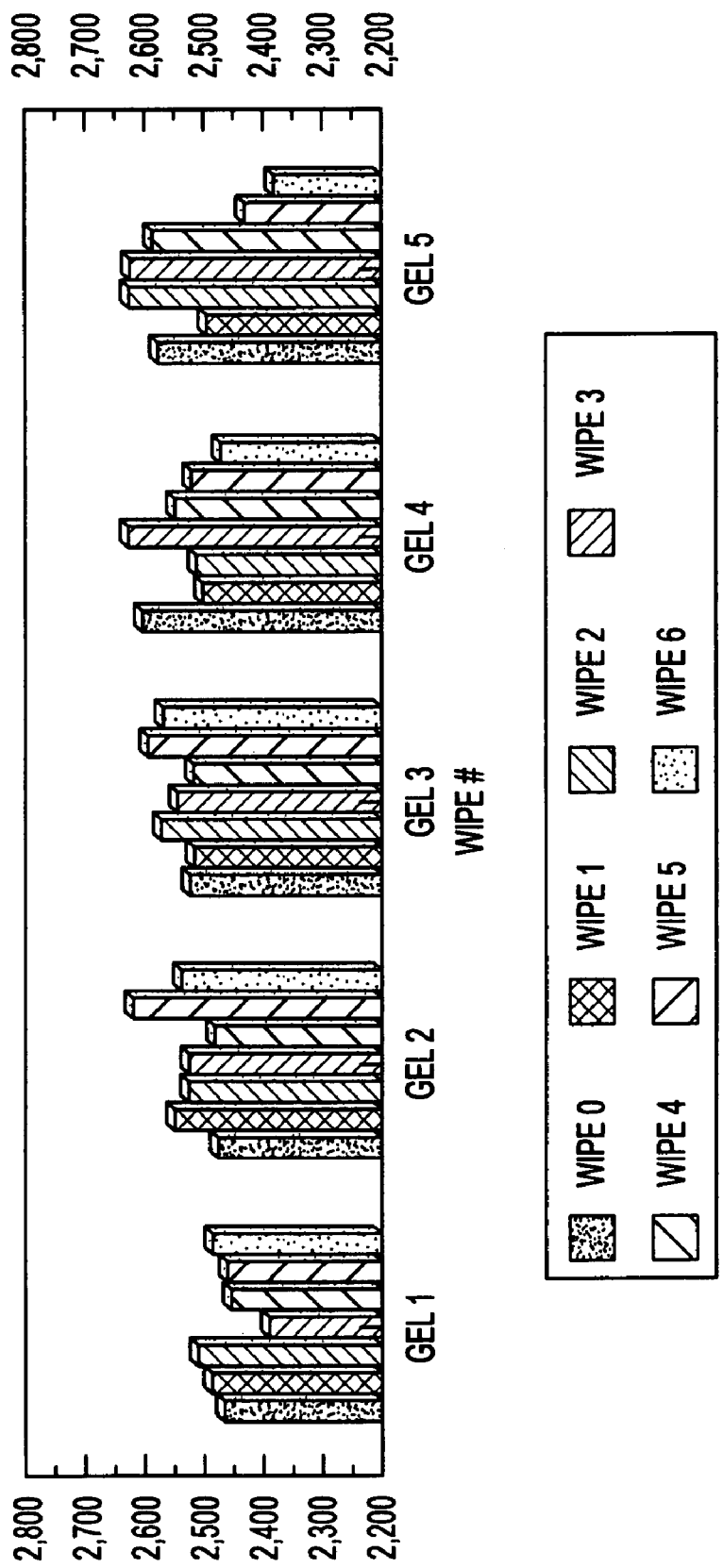
FIG. 25 is a bar graph of data which shows the results obtained from noninvasive transdermal patches of the present invention constructed with different gels which are tested with different wipes.

A similar series of experiments are performed with a diabetic subject. See FIG. 20. FIG. 20 shows that the patch and finger stick blood glucose levels correlate in a highly significant fashion with a coefficient of determination $r^2=0.791$ and significant level of $p=0.001$. These results are obtained on one subject over several months. This data demonstrates good correlation over a glucose range of 100-300 mg/dl. There are no changes in diabetic therapy or insulin dosages throughout the testing period. One portion of the diabetic data defines the variance as a single subject with three patches on each arm.

Example 7

Two individuals, MM and JM, volunteered to test 5 different gels and 6 different wipes in combination with a super sensitive or conditioned glucose membrane in accordance with the present invention.

Prototype glucose membranes are made as described earlier herein with respect to the alternative glucose reactive membrane.

The glucose patch, into which the glucose membrane was placed, is similar to the patch depicted in FIG. 3.

Gels

The five gels are as follows:

1. About 1% carbopol in deionized water;

2. About 10% glycerin and about 1% carbopol in deionized water;

3. About 10% polyethylene glycol and about 1% carbopol in deionized water;

4. About 10% propylene glycol and about 1% carbopol in deionized water

5. About 10% sodium lauryl sulfate and about 1% carbopol.

The gels are made by simply mixing the components together thoroughly as described herein.

Wipes

The six wipes are as follows:

1. About 10% glycerin in deionized water;

2. About 10% polyethylene glycol in deionized water (18 meg ohm);

3. About 10% propylene glycol in deionized water (18 meg ohm);

4. About 10% sodium lauryl sulfate in deionized water (18 meg ohm);

5. 1:1:1 ethyl alcohol:isopropyl alcohol: deionized water 6. 1:1:1 ethyl acetate:isopropyl alcohol:deionized water (18 meg ohm).

The wipes are made as follows: mixed and thoroughly stirred and stored in an amber bottle with a teflon lined cap to minimize contamination and evaporation.

Each individual's blood glucose is determined by LSII method at the time of testing. MM's blood glucose measured as 96 mg/dl, and JM's blood glucose is 100 mg/dl. In detailing the reflectance from the glucose patches, a reflectometer having the specification described herein is used.

In carrying out the procedure, each individual's targeted skin area, to which the patch is applied, is first thoroughly cleansed by wiping with deionized water. Following cleansing, in one test, the five different gels glucose patches are applied directly to the cleansed skin area without first wiping with a wipe. In all other tests, the cleansed skin area is first pretreated with one of the six wipes. In pre-treating the skin area, a liberal amount of a wipe is applied by a ChemWipe™. If too much is applied, the excess amount is removed with a dry ChemWipe™.

The five different gel glucose patches are then applied to the wiped skin area within ten seconds after wiping. Before applying the gel to the cleansed skin area, the dry chemical glucose membrane is brought into continuous contact with the gel to uniformly wet the dry chemical glucose membrane. The patch is in contact with the cleansed skin area for about 5 minutes, at which time the color change of the membrane is read by reflectance by the meter to detect the glucose in the interstitial fluid of MM and JM. The reflectance values for MM and JM with respect to each gel and wipe are recited in the bar graphs depicted in FIGS. 21, 22, 23, 24, and 25 on the following tables, respectively. The numbers for the gels and wipes designated herein correspond to the numbers in FIGS. 21, 22, 23, 24 and 25.

| WIPE/GEL | 1 | 2 | 3 | 4 | 5 | 6 | 7 |
|---|---|---|---|---|---|---|---|
| 1 | 2504 | 2399 | 2415 | 2428 | 2411 | 2388 | 2456 |
| 2 | 2542 | 2463 | 2465 | 2428 | 2463 | 2433 | 2494 |
| 3 | 2471 | 2542 | 2529 | 2549 | 2561 | 2545 | 2590 |
| 4 | 2684 | 2454 | 2640 | 2467 | 2493 | 2405 | 2443 |
| 5 | 2480 | 2449 | 2516 | 2431 | 2468 | 2452 | 2385 |

| WIPE/GEL | 1 | 2 | 3 | 4 | 5 | 6 | 7 |
|---|---|---|---|---|---|---|---|
| 1 | 2495 | 2519 | 2398 | 2463 | 2468 | 2481 | 2478 |
| 2 | 2557 | 2532 | 2532 | 2488 | 2628 | 2545 | 2486 |
| 3 | 2526 | 2578 | 2551 | 2525 | 2604 | 2578 | 2532 |
| 4 | 2507 | 2520 | 2635 | 2556 | 2528 | 2478 | 2613 |
| 5 | 2502 | 2636 | 2633 | 2593 | 2438 | 2386 | 2585 |

Example 8

The following skin permeation enhancers are tested for permeation enhancing power. The skin is first wiped with a pad wetted with one of the following permeation enhancer formulations. A glass cylinder is then secured by o-ring seal against the wiped area of skin and a defined volume of distilled water is added to the inside of the glass cylinder (see FIG. 26). After five minutes of water contact with the skin, the water is removed and its glucose concentration analyzed by High Performance Liquid Chromatography with a Bioanalytical Systems, Inc. Enzymatic detector system. The ratio of glucose detected relative to the amount detected using a distilled water wipe (control) is used to evaluate the permeation enhancing power of each formulation. HPLC results are as follows:

| Skin Permeation Enhancer | Ratio to Water Results |
|---|---|
| 1) 20% Salicylic Acid in 50:50-Isopropyl Alcohol:Deionized Water | 7.02→10.9 |
| 2) Tween 80 | 3.5→6.5 |
| 3) Limonane | 1→5.7 |
| 4) Isopropyl Alcohol | 1.1→1.8 |
| 5) Acetone | 1.1→1.8 |
| 6) 1:1:1-Ethyl Acetone:Isopropyl Alcohol:Water | 1→2.3 |
| 7) 90:5:5-Isopropyl Alcohol:Tween 80:Limonene | 1.7→8 |
| 8) 10% Lactic Acid in Isopropyl Alcohol | 4→11 |
| 9) 90% Lactic Acid and 10% Tween 80 | 7→16 |

In parallel with the chromatographic studies of Example 7, a certain permeation enhancer formulation is evaluated by auditioning it as a prewipe in conjunction with actual glucose monitoring patches. The performance of a certain permeation enhancer formulation is evaluated by comparing to the results obtained with a distilled water prewipe. The formulation gave reproducible results in replicate determinations, as shown in FIG. 27.

Example 9

Next, patient results obtained with various transdermal patches are compared to those obtained using a commercial fingerstick blood glucose monitor. Oral glucose tolerance tests are performed (i.e., baseline readings are performed on fasting volunteers who drank 50-75 grams of glucose and who are then retested periodically over the course of three hours). Both the baseline and the subsequent measurements are made with the glucose patch and with a commercial fingerstick blood glucose system. See FIG. 28. The glucose patch gels in this experiment are 1% Carbopol® and 10% propylene glycol in deionized water (18 meg ohm).

Example 10

Once the glucose from the interstitial fluid diffuses into the patch matrix material, it is quantitated enzymatically using glucose oxidase and peroxidase on preferably, a polyethersulphone membrane. The colored product of the peroxidase reaction, o-tolidine, is then measured by optical reflectometry. This measurement may be performed either kinetically by measuring the change in optical density at timed intervals, or else may be determined at a single fixed-time endpoint of five minutes. The latter method is the one utilized herein. The enzyme cascade and color development system is well-characterized herein. This chemistry system gives accurate and reproducible results when evaluated either by eye or by reflectometry, and the stability is shown to exceed one year. Reproducible slopes are obtained for standard curves, indicated that stored calibrations may be used to convert photometer millivolt readings into glucose concentrations expressed as mg/dl. The sensitivity of the device appears to be approximately 0.5 mg/dl, as shown in FIG. 20.

The glucose concentrations tested and shown in FIG. 29 are prepared as follows. A stock glucose solution of 1000 mg/dl is first prepared. A sample of this stock solution is then diluted in $dH_2O$ (18 meg ohm) to achieve a desired glucose concentration. Each glucose concentration made is tested and illustrated in FIG. 29. The individual glucose concentrations are then diluted 1:50 in a 1% carboxy polymethylene and 10% propylene gel of the present invention for testing. According to FIG. 29, the sensitivity of the glucose systems of the present invention appears to be at about 0.5 mg/dl or 5 meg/ml as indicated above and shown in FIG. 29.

Example 11

The results of the comparison of a standard finger prick method with glucose patch subjects are depicted in FIGS. 30-33. The gels are a 1% Carbopol® gel. Prior to application of the glucose patch, the targeted skin area is wiped with propylene glycol.

The subject in FIG. 30 receives a glucose load approximately 10 minutes after the first glucose level test is performed. As expected, after the glucose load, this subject's glucose level rises, as indicated in FIG. 30 by both the standard finger prick method and the glucose patch.

The subject in FIG. 31 intakes a high sugar meal approximately 20 minutes after the first glucose level test is performed. As shown in FIG. 31, there is an elevation in this subject's glucose level after consumption of the high sugar meal.

In FIG. 32, the subject receives a meal at about 50 minutes after the first glucose level tests. Slight elevation in glucose level is observed in FIG. 32.

In FIG. 33, a subject receives a glucose load at about 20 minutes after the first glucose tests. In spite of glucose load, little elevation in glucose level is observed, probably due to the hard work in which the subject was engaged during the testing, as shown by both the glucose patch and the standard finger prick method in FIG. 33.

These results demonstrate good correlation between the glucose patch and the standard prick method over a glucose range of 50-200 mg/dl.

Example 12

The results of the comparison of two standard finger stick methods, i.e., Blood LSP and Blood LSII, with glucose patch subjects are depicted in FIGS. 34-35. In all subjects, except the subjects depicted in FIGS. 37 and 44-45, no wipe is sued. The subjects in FIGS. 37 and 44-45 prewiped with a propylene wipe. The gels loaded into the glucose patches of this Example 12 are a 1% Carbopol® and 10% propylene glycol gel in deionized water (18 meg ohm). The results show good correlation between the two standard finger stick methods, i.e., Blood LSP and Blood LSII, with the glucose patches over a glucose range of about 75 mg/dl to about 350 mg/dl.

Example 13

Three distinct gels are tested in six subjects for permeation and diffusion enhancement. The three gels are 1% Carbopol® (CAR), 1% Carbopol® and 10% propylene glycol in deionized water (18 meg ohm) (CARPG) and 1% Carbopol® and 10% sodium lauryl sulfate in deionized water (18 meg ohm). In testing the gels, they are loaded into glucose patches and placed in contact with skin for about 5 minutes for glucose diffusion to the membrane for chemical reaction and detection. The results are shown in FIG. 46 while all three gels are effective, FIG. 46 depicts that, in all but one subject, the 1% Carbopol® and 10% propylene glycol gel is more effective.

The invention described herein extends to all such modifications and variations as will be apparent to the reader skilled in the art, and also extends to combinations and subcombinations of the features of this description and the accompanying Figs. Although preferred embodiments of the methods and apparatus of the present invention have been illustrated in the accompanying Figs. and described in the foregoing Detailed Description, it will be understood that the invention is not limited to the embodiments disclosed, but is capable of numerous rearrangements, modifications and substitutions without departing from the spirit of the invention as set forth and defined by the following claims.

Having described our invention, we claim:

1. A noninvasive transdermal system for detecting an analyte in interstitial fluid extracted from or underneath the skin of a subject, said noninvasive transdermal system comprising:

(a) a noninvasive transdermal patch comprising a target surface having a dry chemistry component for interacting with the analyte to generate color or shade of color at said target surface, said dry chemistry component having a sensitivity which enables it to detect the analyte extracted from interstitial fluid, and a wet chemistry component for transferring the analyte from the interstitial fluid in or underneath the skin to said dry chemistry component in an amount sufficient so that said dry chemistry component can detect the analyte; and (b) a reflectometer comprising a modulated light source for emitting light to illuminate said target surface which possesses a certain color and shade of color following interaction with the analyte;

an optical detector for detecting light that is reflected from said target surface and generating a first output indicative of detected light;

means for processing the first output to generate a feedback signal for application to the optical detector to compensate for any shift in the first output resulting from the detection of ambient light by the optical detector, and differentially amplify the first output to generate a second output; and a detector for synchronously demodulating the second output to generate a substantially steady DC output voltage that is indicative of the color or shade of color at said target surface.

2. The system as in claim 1 wherein the modulated light source of the reflectometer emits light having an intensity that varies with changes in temperature, the reflectometer further comprising: a temperature sensor thermo-mechanically coupled to the modulated light source, the sensor generating a third output indicative of temperature of the modulated light source; and means for mathematically correcting the substantially steady DC output voltage in accordance with the third output to account for detected changes in modulated light source temperature.

3. The system as in claim 2 wherein the modulated light source comprises at least one light emitting diode, and wherein the temperature sensor comprises a diode means having an operating characteristic substantially complementing that of the light emitting diode.

4. The system as in claim 1 wherein the modulated light source of the reflectometer emits light having an intensity that varies with changes in temperature, the reflectometer further comprising: a temperature compensator thermo-mechanically coupled to the modulated light source; and means for having the temperature compensator control operation of the modulated light source to counteract for any variations in light intensity due to changes in modulated light source temperature.

5. The system as in claim 4 wherein the modulated light source of the reflectometer comprises at least one light emitting diode, wherein the temperature compensator comprises a diode, and wherein the means for having comprises a series electrical connection of the diode with the light emitting diode.

6. The system as in claim 1 wherein the modulated light source of the reflectometer emits light having an intensity that varies with changes in voltage drop across the modulated light source, the reflectometer further comprising:
a sensor for measuring voltage drop across the modulated light source during target surface illumination; and
means for mathematically correcting the substantially steady DC output voltage in accordance with the measured voltage drop to account for variations in light intensity.

7. The system as in claim 1 wherein the optical detector of the reflectometer comprises: a photo transistor for receiving and detecting light that is reflected from the target surface and generating a first differential signal, a transistor for setting the quiescent operating point and generating a second differential signal; and means for connecting the photo transistor and transistor at a common emitter connection in a differential configuration.

8. The system as in claim 7 further comprising a current mirror for supplying fixed constant current into the common emitter connection between the differentially connected photo transistor and transistor.

9. The system as in claim 7 wherein the means for processing processes the second differential signal to generate the feedback signal for application to the photo transistor to bias the photo transistor to the quiescent operating point.

10. The system as in claim 9 wherein the means for processing comprises an integrator for comparing the second differential signal to a reference voltage and integrating a result of the comparison to generate the feedback signal, wherein the feedback signal is indicative of an error between the quiescent operating point and a shift caused by DC ambient light detected at the photo transistor.

11. The system as in claim 1 wherein the modulated light source of the reflectometer comprises: at least two light emitting diodes; and means for mounting the light emitting diodes each at an orientation angle away from an orientation angle of the optical detector so as to provide for substantially uniform illumination of the target surface with minimal specular reflection to the optical detector.

12. The system as in claim 11 wherein the two light emitting diodes are of different color.

13. The system as in claim 1 wherein the detector for synchronously demodulating comprises a full wave synchronous detector producing a DC voltage proportional to the peak to peak voltage of the second output signal.

14. The system as in claim 1 further including a hand held case for containing the modulated light source, differential optical detector, differential amplifier, and synchronous detector.

15. The system as in claim 14 wherein the target surface comprises a color developing membrane of a transdermal patch, and the hand held case includes a reader head adapted for mating with the color developing membrane of the transdermal patch.

16. The system as in claim 15 wherein the transdermal patch includes an opening exposing the color developing membrane to view, and the reader head includes a nose configured for insertion into the transdermal patch opening.

17. The system as in claim 16 wherein the nose of the reader head includes a transparent window for flattening the color developing membrane when the reader head is inserted into the transdermal patch opening.

18. The system as in claim 16 wherein the opening in the transdermal patch has a certain size and shape, and wherein the nose configuration of the reader head has a complementary size and shape.

19. The system as in claim 16 wherein the opening is circular, and wherein the nose configuration has a cylindrical shape adapted to fit within the circular opening.

20. The system as in claim 19 wherein the cylindrical shape of the nose configuration is tapered to allow the reader head to find the circular opening.

21. The system as in claim 1 further including a desk top case for containing the modulated light source, differential optical detector, differential amplifier, and synchronous detector.

22. The system as in claim 21 wherein the target surface comprises a color developing testing strip, and the desk top case includes a reader site adapted for constraining the color developing test strip.

23. The system as in claim 1 wherein the target surface color shade is indicative of a certain measurable quantity or quality, the reflectometer further comprising a processor for converting the steady DC voltage indicative of the color or shade of color at said target surface into a corresponding quantity or quality measurement.

24. The system as in claim 23 further comprising a stored look-up table or mathematical formula correlating steady DC voltage values to corresponding quantity or quality measurements, the processor consulting the look-up table or mathematical formula in making its conversion.

25. The system as in claim 24 wherein the measurable quantity or quality comprises an analyte concentration.

26. The system as in claim 25 wherein the analyte concentration comprises either a glucose level or a cholesterol level.

27. The system as in claim 1 wherein the modulated light source of the reflectometer emits light having an intensity that varies with changes in temperature, and wherein the target surface color shade is indicative of a certain measurable quantity or quality, the reflectometer further comprising: a sensor generating a temperature signal indicative of light source temperature; and a processor for correcting the steady DC voltage indicative of the color or shade of color at the target surface in accordance with the temperature signal to generate a compensated DC voltage, and for converting the compensated DC voltage into a corresponding quantity or quality measurement.

28. The noninvasive transdermal system of claim 1 where said wet chemistry component is a gel.

29. The noninvasive transdermal system of claim 28 wherein said gel comprises carboxy polymethylene and propylene glycol.

30. The noninvasive transdermal system of claim 28 wherein said gel consists essentially of 1% carboxy polymethylene and 10% propylene glycol.

31. A noninvasive transdermal system of claim 1 wherein the analyte is transferred in about 10 minutes or less.

32. A noninvasive transdermal system of claim 1 wherein the analyte is transferred in about 5 minutes or less.

33. A noninvasive method of detecting an analyte in a biological fluid extracted from or underneath the skin of a subjects comprising the steps of:
(a) positioning the noninvasive transdermal patch of claim 1 on the skin of the subject; and
(b) detecting the analyte with the reflectometer within about 15 minutes or less following said positioning while the noninvasive transdermal patch is positioned on the skin.

34. The noninvasive method as in claim 33 wherein said detection occurs within about 10 minutes or less.

35. The noninvasive method as in claim 34 wherein said wet chemistry component is a gel.

36. The noninvasive method as in claim 35 wherein said gel comprises carboxy polymethylene and propylene glycol.

37. The noninvasive method as in claim 36 wherein said gel consists essentially of 1% carboxy polymethylene and 10% propylene glycol.

38. The noninvasive method as in claim 33 wherein said detection occurs within about 5 minutes or less.

39. The noninvasive method as in claim 38 wherein said wet chemistry component is a gel.

40. The noninvasive method as in claim 39 wherein said gel comprises carboxy polymethylene and propylene glycol.

41. The noninvasive method as in claim 40 wherein said gel consists essentially of 1% carboxy polymethylene and 10% propylene glycol.

42. The noninvasive method as in claim 33 wherein said wet chemistry component is a gel.

43. The noninvasive method as in claim 42 wherein said gel comprises carboxy polymethylene and propylene glycol.

44. The noninvasive method as in claim 43 wherein said gel consists essentially of 1% carboxy polymethylene and 10% propylene glycol.

45. A noninvasive transdermal system for detecting an analyte in a biological fluid extracted from or underneath the skin of a subject, said noninvasive transdermal system comprising:
(a) a noninvasive transdermal patch comprising a target surface having a dry chemistry component for interacting with the analyte to generate color or shade of color at said target surface, a dry chemistry component for interacting with the analyte to detect the analyte, said dry chemistry component having a sensitivity which enables it to detect the analyte extracted from interstitial fluid, and a wet chemistry component for transferring in about 15 minutes or less the analyte from the interstitial fluid in or underneath the skin to said dry chemistry component in an amount sufficient, so that said dry chemistry component can interact with the analyte to generate color or shade of color at said target surface for detecting the analyte, said wet chemistry component consisting essentially of a gel and a skin permeate enhancer;
(b) a reflectometer comprising a light source for emitting light to illuminate said target surface which possesses a certain color and shade of color;
an optical detector circuit for detecting light that is reflected from the target surface and generating a substantially steady DC output voltage that is indicative of the color or shade of color at said target surface;
a stored look-up table or mathematical formula correlating steady DC voltage values to corresponding quantity or quality measurements for each one of a plurality of different tests; and
a processor for consulting the stored look-up table or mathematical formula for a certain test being performed, and converting the steady DC voltage indicative of the color or shade of color at said target surface into a corresponding quantity or quality measurement in accordance with that certain test; and wherein the light source is a modulated light source and wherein the optical detector circuit comprises:
an optical detector for detecting light that is reflected from the target surface and generating a first output indicative of detected light;
means for processing the first output to generate a feedback signal for application to the optical detector to compensate for any shift in the first output resulting from the detection of ambient light by the optical detector, and differentially amplify the first output to generate a second output; and
a detector for synchronously demodulating the second output to generate the substantially steady DC output voltage that is indicative of the color or shade of color at the target surface.

46. The system as in claim 45 wherein the optical detector of the reflectometer comprises:
a photo transistor for receiving and detecting light that is reflected from the target surface and generating a first differential signal;
a transistor for setting the quiescent operating point and generating a second differential signal; and
means for connecting the photo transistor and transistor at a common emitter connection in a differential configuration.

47. The system as in claim 45 wherein the means for processing processes the second differential signal to generate the feedback signal for application to the photo transistor to bias the photo transistor to the quiescent operating point.

48. The system as in claim 45 wherein the means for processing comprises an integrator for comparing the second differential signal to a reference voltage and integrating a result of the comparison to generate the feedback signal, wherein the feedback signal is indicative of an error between the quiescent operating point and a shift caused by DC ambient light detected at the photo transistor.

49. The system as in claim 45 wherein the detector for synchronously demodulating comprises a full wave synchronous detector producing a DC voltage proportional to the peak to peak voltage of the second output signal.

50. The system as in claim 45 further including means for calibrating the reflectometer to each stored look-up table or mathematical formula for each one of the plurality of different tests.

51. The system as in claim 50 wherein the means for calibrating comprises means for setting the reflectometer to read a certain DC output voltage at a mid point corresponding to a certain color or shade of color.

52. The system as in claim 51 wherein the means for calibrating further comprises means for determining an offset for application to read DC output voltages at end points each corresponding to a certain color or shade of color.

53. The system as in claim 51 wherein the means for calibrating further comprises means for determining an offset for application to a read DC output voltage at mid point for a certain test and corresponding to a certain color or shade of color.

54. The system as in claim 51 wherein the means for calibrating further comprises means for determining an offset for application to read DC output voltages at end points each corresponding to a certain color or shade of color within a given batch.

55. The noninvasive transdermal system of claim 45 wherein the biological fluid is interstitial fluid.

56. The noninvasive transdermal system of claim 45 wherein the analyte is glucose.

57. The noninvasive transdermal system of claim 45 wherein said wet chemistry component is a gel which includes carboxy polymethylene, and said skin penetrant is propylene glycol.

58. The noninvasive transdermal system of claim 57 wherein said gel consists essentially of 1% carboxy polymethylene and 10% propylene glycol.

59. The noninvasive transdermal system of claim 45 wherein the analyte is transferred in about 10 minutes or less.

60. A noninvasive transdermal system of claim 45 wherein the analyte is transferred in about 5 minutes or less.

61. A noninvasive method of detecting an analyze in a biological fluid extracted from or underneath the skin of a subject, comprising the steps of:
 (a) positioning the noninvasive transdermal patch of claim 45 on the skin of the subject; and
 (b) detecting the analyte with the reflectometer within about 15 minutes or less following said positioning while the noninvasive transdermal patch is positioned on the skin.

62. The noninvasive method as in claim 61 wherein said detection occurs within about 10 minutes or less.

63. The noninvasive method as in claim 62 wherein said wet chemistry component is a gel.

64. The noninvasive method as in claim 63 wherein said gel comprises carboxy polymethylene and propylene glycol.

65. The noninvasive method as in claim 64 wherein said gel consists essentially of 1% carboxy polymethylene and 10% propylene glycol.

66. The noninvasive method as in claim 61 wherein said detection occurs within about 5 minutes or less.

67. The noninvasive method as in claim 66 wherein said wet chemistry component is a gel.

68. The noninvasive method as in claim 67 wherein said gel comprises carboxy polymethylene and propylene glycol.

69. The noninvasive method as in claim 68 wherein said gel consists essentially of 1% carboxy polymethylene and 10% propylene glycol.

70. The noninvasive method as in claim 61 wherein said wet chemistry component is a gel.

71. The noninvasive method as in claim 70 wherein said gel comprises carboxy polymethylene and propylene glycol.

72. The noninvasive method as in claim 71 wherein said gel consists essentially of 1% carboxy polymethylene and 10% propylene glycol.

* * * * *

UNITED STATES PATENT AND TRADEMARK OFFICE
CERTIFICATE OF CORRECTION

PATENT NO. : 7,577,469 B1
APPLICATION NO. : 09/266346
DATED : August 18, 2009
INVENTOR(S) : Jack L. Aronowitz et al.

It is certified that error appears in the above-identified patent and that said Letters Patent is hereby corrected as shown below:

Column 2, Line 67:
"Dahne *et al. al.*" should read --Dahne *et al.*--

Column 16, Line 25:
"slider patch 610" should read --slider patch 600--

Column 16, Line 29:
"housing 610" should read --housing 620--

Column 17, Line 16:
"housing 520" should read --housing 820--

Column 17, Line 17:
"wet chemistry" should read --dry chemistry--

Column 17, Line 21:
"gel 812" should read --gel 822--

Column 18, Line 5:
"$OH_2O$:" should read --$dH_2O$:--

Column 25, Line 10:
"and a light" should read --and light--

Column 29, Line 39:
"LEDs 500" should read --LEDs 5000--

Column 33, Line 23:
"computer 136" should read --computer 13600--

Column 33, Line 31:
"reflectometer 30/30'" should read --reflectometer 3000/3000'--

Column 43, Line 56:
"reflectometer 3000/30'" should read --reflectometer 3000/3000'--

UNITED STATES PATENT AND TRADEMARK OFFICE
CERTIFICATE OF CORRECTION

PATENT NO. : 7,577,469 B1
APPLICATION NO. : 09/266346
DATED : August 18, 2009
INVENTOR(S) : Jack L. Aronowitz et al.

It is certified that error appears in the above-identified patent and that said Letters Patent is hereby corrected as shown below:

Column 53, Line 30:
FIGS. 21, 22, 23, 24 and 25.

" WIPE/GEL   1   2   3 " should read

FIGS. 21, 22, 23, 24 and 25.

MM

-- WIPE/GEL   1   2   3   --

Column 53, Line 40:
" WIPE/GEL   1   2   3 " should read

--

JM

WIPE/GEL   1   2   3   --

UNITED STATES PATENT AND TRADEMARK OFFICE
CERTIFICATE OF CORRECTION

PATENT NO. : 7,577,469 B1
APPLICATION NO. : 09/266346
DATED : August 18, 2009
INVENTOR(S) : Jack L. Aronowitz et al.

It is certified that error appears in the above-identified patent and that said Letters Patent is hereby corrected as shown below:

Column 58, Line 61:
"subjects" should read --subject--

Column 61, Claim 61:
"analyze" should read --analyte--

Signed and Sealed this

Twenty-seventh Day of October, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,577,469 B1 | |
| APPLICATION NO. | : 09/266346 | |
| DATED | : August 18, 2009 | |
| INVENTOR(S) | : Jack L. Aronowitz et al. | |

It is certified that error appears in the above-identified patent and that said Letters Patent is hereby corrected as shown below:

Column 2, Line 67:
"Dahne *et al. al.*" should read --Dahne *et al.*--

Column 16, Line 25:
"slider patch 610" should read --slider patch 600--

Column 16, Line 29:
"housing 610" should read --housing 620--

Column 17, Line 16:
"housing 520" should read --housing 820--

Column 17, Line 17:
"wet chemistry" should read --dry chemistry--

Column 17, Line 21:
"gel 812" should read --gel 822--

Column 18, Line 5:
"$OH_2O$:" should read --$dH_2O$:--

Column 25, Line 10:
"and a light" should read --and light--

Column 29, Line 39:
"LEDs 500" should read --LEDs 5000--

Column 33, Line 23:
"computer 136" should read --computer 13600--

Column 33, Line 31:
"reflectometer 30/30'" should read --reflectometer 3000/3000'--

Column 43, Line 56:
"reflectometer 3000/30'" should read --reflectometer 3000/3000'--

UNITED STATES PATENT AND TRADEMARK OFFICE
CERTIFICATE OF CORRECTION

PATENT NO. : 7,577,469 B1  
APPLICATION NO. : 09/266346  
DATED : August 18, 2009  
INVENTOR(S) : Jack L. Aronowitz et al.

Page 2 of 3

It is certified that error appears in the above-identified patent and that said Letters Patent is hereby corrected as shown below:

Column 53, Line 30:
FIGS. 21, 22, 23, 24 and 25.

" | WIPE/GEL | 1 | 2 | 3 | " should read

FIGS. 21, 22, 23, 24 and 25.

MM

-- | WIPE/GEL | 1 | 2 | 3 | --

Column 53, Line 40:

" | WIPE/GEL | 1 | 2 | 3 | " should read

--

JM

| WIPE/GEL | 1 | 2 | 3 | --

UNITED STATES PATENT AND TRADEMARK OFFICE
CERTIFICATE OF CORRECTION

PATENT NO. : 7,577,469 B1
APPLICATION NO. : 09/266346
DATED : August 18, 2009
INVENTOR(S) : Jack L. Aronowitz et al.

It is certified that error appears in the above-identified patent and that said Letters Patent is hereby corrected as shown below:

Column 58, Line 61:
"subjects" should read --subject--

Column 61, Claim 61, Line 8:
"analyze" should read --analyte--

This certificate supersedes the Certificate of Correction issued October 27, 2009.

Signed and Sealed this

First Day of December, 2009

David J. Kappos
*Director of the United States Patent and Trademark Office*